United States Patent
Verkade et al.

(10) Patent No.: US 10,792,369 B2
(45) Date of Patent: *Oct. 6, 2020

(54) SULFAMIDE LINKER, CONJUGATES THEREOF, AND METHODS OF PREPARATION

(71) Applicant: Synaffix B.V., Oss (NL)

(72) Inventors: Jorge Merijn Mathieu Verkade, Eindhoven (NL); Maria Antonia Wijdeven, Lent (NL); Petrus Josephus Jacobus Maria Van De Sande, Eindhoven (NL); Sander Sebastiaan Van Berkel, Lent (NL); Floris Louis Van Delft, Nijmegen (NL)

(73) Assignee: SYNAFFIX B.V., Oss (NL)

( * ) Notice: Subject to any disclaimer, the term of this patent is extended or adjusted under 35 U.S.C. 154(b) by 185 days.

This patent is subject to a terminal disclaimer.

(21) Appl. No.: 15/581,226

(22) Filed: Apr. 28, 2017

(65) Prior Publication Data

US 2017/0298145 A1    Oct. 19, 2017

Related U.S. Application Data

(63) Continuation of application No. 15/360,610, filed on Nov. 23, 2016, now Pat. No. 9,636,421, which is a (Continued)

(30) Foreign Application Priority Data

Oct. 3, 2014 (EP) .................................. 14187615

(51) Int. Cl.
*C07K 16/32* (2006.01)
*A61K 47/68* (2017.01)

(52) U.S. Cl.
CPC ...... *A61K 47/6803* (2017.08); *A61K 47/6811* (2017.08); *A61K 47/6851* (2017.08); (Continued)

(58) Field of Classification Search
CPC ................ A61K 39/44; A61K 2039/62; A61K 47/48376; A61K 16/32; A61K 47/48384; (Continued)

(56) References Cited

U.S. PATENT DOCUMENTS 4,585,862 A      4/1986  Wang et al.
9,636,421 B2 *   5/2017  Verkade ................ C07K 16/32
(Continued)

FOREIGN PATENT DOCUMENTS

EP          0 199 963 A1    11/1985
WO          WO-01/88535 A1  11/2001
(Continued)

OTHER PUBLICATIONS

Babic et al.,"Synthesis of 1-C-linked diphosphate analogues of UDP-N-Ac-glucosamine and UDP-N-Ac-muramic acid", Tetrahedron, 2008, vol. 64, pp. 9093-9100.
(Continued)

*Primary Examiner* — Shafiqul Haq
(74) *Attorney, Agent, or Firm* — Foley & Lardner LLP

(57) ABSTRACT

The present invention relates to a compound comprising an alpha-end and an omega-end, the compound comprising on the alpha-end a reactive group $Q^1$ capable of reacting with a functional group $F^1$ present on a biomolecule and on the omega-end a target molecule, the compound further comprising a group according to formula (1) or a salt thereof:

(Continued)

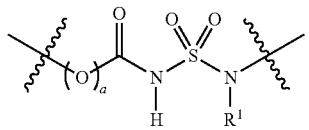

Said compound may also be referred to as a linker-conjugate. The invention also relates to a process for the preparation of a bioconjugate, the process comprising the step of reacting a reactive group $Q^1$ of a linker-conjugate according to the invention with a functional group $F^1$ of a biomolecule. The invention further relates to a bioconjugate obtainable by the process according to the invention.

25 Claims, 20 Drawing Sheets

Specification includes a Sequence Listing.

Related U.S. Application Data continuation of application No. PCT/NL2015/050697, filed on Oct. 5, 2015.

(52) U.S. Cl.
CPC ...... *A61K 47/6855* (2017.08); *A61K 47/6889* (2017.08); *C07K 16/32* (2013.01)

(58) Field of Classification Search
CPC ............ A61K 47/48584; C07C 311/01; C07C 311/02; C07C 311/50; A01B 12/006
See application file for complete search history.

(56) References Cited

U.S. PATENT DOCUMENTS

| | | | |
|---|---|---|---|
| 2019/0262466 A1* | 8/2019 | Van Berkel | A61K 47/6869 |
| 2019/0262467 A1* | 8/2019 | Verkade | A61K 47/6889 |
| 2019/0262468 A1* | 8/2019 | Van Berkel | A61K 47/6889 |

FOREIGN PATENT DOCUMENTS

| | | |
|---|---|---|
| WO | WO-2006/027711 A2 | 3/2006 |
| WO | WO-2008/070291 | 6/2008 |
| WO | WO-2014/100762 A1 | 6/2014 |
| WO | WO-2014/144871 A1 | 9/2014 |
| WO | WO-2015/095953 A1 | 7/2015 |

OTHER PUBLICATIONS

Dennler et al., "Transglutaminase-based chemo-enzymatic conjugation approach yields homogeneous antibody-drug conjugates", Bioconjugate Chemistry, 2014, vol. 25, pp. 569-578.
Duckworth et al., "Bisubstrate adenylation inhibitors of biotin protein ligase from *Mycobacterium tuberculosis*", Chemistry & Biology, Nov. 23, 2011, vol. 18, pp. 1432-1441.
International Search Report issued in International Patent Application No. PCT/NL2015/050697 dated Mar. 7, 2016.
Li et al., "Preparation of well-defined antibody-drug conjugates through glycan remodeling and strain-promoted azide-alkyne cycloadditions", Angew. Chem. Int. Ed., 2014, vol. 53, pp. 7179-7182.
Lu et al., "Designed semisynthetic protein inhibitors of Ub/Ubl E1 activating enzymes", Journal of the American Chemical Society, 2010, vol. 132, pp. 1748-1749.
Lyon et al., "Self-hydrolyzing maleimides improve the stability and pharmacological properties of antibody-drug conjugates", Nature Biotechnology, Oct. 2014, vol. 32, pp. 1059-1065.
Melagraki et al., "Identification of a series of novel derivatives as potent HCV inhibitors by a ligand-based virtual screening optimized procedure", Bioorganic & Medicinal Chemistry, 2007, vol. 15, pp. 7237-7247.

\* cited by examiner

BOI = biomolecule of interest
D = MOI = molecule of interest (or target molecule)
$F_1$ = native or engineered functional group
$Q_1$ = reactive group specific for $F_1$
n = 1,2,3...

BOI = peptide/protein or glycan or nucleic acid

SEQUENCE LISTING

<160> NUMBER OF SEQ ID NOS: 5

<210> SEQ ID NO 1
<211> LENGTH: 358
<212> TYPE: PRT

<213> ORGANISM: Artificial
<220> FEATURE:
<223> OTHER INFORMATION: GalT double mutant (Y289L, C342T)

<400> SEQUENCE: 1

```
Arg Asp Leu Arg Arg Leu Pro Gln Leu Val Gly Val His Pro Pro Leu
1               5                   10                  15

Gln Gly Ser Ser His Gly Ala Ala Ile Gly Gln Pro Ser Gly Glu
            20                  25                  30

Leu Arg Leu Arg Gly Val Ala Pro Pro Pro Leu Gln Asn Ser Ser
        35                  40                  45

Lys Pro Arg Ser Arg Ala Pro Ser Asn Leu Asp Ala Tyr Ser His Pro
50                  55                  60

Gly Pro Gly Pro Gly Pro Gly Ser Asn Leu Thr Ser Ala Pro Val Pro
65                  70                  75                  80

Ser Thr Thr Thr Arg Ser Leu Thr Ala Cys Pro Glu Glu Ser Pro Leu
                85                  90                  95

Leu Val Gly Pro Met Leu Ile Glu Phe Asn Ile Pro Val Asp Leu Lys
                100                 105                 110

Leu Val Glu Gln Gln Asn Pro Lys Val Lys Leu Gly Gly Arg Tyr Thr
            115                 120                 125

Pro Met Asp Cys Ile Ser Pro His Lys Val Ala Ile Ile Ile Pro Phe
        130                 135                 140

Arg Asn Arg Gln Glu His Leu Lys Tyr Trp Leu Tyr Tyr Leu His Pro
145                 150                 155                 160

Ile Leu Gln Arg Gln Gln Leu Asp Tyr Gly Ile Tyr Val Ile Asn Gln
                165                 170                 175

Ala Gly Glu Ser Met Phe Asn Arg Ala Lys Leu Leu Asn Val Gly Phe
            180                 185                 190

Lys Glu Ala Leu Lys Asp Tyr Asp Tyr Asn Cys Phe Val Phe Ser Asp
        195                 200                 205

Val Asp Leu Ile Pro Met Asn Asp His Asn Thr Tyr Arg Cys Phe Ser
210                 215                 220

Gln Pro Arg His Ile Ser Val Ala Met Asp Lys Phe Gly Phe Ser Leu
225                 230                 235                 240

Pro Tyr Val Gln Leu Phe Gly Gly Val Ser Ala Leu Ser Lys Gln Gln
                245                 250                 255

Phe Leu Ser Ile Asn Gly Phe Pro Asn Asn Tyr Trp Gly Trp Gly Gly
            260                 265                 270

Glu Asp Asp Asp Ile Tyr Asn Arg Leu Ala Phe Arg Gly Met Ser Val
        275                 280                 285

Ser Arg Pro Asn Ala Val Ile Gly Lys Thr Arg Met Ile Arg His Ser
290                 295                 300

Arg Asp Lys Lys Asn Glu Pro Asn Pro Gln Arg Phe Asp Arg Ile Ala
305                 310                 315                 320

His Thr Lys Glu Thr Met Leu Ser Asp Gly Leu Asn Ser Leu Thr Tyr
                325                 330                 335

Met Val Leu Glu Val Gln Arg Tyr Pro Leu Tyr Thr Lys Ile Thr Val
            340                 345                 350

Asp Ile Gly Thr Pro Ser
        355
```

<210> SEQ ID NO 2
<211> LENGTH: 354
<212> TYPE: PRT

<213> ORGANISM: Artificial
<220> FEATURE:
<223> OTHER INFORMATION: CeGalNAcT [30-383]

<400> SEQUENCE: 2

```
Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ile Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe
```

<210> SEQ ID NO 3
<211> LENGTH: 360
<212> TYPE: PRT
<213> ORGANISM: Artificial

<220> FEATURE:
<223> OTHER INFORMATION: CeGalNAcT(30-383)-His6

<400> SEQUENCE: 3

Lys Ile Pro Ser Leu Tyr Glu Asn Leu Thr Ile Gly Ser Ser Thr Leu
1               5                   10                  15

Ile Ala Asp Val Asp Ala Met Glu Ala Val Leu Gly Asn Thr Ala Ser
            20                  25                  30

Thr Ser Asp Asp Leu Leu Asp Thr Trp Asn Ser Thr Phe Ser Pro Ile
        35                  40                  45

Ser Glu Val Asn Gln Thr Ser Phe Met Glu Asp Ile Arg Pro Ile Leu
    50                  55                  60

Phe Pro Asp Asn Gln Thr Leu Gln Phe Cys Asn Gln Thr Pro Pro His
65                  70                  75                  80

Leu Val Gly Pro Ile Arg Val Phe Leu Asp Glu Pro Asp Phe Lys Thr
                85                  90                  95

Leu Glu Lys Ile Tyr Pro Asp Thr His Ala Gly Gly His Gly Met Pro
            100                 105                 110

Lys Asp Cys Val Ala Arg His Arg Val Ala Ile Ile Val Pro Tyr Arg
        115                 120                 125

Asp Arg Glu Ala His Leu Arg Ile Met Leu His Asn Leu His Ser Leu
    130                 135                 140

Leu Ala Lys Gln Gln Leu Asp Tyr Ala Ile Phe Ile Val Glu Gln Val
145                 150                 155                 160

Ala Asn Gln Thr Phe Asn Arg Gly Lys Leu Met Asn Val Gly Tyr Asp
                165                 170                 175

Val Ala Ser Arg Leu Tyr Pro Trp Gln Cys Phe Ile Phe His Asp Val
            180                 185                 190

Asp Leu Leu Pro Glu Asp Asp Arg Asn Leu Tyr Thr Cys Pro Ile Gln
        195                 200                 205

Pro Arg His Met Ser Val Ala Ile Asp Lys Phe Asn Tyr Lys Leu Pro
    210                 215                 220

Tyr Ser Ala Ile Phe Gly Gly Ile Ser Ala Leu Thr Lys Asp His Leu
225                 230                 235                 240

Lys Lys Ile Asn Gly Phe Ser Asn Asp Phe Trp Gly Trp Gly Gly Glu
                245                 250                 255

Asp Asp Asp Leu Ala Thr Arg Thr Ser Met Ala Gly Leu Lys Val Ser
            260                 265                 270

Arg Tyr Pro Thr Gln Ile Ala Arg Tyr Lys Met Ile Lys His Ser Thr
        275                 280                 285

Glu Ala Thr Asn Pro Val Asn Lys Cys Arg Tyr Lys Ile Met Gly Gln
    290                 295                 300

Thr Lys Arg Arg Trp Thr Arg Asp Gly Leu Ser Asn Leu Lys Tyr Lys
305                 310                 315                 320

Leu Val Asn Leu Glu Leu Lys Pro Leu Tyr Thr Arg Ala Val Val Asp
                325                 330                 335

Leu Leu Glu Lys Asp Cys Arg Arg Glu Leu Arg Arg Asp Phe Pro Thr
            340                 345                 350

Cys Phe His His His His His His
        355                 360

<210> SEQ ID NO 4
<211> LENGTH: 449
<212> TYPE: PRT
<213> ORGANISM: Artificial

<220> FEATURE:
<223> OTHER INFORMATION: Trastuzumab(heavy chain N300C)

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 5
<211> LENGTH: 107
<212> TYPE: PRT
<213> ORGANISM: Artificial
<220> FEATURE:
<223> OTHER INFORMATION: Trastuzumab(light chain)

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

SULFAMIDE LINKER, CONJUGATES THEREOF, AND METHODS OF PREPARATION

CROSS-REFERENCE TO RELATED APPLICATIONS

This application is a continuation application of U.S. patent application Ser. No. 15/360,610, which is a continuation application filed under 35 U.S.C. § 111(a) claiming the benefit under 35 U.S.C. §§ 120 and 365(c) of International Application No. PCT/NL2015/050697 filed on Oct. 5, 2015, which is based upon and claims the benefit of priority of European Patent Application No. 14187615.1, filed on Oct. 3, 2014, the entire contents of which are all hereby incorporated by reference.

The instant application contains a Sequence Listing which has been submitted in ASCII format via EFS-WEB and is hereby incorporated by reference in its entirety. Said ASCII copy, created on Apr. 27, 2017, is named 069818-1331_SequenceListing.txt and is 16 KB.

TECHNICAL FIELD OF THE INVENTION

The present invention is in the field of bioconjugation. The invention relates to sulfamide linkers and conjugates thereof, and to methods for the preparation thereof. More particularly, the invention relates to linkers comprising an acylsulfamide group and/or a carbamoyl sulfamide group and to conjugates comprising said linkers. The invention further relates to a process for the preparation of bioconjugates comprising a linker, the linker comprising an acylsulfamide group and/or a carbamoyl sulfamide group.

BACKGROUND OF THE INVENTION

Bioconjugation is the process of linking two or more molecules, of which at least one is a biomolecule. The biomolecule(s) may also be referred to as "biomolecule(s) of interest", the other molecule(s) may also be referred to as "target molecule" or "molecule of interest". Typically the biomolecule of interest (BOI) will consist of a protein (or peptide), a glycan, a nucleic acid (or oligonucleotide), a lipid, a hormone or a natural drug (or fragments or combinations thereof). The other molecule of interest (MOI) may also be a biomolecule, hence leading to the formation of homo- or heterodimers (or higher oligomers), or the other molecule may possess specific features that are imparted onto the biomolecule of interest by the conjugation process. For example, the modulation of protein structure and function by covalent modification with a chemical probe for detection and/or isolation has evolved as a powerful tool in proteome-based research and biomedical applications. Fluorescent or affinity tagging of proteins is key to studying the trafficking of proteins in their native habitat. Vaccines based on protein-carbohydrate conjugates have gained prominence in the fight against HIV, cancer, malaria and pathogenic bacteria, whereas carbohydrates immobilized on microarrays are instrumental in elucidation of the glycome. Synthetic DNA and RNA oligonucleotides (ONs) require the introduction of a suitable functionality for diagnostic and therapeutic applications, such as microarray technology, antisense and gene-silencing therapies, nanotechnology and various materials sciences applications. For example, attachment of a cell-penetrating ligand is the most commonly applied strategy to tackle the low internalization rate of ONs encountered during oligonucleotide-based therapeutics (antisense, siRNA). Similarly, the preparation of oligonucleotide-based microarrays requires the selective immobilization of ONs on a suitable solid surface, e.g. glass.

There are numerous examples of chemical reactions suitable to covalently link two (or more) molecular structures. However, labeling of biomolecules poses high restrictions on the reaction conditions that can be applied (solvent, concentration, temperature), while the desire of chemoselective labeling limits the choice of reactive groups. For obvious reasons, biological systems generally flourish best in an aqueous environment meaning that reagents for bioconjugation should be suitable for application in aqueous systems. In general, two strategic concepts can be recognized in the field of bioconjugation technology: (a) conjugation based on a functional group already present in the biomolecule of interest, such as for example a thiol, an amine, an alcohol or a hydroxyphenol unit or (b) a two-stage process involving engineering of one (or more) unique reactive groups into a BOI prior to the actual conjugation process.

The first approach typically involves a reactive amino acid side-chain in a protein (e.g. cysteine, lysine, serine and tyrosine), or a functional group in a glycan (e.g. amine, aldehyde) or nucleic acid (e.g. purine or pyrimidine functionality or alcohol). As summarized inter alia in G. T. Hermanson, "*Bioconjugate Techniques*", Elsevier, $3^{rd}$ Ed. 2013, incorporated by reference, a large number of reactive functional groups have become available over the years for chemoselective targeting of one of these functional groups, such as maleimide, haloacetamide, activated ester, activated carbonate, sulfonyl halide, activated thiol derivative, alkene, alkyne, allenamide and more, each of which requiring its own specific conditions for conjugation (pH, concentration, stoichiometry, light, etc.). Most prominently, cysteine-maleimide conjugation stands out for protein conjugation by virtue of its high reaction rate and chemoselectivity. However, when no cysteine is available for conjugation, as in many proteins and certainly in other biomolecules, other methods are often required, each suffering from its own shortcomings.

An elegant and broadly applicable solution for bioconjugation involves the two-stage approach. Although more laborious, two-stage conjugation via engineered functionality typically leads to higher selectivity (site-specificity) than conjugation on a natural functionality. Besides that, full stability can be achieved by proper choice of construct, which can be an important shortcoming of one stage conjugation on native functionality, in particular for cysteine-maleimide conjugation. Typical examples of a functional group that may be imparted onto the BOI include (strained) alkyne, (strained) alkene, norbornene, tetrazine, azide, phosphine, nitrile oxide, nitrone, nitrile imine, diazo compound, carbonyl compound, (O-alkyl)hydroxylamine and hydrazine, which may be achieved by either chemical or molecular biology approach. Each of the above functional groups is known to have at least one reaction partner, in many cases involving complete mutual reactivity. For example, cyclooctynes react selectively and exclusively with 1,3-dipoles, strained alkenes with tetrazines and phosphines with azides, leading to fully stable covalent bonds. However, some of the above functional groups have the disadvantage of being highly lipophilic, which may compromise conjugation efficiency, in particular in combination with a lipophilic molecule of interest (see below).

The final linking unit between the biomolecule and the other molecule of interest should preferentially also be fully compatible with an aqueous environment in terms of solubility, stability and biocompatibility. For example, a highly lipophilic linker may lead to aggregation (during or after conjugation), which may significantly increase reaction times and/or reduce conjugation yields, in particular when the MOI is also of hydrophobic nature. Similarly, highly lipophilic linker-MOI combination may lead to unspecific binding to surfaces or specific hydrophobic patches on the same or other biomolecules. If the linker is susceptible to aqueous hydrolysis or other water-induced cleavage reactions, the components comprising the original bioconjugate separate by diffusion. For example, certain ester moieties are not suitable due to saponification while β-hydroxycarbonyl or γ-dicarbonyl compounds could lead to retro-aldol or retro-Michael reaction, respectively. Finally, the linker should be inert to functionalities present in the bioconjugate or any other functionality that may be encountered during application of the bioconjugate, which excludes, amongst others, the use of linkers featuring for example a ketone or aldehyde moiety (may lead to imine formation), an α,β-unsaturated carbonyl compound (Michael addition), thio-esters or other activated esters (amide bond formation).

Compounds made of linear oligomers of ethylene glycol, so-called PEG (polyethyleneglycol) linkers, enjoy particular popularity nowadays in biomolecular conjugation processes. PEG linkers are highly water soluble, non-toxic, non-antigenic, and lead to negligble or no aggregation. For this reason, a large variety of linear, bifunctional PEG linkers are commercially available from various sources, which can be selectively modified at either end with a (bio)molecule of interest. PEG linkers are the product of a polymerization process of ethylene oxide and are therefore typically obtained as stochastic mixtures of chain length, which can be partly resolved into PEG constructs with an average weight distribution centered around 1, 2, 4 kDa or more (up to 60 kDa). Homogeneous, discrete PEGs (dPEGs) are also known with molecular weights up to 4 kDa and branched versions thereof go up to 15 kDa. Interestingly, the PEG unit itself imparts particular characteristics onto a biomolecule. In particular, protein PEGylation may lead to prolonged residence in vivo, decreased degradation by metabolic enzymes and a reduction or elimination of protein immunogenicity. Several PEGylated proteins have been FDA-approved and are currently on the market.

By virtue of its high polarity, PEG linkers are perfectly suitable for bioconjugation of small and/or water-soluble moieties under aqueous conditions. However, in case of conjugation of hydrophobic, non water-soluble molecules of interest, the polarity of a PEG unit may be insufficient to offset hydrophobicity, leading to significantly reduced reaction rates, lower yields and induced aggregation issues. In such case, lengthy PEG linkers and/or significant amounts of organic cosolvents may be required to solubilize the reagents. For example, in the field of antibody-drug conjugates, the controlled attachment of a distinct number of toxic payloads to a monoclonal antibody is key, with a payload typically selected from the group of auristatins E or F, maytansinoids, duocarmycins, calicheamicins or pyrrolobenzodiazepines (PBDs), with many others are underway. With the exception of auristatin F, all toxic payloads are poorly to non water-soluble, which necessitates organic cosolvents to achieve successful conjugation, such as 25% dimethylacetamide (DMA) or 50% propylene glycol (PG). In case of hydrophobic payloads, despite the use of aforementioned cosolvents, large stoichiometries of reagents may be required during conjugation while efficiency and yield may be significantly compromised due to aggregation (in process or after product isolation), as for example described by Senter et al. in *Nat. Biotechn.* 2014, 24, 1256-1263, incorporated by reference. The use of long PEG spacers (12 units or more) may partially enhance solubility and/or conjugation efficiency, but it has been shown that long PEG spacers may lead to more rapid in vivo clearance, and hence negatively influence the pharmacokinetic profile of the ADC.

From the above, it becomes clear that there is a demand for short, polar spacers that enable the fast and efficient conjugation of hydrophobic moieties. It is clear that the latter pertains even to a higher level on conjugation reactions where a hydrophobic reactive moiety is employed, such as for example strained alkynes, alkenes, and phosphines (see above).

Linkers are known in the art, and disclosed in e.g. WO 2008/070291, incorporated by reference. WO 2008/070291 discloses a linker for the coupling of targeting agents to anchoring components. The linker contains hydrophilic regions represented by polyethylene glycol (PEG) and an extension lacking chiral centers that is coupled to a targeting agent.

WO 01/88535, incorporated by reference, discloses a linker system for surfaces for bioconjugation, in particular a linker system having a novel hydrophilic spacer group. The hydrophilic atoms or groups for use in the linker system are selected from the group consisting of O, NH, C=O (keto group), O—C=O (ester group) and $CR^3R^4$, wherein $R^3$ and $R^4$ are independently selected from the group consisting of H, OH, $C_1$-$C_4$ alkoxy and $C_1$-$C_4$ acyloxy.

WO 2014/100762, incorporated by reference, describes compounds with a hydrophilic self-immolative linker, which is cleavable under appropriate conditions and incorporates a hydrophilic group to provide better solubility of the compound. The compounds comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. The hydrophilic self-immolative linker is e.g. a benzyloxycarbonyl group.

SUMMARY OF THE INVENTION

The invention relates to a compound (also referred to as a linker-conjugate) comprising an alpha-end and an omega-end, the compound comprising on the alpha-end a reactive group $Q^1$ capable of reacting with a functional group $F^1$ present on a biomolecule and on the omega-end a target molecule, the compound further comprising a group according to formula (1) or a salt thereof:

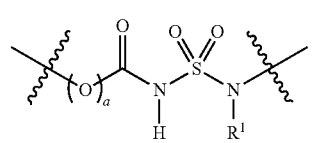

1 wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety;

and wherein the group according to formula (1), or the salt thereof, is situated in between said alpha-end and said omega-end of the compound.

More in particular, the invention relates to a linker-conjugate according to formula (4a) or (4b), or a salt thereof:

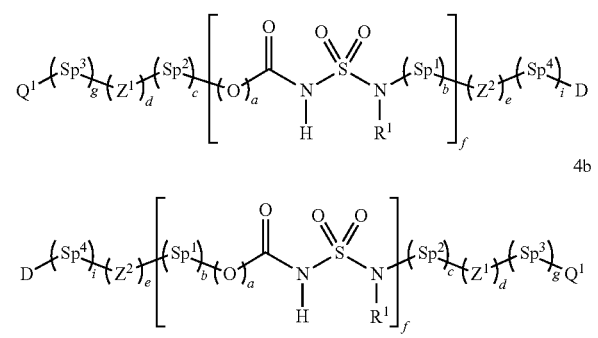

wherein:
a is independently 0 or 1;
b is independently 0 or 1;
c is 0 or 1;
d is 0 or 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or $N(R^1)$;
$Z^2$ is a connecting group that connects D or $Sp^4$ to $Sp^1$, $N(R^1)$, O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or
$R^1$ is D, -[$(Sp^1)_b$-$(Z^2)_e$—$(Sp^4)_i$-D] or -[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, Q1, b, c, d, e, g and i are as defined above.

The invention also relates to a process for the preparation of a bioconjugate, the process comprising the step of reacting a reactive group $Q^1$ of a linker-conjugate with a functional group $F^1$ of a biomolecule, wherein the linker-conjugate is a compound comprising an alpha-end and an omega-end, the compound comprising on the alpha-end a reactive group $Q^1$ capable of reacting with a functional group $F^1$ present on the biomolecule and on the omega-end a target molecule, the compound further comprising a group according to formula (1) or a salt thereof:

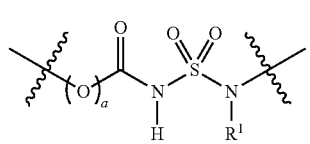

wherein a and $R^1$ are as defined above, and wherein the group according to formula (1), or the salt thereof, is situated in between said alpha-end and said omega-end of the compound.

More in particular, the invention relates to a process for the preparation of a bioconjugate, the process comprising the step of reacting a reactive group $Q^1$ of a linker-conjugate according to formula (4a) or (4b) as defined above, with a functional group $F^1$ of a biomolecule. In a preferred embodiment, the invention concerns a process for the preparation of a bioconjugate via a cycloaddition, such as a (4+2)-cycloaddition (e.g. a Diels-Alder reaction) or a (3+2)-cycloaddition (e.g. a 1,3-dipolar cycloaddition), preferably the 1,3-dipolar cycloaddition, more preferably the alkyne-azide cycloaddition, and most preferably wherein $Q^1$ is or comprises an alkyne group, such as a cycloalkyne group, and $F^1$ is an azido group. In a further preferred embodiment, the invention concerns a process for the preparation of a bioconjugate, wherein the target molecule is hydrophobic (i.e. weakly soluble in water), most preferably wherein the target molecule has a water solubility of at most 0.1% (w/w) in water (20° C. and 100 kPa). In an especially preferred embodiment, the invention concerns a process for the preparation of a bioconjugate via a cycloaddition, preferably a 1,3-dipolar cycloaddition, more preferably the alkyne-azide cycloaddition, and most preferably wherein $Q^1$ is or comprises an alkyne group and $F^1$ is an azido group, and wherein the target molecule is hydrophobic, most preferably wherein the target molecule has a water solubility of at most 0.1% (w/w) in water (20° C. and 100 kPa).

The invention further relates to a bioconjugate obtainable by the process according to the invention.

BRIEF DESCRIPTION OF THE FIGURES

FIG. 8 shows the structures of several compounds wherein a bicyclo[6.1.0]non-4-yn-9-yl] reactive group $Q^1$ (also referred to as a BCN group) is connected to maytansin via a linker unit.

DETAILED DESCRIPTION OF THE INVENTION

Definitions

Figure 1:
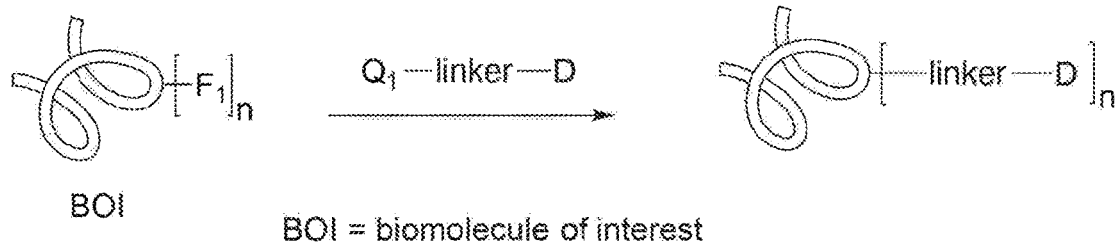
FIG. 1 describes the general concept of conjugation of biomolecules: a biomolecule of interest (BOI) containing one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent connection between the BOI and the MOI. The BOI may e.g. be a peptide/protein, a glycan or a nucleic acid.
Figure 1:
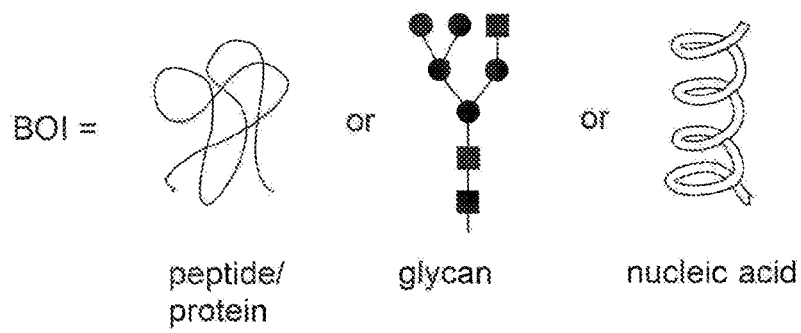

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

Unsubstituted alkyl groups have the general formula $C_nH_{2n+1}$ and may be linear or branched. Optionally, the alkyl groups are substituted by one or more substituents further specified in this document. Examples of alkyl groups include methyl, ethyl, propyl, 2-propyl, t-butyl, 1-hexyl, 1-dodecyl, etc.

A cycloalkyl group is a cyclic alkyl group. Unsubstituted cycloalkyl groups comprise at least three carbon atoms and have the general formula $C_nH_{2n-1}$. Optionally, the cycloalkyl groups are substituted by one or more substituents further specified in this document. Examples of cycloalkyl groups include cyclopropyl, cyclobutyl, cyclopentyl and cyclohexyl.

An alkenyl group comprises one or more carbon-carbon double bonds, and may be linear or branched. Unsubstituted alkenyl groups comprising one C—C double bond have the general formula $CnH_{2n-1}$. Unsubstituted alkenyl groups comprising two C—C double bonds have the general formula $CnH_{2n-3}$. An alkenyl group may comprise a terminal carbon-carbon double bond and/or an internal carbon-carbon double bond. A terminal alkenyl group is an alkenyl group wherein a carbon-carbon double bond is located at a terminal position of a carbon chain. An alkenyl group may also comprise two or more carbon-carbon double bonds. Examples of an alkenyl group include ethenyl, propenyl, isopropenyl, t-butenyl, 1,3-butadienyl, 1,3-pentadienyl, etc. Unless stated otherwise, an alkenyl group may optionally be substituted with one or more, independently selected, substituents as defined below. Unless stated otherwise, an alkenyl group may optionally be interrupted by one or more heteroatoms independently selected from the group consisting of O, N and S.

An alkynyl group comprises one or more carbon-carbon triple bonds, and may be linear or branched. Unsubstituted alkynyl groups comprising one C—C triple bond have the general formula $CnH_{2n-3}$. An alkynyl group may comprise a terminal carbon-carbon triple bond and/or an internal carbon-carbon triple bond. A terminal alkynyl group is an alkynyl group wherein a carbon-carbon triple bond is located at a terminal position of a carbon chain. An alkynyl group may also comprise two or more carbon-carbon triple bonds. Unless stated otherwise, an alkynyl group may optionally be substituted with one or more, independently selected, substituents as defined below. Examples of an alkynyl group include ethynyl, propynyl, isopropynyl, t-butynyl, etc. Unless stated otherwise, an alkynyl group may optionally be interrupted by one or more heteroatoms independently selected from the group consisting of O, N and S.

An aryl group comprises six to twelve carbon atoms and may include monocyclic and bicyclic structures. Optionally, the aryl group may be substituted by one or more substituents further specified in this document. Examples of aryl groups are phenyl and naphthyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

Heteroaryl groups comprise at least two carbon atoms (i.e. at least $C_2$) and one or more heteroatoms N, O, P or S. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, imidazolyl, thiazolyl, pyrrolyl, furanyl, triazolyl, benzofuranyl, indolyl, purinyl, benzoxazolyl, thienyl, phospholyl and oxazolyl.

Heteroarylalkyl groups and alkylheteroaryl groups comprise at least three carbon atoms (i.e. at least $C_3$) and may include monocyclic and bicyclic structures. Optionally, the heteroaryl groups may be substituted by one or more substituents further specified in this document.

Where an aryl group is denoted as a (hetero)aryl group, the notation is meant to include an aryl group and a heteroaryl group. Similarly, an alkyl(hetero)aryl group is meant to include an alkylaryl group and a alkylheteroaryl group, and (hetero)arylalkyl is meant to include an arylalkyl group and a heteroarylalkyl group. A $C_2$-$C_{24}$ (hetero)aryl group is thus to be interpreted as including a $C_2$-$C_{24}$ heteroaryl group and a $C_6$-$C_{24}$ aryl group. Similarly, a $C_3$-$C_{24}$ alkyl(hetero)aryl group is meant to include a $C_7$-$C_{24}$ alkylaryl group and a $C_3$-$C_{24}$ alkylheteroaryl group, and a $C_3$-$C_{24}$ (hetero)arylalkyl is meant to include a $C_7$-$C_{24}$ arylalkyl group and a $C_3$-$C_{24}$ heteroarylalkyl group.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero)cycloalkyne compounds, i.e. (hetero)cycloalkyne compounds wherein a second ring structure is fused, i.e. annulated, to the (hetero)cycloalkynyl group. For example in a fused (hetero)cyclooctyne compound, a cycloalkyl (e.g. a cyclopropyl) or an arene (e.g. benzene) may be annulated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

Unless stated otherwise, alkyl groups, cycloalkyl groups, alkenyl groups, alkynyl groups, (hetero)aryl groups, (hetero)arylalkyl groups, alkyl(hetero)aryl groups, alkylene groups, alkenylene groups, alkynylene groups, cycloalkylene groups, cycloalkenylene groups, cycloalkynylene groups, (hetero)arylene groups, alkyl(hetero)arylene groups, (hetero)arylalkylene groups, (hetero)arylalkenylene groups, (hetero)arylalkynylene groups, alkenyl groups, alkoxy groups, alkenyloxy groups, (hetero)aryloxy groups, alkynyloxy groups and cycloalkyloxy groups may be substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^{20})_3Si$—, wherein $R^{20}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine ($GlcNH_2$), galactosamine ($GalNH_2$)N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA).

The term "nucleotide" is herein used in its normal scientific meaning. The term "nucleotide" refers to a molecule that is composed of a nucleobase, a five-carbon sugar (either ribose or 2-deoxyribose), and one, two or three phosphate groups. Without the phosphate group, the nucleobase and sugar compose a nucleoside. A nucleotide can thus also be called a nucleoside monophosphate, a nucleoside diphosphate or a nucleoside triphosphate. The nucleobase may be adenine, guanine, cytosine, uracil or thymine. Examples of a nucleotide include uridine diphosphate (UDP), guanosine diphosphate (GDP), thymidine diphosphate (TDP), cytidine diphosphate (CDP) and cytidine monophosphate (CMP).

The term "protein" is herein used in its normal scientific meaning. Herein, polypeptides comprising about 10 or more amino acids are considered proteins. A protein may comprise natural, but also unnatural amino acids.

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (candida antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched.

In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, F(ab')$_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab-I131, cetuximab, ibritumomab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab. A linker is herein defined as a moiety that connects two or more elements of a compound. For example in a bioconjugate, a biomolecule and a target molecule are covalently connected to each other via a linker; in a linker-conjugate a reactive group $Q^1$ is covalently connected to a target molecule via a linker; in a linker-construct a reactive group $Q^1$ is covalently connected to a reactive group $Q^2$ via a linker. A linker may comprise one or more spacer-moieties.

A spacer-moiety is herein defined as a moiety that spaces (i.e. provides distance between) and covalently links together two (or more) parts of a linker. The linker may be part of e.g. a linker-construct, a linker-conjugate or a bioconjugate, as defined below.

A linker-construct is herein defined as a compound wherein a reactive group $Q^1$ is covalently connected to a reactive group $Q^2$ via a linker. A linker-construct comprises a reactive group $Q^1$ capable of reacting with a reactive group present on a biomolecule, and a reactive group $Q^2$ capable of reacting with a reactive group present on a target molecule. $Q^1$ and $Q^2$ may be the same, or different. A linker-construct may also comprise more than one reactive group $Q^1$ and/or more than one reactive group $Q^2$. A linker-construct may also be denoted as $Q^1$-Sp-$Q^2$, wherein $Q^1$ is a reactive group capable of reacting with a reactive group $F^1$ present on a biomolecule, $Q^2$ is a reactive group capable of reacting with a reactive group $F^2$ present on a target molecule and Sp is a spacer moiety. When a linker-construct comprises more than one reactive group $Q^1$ and/or more than one reactive group $Q^2$, the linker-construct may be denoted as $(Q^1$-Sp-$(Q^2)_z)_y$, wherein y is an integer in the range of 1 to 10 and z is an integer in the range of 1 to 10. Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1.

A linker-conjugate is herein defined as a compound wherein a target molecule is covalently connected to a reactive group $Q^1$, via a linker. A linker-conjugate may be obtained via reaction of a reactive group $Q^2$ present on a linker-construct with a reactive group present on a target molecule. A linker-conjugate comprises a reactive group $Q^1$ that is capable of reacting with a reactive group present on a biomolecule. A linker-conjugate may comprise one or more spacer moieties. A linker-conjugate may comprise more than one reactive groups $Q^1$ and/or more than one target molecules.

A bioconjugate is herein defined as a compound wherein a biomolecule is covalently connected to a target molecule via a linker. A bioconjugate comprises one or more biomolecules and/or one or more target molecules. The linker may comprise one or more spacer moieties.

When a compound is herein referred to as a compound comprising an alpha-end and an omega-end, said compound comprises two (or more) ends, the first end being referred to as the alpha-end and the second end being referred to as the omega-end.

Said compound may comprise more than two ends, i.e. a third, fourth etc. end may be present in the compound.

A biomolecule is herein defined as any molecule that can be isolated from Nature or any molecule composed of smaller molecular building blocks that are the constituents of macromolecular structures derived from Nature, in particular nucleic acids, proteins, glycans and lipids. Examples of a biomolecule include an enzyme, a (non-catalytic) protein, a polypeptide, a peptide, an amino acid, an oligonucleotide, a monosaccharide, an oligosaccharide, a polysaccharide, a glycan, a lipid and a hormone.

A target molecule, also referred to as a molecule of interest (MOI), is herein defined as molecular structure possessing a desired property that is imparted onto the biomolecule upon conjugation.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt.

The term "pharmaceutically accepted" salt means a salt that is acceptable for administration to a patient, such as a mammal (salts with counterions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

Linker-Conjugate

Herein, a sulfamide linker and conjugates of said sulfamide linker are disclosed. The term "sulfamide linker" refers to a linker comprising a sulfamide group, more particularly an acylsulfamide group [—C(O)—N(H)—S(O)$_2$—N(R$^1$)-] and/or a carbamoyl sulfamide group [—O—C(O)—N(H)—S(O)$_2$—N(R$^1$)—].

The present invention relates to the use of a sulfamide linker according to the invention in a process for the preparation of a bioconjugate. The invention further relates to a process for the preparation of a bioconjugate and to a bioconjugate obtainable by said process. Said process for the preparation of a bioconjugate is described in more detail below.

In a first aspect, the present invention relates to a compound comprising an alpha-end and an omega-end, the compound comprising on the alpha-end a reactive group Q$^1$ capable of reacting with a functional group F$^1$ present on a biomolecule and on the omega-end a target molecule D, the compound further comprising a group according to formula (1) or a salt thereof:

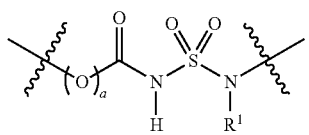

wherein:
a is 0 or 1; and
R$^1$ is selected from the group consisting of hydrogen, C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups, the C$_1$-C$_{24}$ alkyl groups, C$_3$-C$_{24}$ cycloalkyl groups, C$_2$-C$_{24}$ (hetero)aryl groups, C$_3$-C$_{24}$ alkyl(hetero)aryl groups and C$_3$-C$_{24}$ (hetero)arylalkyl groups optionally substituted and optionally interrupted by one or more heteroatoms selected from O, S and NR$^3$ wherein R$^3$ is independently selected from the group consisting of hydrogen and C$_1$-C$_4$ alkyl groups, or R$^1$ is a target molecule D, wherein the target molecule is optionally connected to N via a spacer moiety;
and wherein the group according to formula (1), or the salt thereof, is situated in between said alpha-end and said omega-end of the compound.

Said compound is also referred to as a linker-conjugate. A linker-conjugate is herein defined as a compound wherein a target molecule is covalently connected to a reactive group Q$^1$, via a linker. The compound comprises an alpha-end and an omega-end, in other words, the compound comprises a first end and a second end. The first end of the compound may also be referred to as an alpha-end, and the second end may also be referred to as an omego-end of the compound. The terms "alpha-end" and "omega-end" are known to a person skilled in the art. The invention thus also relates to a compound comprising a first end and a second end, the compound comprising on the first end a reactive group Q$^1$ capable of reacting with a functional group F$^1$ present on a biomolecule and on the second end a target molecule D, the compound further comprising a group according to formula (1) or a salt thereof, wherein the group according to formula (1), or the salt thereof, is situated in between said first end and said second end of the compound, and wherein the group according to formula (1) is as defined above.

In the compound according to invention, the group according to formula (1), or the salt thereof, is situated in between said alpha-end and said omega-end of the compound. Reactive group Q$^1$ is covalently bonded to the alpha-end of the compound, and target molecule D is covalently bonded to an omega-end of the compound.

The compound according to the invention may also be referred to as a linker-conjugate. In the linker-conjugate according to the invention, a target molecule D is covalently attached to a reactive group Q$^1$ via a linker, and said linker comprises a group according to formula (1), or a salt thereof, as defined above.

When the linker-conjugate according to the invention comprises a salt of the group according to formula (1), the salt is preferably a pharmaceutically acceptable salt.

The linker-conjugate according to the invention may comprise more than one target molecule D. Consequently, the linker-conjugate may thus comprise more than one omega-end, e.g. a second (third, fourth, fifth, etc.) omega-end, the second (third, fourth, fifth, etc.) omega-end may be covalently attached to a target molecule. Similarly, the linker-conjugate may comprise more than one reactive group Q$^1$, i.e. the linker-conjugate may comprise more than one alpha-end. When more than one reactive group Q$^1$ is present the groups Q$^1$ may be the same or different, and when more than one target molecule D is present the target molecules D may be the same or different.

The linker-conjugate according to the invention may therefore also be denoted as (Q$^1$)$_y$-Sp-(D)$_z$, wherein y is an integer in the range of 1 to 10 and z is an integer in the range of 1 to 10.

The invention thus also relates to a compound according to the formula:

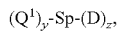

wherein:
y is an integer in the range of 1 to 10;
z is an integer in the range of 1 to 10;
Q$^1$ is a reactive group capable of reacting with a functional group F$^1$ present on a biomolecule;
D is a target molecule;
Sp is a spacer moiety, wherein a spacer moiety is defined as a moiety that spaces (i.e. provides a certain distance between) and covalently links reactive group Q$^1$ and target molecule D; and
wherein said spacer moiety comprises a group according to Formula (1) or a salt thereof, wherein the group according to Formula (1) is as defined above.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the linker-conjugate is according to the formula Q$^1$-Sp-(D)$_4$, Q$^1$-Sp-(D)$_3$, Q$^1$-Sp-(D)$_2$ or Q$^1$-Sp-D.

The linker-conjugate according to the invention comprises a group according to formula (1) as defined above, or a salt thereof. In a preferred embodiment, the linker-conjugate according to the invention comprises a group according to formula (1) wherein a is 0, or a salt thereof. In this embodiment, the compound thus comprises a group according to formula (2) or a salt thereof:

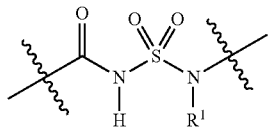

(2)

wherein R¹ is as defined above.

In another preferred embodiment, the linker-conjugate according to the invention comprises a group according to formula (1) wherein a is 1, or a salt thereof. In this embodiment, the linker-conjugate thus comprises a group according to formula (3) or a salt thereof:

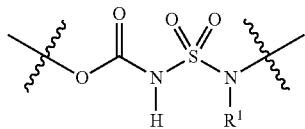

(3)

wherein R¹ is as defined above.

In the groups according to formula (1), (2) and (3), R¹ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety;

In a preferred embodiment, R¹ is hydrogen or a $C_1$-$C_{20}$ alkyl group, more preferably R¹ is hydrogen or a $C_1$-$C_{16}$ alkyl group, even more preferably R¹ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a preferred embodiment, R¹ is hydrogen. In another preferred embodiment, R¹ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that R¹ is a (poly)ethyleneglycol chain comprising a terminal —OH group. In another preferred embodiment, R¹ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably R¹ is hydrogen or methyl, and most preferably R¹ is hydrogen.

In another preferred embodiment, R¹ is a target molecule D. Optionally, the target molecule D is connected to N via one or more spacer-moieties. The spacer-moiety, if present, is defined as a moiety that spaces, i.e. provides a certain distance between, and covalently links target molecule D and N. The target molecule D and preferred embodiments thereof are described in more detail below.

When the linker-conjugate according to the invention comprises two or more target molecules D, the target molecules D may differ from each other.

In a preferred embodiment of the linker-conjugate according to the invention, the target molecule is selected from the group consisting of an active substance, a reporter molecule, a polymer, a solid surface, a hydrogel, a nanoparticle, a microparticle and a biomolecule.

The inventors found that the use of a sulfamide linker according to the invention improves the solubility of the linker-conjugate, which in turn significantly improves the efficacy of the conjugation. Using conventional linkers, effective conjugation is often hampered by the relatively low soubility of the linker-conjugate in aqueous media, especially when a relative water-insoluble or hydrophobic target molecule is used. In a particularly preferred embodiment, the target molecule in its unconjugated form is hydrophobic, typically having a water solubility of at most 1% (w/w), preferably at most 0.1% (w/w), most preferably at most 0.01% (w/w), determined at 20° C. and 100 kPa. Even such water-insoluble target molecules are effectively subjected to conjugation when functionalized with a sulfamide linker according to the invention. Herein, the "unconjugated form" refers to the target molecule not being functionalized with or conjugated to the linker according to the invention. Such unconjugated forms of target molecules are known to the skilled person.

The term "active substance" herein relates to a pharmacological and/or biological substance, i.e. a substance that is biologically and/or pharmaceutically active, for example a drug, a prodrug, a diagnostic agent, a protein, a peptide, a polypeptide, a peptide tag, an amino acid, a glycan, a lipid, a vitamin, a steroid, a nucleotide, a nucleoside, a polynucleotide, RNA or DNA. Examples of peptide tags include cell-penetrating peptides like human lactoferrin or polyarginine. An example of a glycan is oligomannose. An example of an amino acid is lysine.

When the target molecule is an active substance, the active substance is preferably selected from the group consisting of drugs and prodrugs. More preferably, the active substance is selected from the group consisting of pharmaceutically active compounds, in particular low to medium molecular weight compounds (e.g. about 200 to about 2500 Da, preferably about 300 to about 1750 Da). In a further preferred embodiment, the active substance is selected from the group consisting of cytotoxins, antiviral agents, antibacterials agents, peptides and oligonucleotides. Examples of cytotoxins include colchicine, vinca alkaloids, anthracyclines, camptothecins, doxorubicin, daunorubicin, taxanes, calicheamycins, tubulysins, irinotecans, an inhibitory peptide, amanitin, deBouganin, duocarmycins, maytansines, auristatins or pyrrolobenzodiazepines (PBDs). In view of their poor water solubility, preferred active substances include vinca alkaloids, anthracyclines, camptothecins, taxanes, tubulysins, amanitin, duocarmycins, maytansines, auristatins and pyrrolobenzodiazepines, in particular vinca alkaloids, anthracyclines, camptothecins, taxanes, tubulysins, amanitin, maytansines and auristatins.

The term "reporter molecule" herein refers to a molecule whose presence is readily detected, for example a diagnostic agent, a dye, a fluorophore, a radioactive isotope label, a contrast agent, a magnetic resonance imaging agent or a mass label.

A wide variety of fluorophores, also referred to as fluorescent probes, is known to a person skilled in the art. Several fluorophores are described in more detail in e.g. G. T. Hermanson, "*Bioconjugate Techniques*", Elsevier, 3$^{rd}$ Ed. 2013, Chapter 10: "*Fluorescent probes*", p. 395-463, incorporated by reference. Examples of a fluorophore include all kinds of Alexa Fluor (e.g. Alexa Fluor 555), cyanine dyes (e.g. Cy3 or Cy5) and cyanine dye derivatives, coumarin derivatives, fluorescein and fluorescein derivatives, rhodamine and rhodamine derivatives, boron dipyrromethene derivatives, pyrene derivatives, naphthalimide derivatives, phycobiliprotein derivatives (e.g. allophycocyanin), chromomycin, lanthanide chelates and quantum dot nanocrystals. In view of their poor water solubility, preferred fluorophores include cyanine dyes, coumarin derivatives, fluorescein and derivatives thereof, pyrene derivatives, naphthalimide derivatives, chromomycin, lanthanide chelates and quantum dot nanocrystals, in particular coumarin derivatives, fluorescein, pyrene derivatives and chromomycin.

Examples of a radioactive isotope label include $^{99m}$Tc, $^{111}$In, $^{114m}$In, $^{115}$In, $^{18}$F, $^{14}$C, $^{64}$Cu, $^{131}$I, $^{125}$I, $^{123}$I, $^{212}$Bi, $^{88}$Y, $^{90}$Y, $^{67}$Cu, $^{186}$Rh, $^{188}$Rh, $^{66}$Ga, $^{67}$Ga and $^{10}$B, which is optionally connected via a chelating moiety such as e.g. DTPA (diethylenetriaminepentaacetic anhydride), DOTA (1,4,7,10-tetraazacyclododecane-N,N',N'',N'''-tetraacetic acid), NOTA (1,4,7-triazacyclononane N,N',N''-triacetic acid), TETA (1,4,8,11-tetraazacyclotetradecane-N,N',N'', N'''-tetraacetic acid), DTTA (N$^1$-(p-isothiocyanatobenzyl)-diethylenetriamine-N$^1$,N$^2$,N$^3$,N$^3$-tetraacetic acid), deferoxamine or DFA (N'-[5-[[4-[[5-(acetylhydroxyamino)pentyl] amino]-1,4-dioxobutyl]hydroxy-amino]pentyl]-N-(5-aminopentyl)-N-hydroxybutanediamide) or HYNIC (hydrazino-nicotinarnide). Isotopic labelling techniques are known to a person skilled in the art, and are described in more detail in e.g. G. T. Hermanson, "*Bioconjugate Techniques*", Elsevier, 3$^{rd}$ Ed. 2013, Chapter 12: "*Isotopic labelling techniques*", p. 507-534, incorporated by reference.

Polymers suitable for use as a target molecule D in the compound according to the invention are known to a person skilled in the art, and several examples are described in more detail in e.g. G. T. Hermanson, "*Bioconjugate Techniques*", Elsevier, 3$^{rd}$ Ed. 2013, Chapter 18: "*PEGylation and synthetic polymer modification*", p. 787-838, incorporated by reference. When target molecule D is a polymer, target molecule D is preferably independently selected from the group consisting of a poly(ethyleneglycol) (PEG), a polyethylene oxide (PEO), a polypropylene glycol (PPG), a polypropylene oxide (PPO), a 1,x-diaminoalkane polymer (wherein x is the number of carbon atoms in the alkane, and preferably x is an integer in the range of 2 to 200, preferably 2 to 10), a (poly)ethylene glycol diamine (e.g. 1,8-diamino-3,6-dioxaoctane and equivalents comprising longer ethylene glycol chains), a polysaccharide (e.g. dextran), a poly(amino acid) (e.g. a poly(L-lysine)) and a poly(vinyl alcohol). In view of their poor water solubility, preferred polymers include a 1,x-diaminoalkane polymer and poly(vinyl alcohol).

Solid surfaces suitable for use as a target molecule D are known to a person skilled in the art. A solid surface is for example a functional surface (e.g. a surface of a nanomaterial, a carbon nanotube, a fullerene or a virus capsid), a metal surface (e.g. a titanium, gold, silver, copper, nickel, tin, rhodium or zinc surface), a metal alloy surface (wherein the alloy is from e.g. aluminium, bismuth, chromium, cobalt, copper, gallium, gold, indium, iron, lead, magnesium, mercury, nickel, potassium, plutonium, rhodium, scandium, silver, sodium, titanium, tin, uranium, zinc and/or zirconium), a polymer surface (wherein the polymer is e.g. polystyrene, polyvinylchloride, polyethylene, polypropylene, poly(dimethylsiloxane) or polymethylmethacrylate, polyacrylamide), a glass surface, a silicone surface, a chromatography support surface (wherein the chromatography support is e.g. a silica support, an agarose support, a cellulose support or an alumina support), etc. When target molecule D is a solid surface, it is preferred that D is independently selected from the group consisting of a functional surface or a polymer surface.

Hydrogels are known to the person skilled in the art. Hydrogels are water-swollen networks, formed by cross-links between the polymeric constituents. See for example A. S. Hoffman, *Adv. Drug Delivery Rev.* 2012, 64, 18, incorporated by reference. When the target molecule is a hydrogel, it is preferred that the hydrogel is composed of poly(ethylene)glycol (PEG) as the polymeric basis.

Micro- and nanoparticles suitable for use as a target molecule D are known to a person skilled in the art. A variety of suitable micro- and nanoparticles is described in e.g. G. T. Hermanson, "*Bioconjugate Techniques*", Elsevier, 3$^{rd}$ Ed. 2013, Chapter 14: "*Microparticles and nanoparticles*", p. 549-587, incorporated by reference. The micro- or nanoparticles may be of any shape, e.g. spheres, rods, tubes, cubes, triangles and cones. Preferably, the micro- or nanoparticles are of a spherical shape. The chemical composition of the micro- and nanoparticles may vary. When target molecule D is a micro- or a nanoparticle, the micro- or nanoparticle is for example a polymeric micro- or nanoparticle, a silica micro- or nanoparticle or a gold micro- or nanoparticle.

When the particle is a polymeric micro- or nanoparticle, the polymer is preferably polystyrene or a copolymer of styrene (e.g. a copolymer of styrene and divinylbenzene, butadiene, acrylate and/or vinyltoluene), polymethylmethacrylate (PMMA), polyvinyltoluene, poly(hydroxyethyl methacrylate (pHEMA) or poly(ethylene glycol dimethacrylate/2-hydroxyethylmetacrylae) [poly(EDGMA/HEMA)]. Optionally, the surface of the micro- or nanoparticles is modified, e.g. with detergents, by graft polymerization of secondary polymers or by covalent attachment of another polymer or of spacer moieties, etc.

Target molecule D may also be a biomolecule. Biomolecules, and preferred embodiments thereof, are described in more detail below. When target molecule D is a biomolecule, it is preferred that the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides.

The linker-conjugate according to the invention comprises a reactive group Q$^1$ that is capable of reacting with a functional group F$^1$ present on a biomolecule. Functional groups are known to a person skilled in the art and may be defined as any molecular entity that imparts a specific property onto the molecule harbouring it. For example, a functional group in a biomolecule may constitute an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne or a phosphine moiety. Herein, the term "reactive group" may refer to a certain group that comprises a functional group, but also to a functional group itself. For example, a cyclooctynyl group is a reactive group comprising a functional group, namely a C—C triple bond. Similarly, an N-maleimidyl group is a reactive group, comprising a C—C double bond as a functional group. However, a functional group, for example an azido functional group, a thiol functional group or an amino functional group, may herein also be referred to as a reactive group.

The linker-conjugate may comprise more than one reactive group $Q^1$. When the linker-conjugate comprises two or more reactive groups $Q^1$, the reactive groups $Q^1$ may differ from each other. Preferably, the linker-conjugate comprises one reactive group $Q^1$.

Reactive group $Q^1$ that is present in the linker-conjugate, is able to react with a functional group $F^1$ that is present in a biomolecule. In other words, reactive group $Q^1$ needs to be complementary to a functional group $F^1$ present in a biomolecule. Herein, a reactive group is denoted as "complementary" to a functional group when said reactive group reacts with said functional group selectively, optionally in the presence of other functional groups. Complementary reactive and functional groups are known to a person skilled in the art, and are described in more detail below.

In a preferred embodiment, reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)-methylcarbonyl groups or elimination derivatives thereof, carbonyl halide groups, allenamide groups, 1,2-quinone groups or triazine groups.

In a preferred embodiment, $Q^1$ is an N-maleimidyl group. When $Q^1$ is an N-maleimidyl group, $Q^1$ is preferably unsubstituted. $Q^1$ is thus preferably according to formula (9a), as shown below.

In another preferred embodiment, $Q^1$ is a halogenated N-alkylamido group. When $Q^1$ is a halogenated N-alkylamido group, it is preferred that $Q^1$ is according to formula (9b), as shown below, wherein k is an integer in the range of 1 to 10 and $R^4$ is selected from the group consisting of —Cl, —Br and —I. Preferably k is 1, 2, 3 or 4, more preferably k is 1 or 2 and most preferably k is 1. Preferably, $R^4$ is —I or —Br. More preferably, k is 1 or 2 and $R^4$ is —I or —Br, and most preferably k is 1 and $R^4$ is —I or Br.

In another preferred embodiment, $Q^1$ is a sulfonyloxy N-alkylamido group. When $Q^1$ is a sulfonyloxy N-alkylamido group, it is preferred that $Q^1$ is according to formula (9b), as shown below, wherein k is an integer in the range of 1 to 10 and $R^4$ is selected from the group consisting of —O-mesyl, —O-phenylsulfonyl and —O-tosyl. Preferably k is 1, 2, 3 or 4, more preferably k is 1 or 2, even more preferably k is 1. Most preferably k is 1 and $R^4$ is selected from the group consisting of —O-mesyl, —O-phenylsulfonyl and —O-tosyl.

In another preferred embodiment, $Q^1$ is an ester group. When $Q^1$ is an ester group, it is preferred that the ester group is an activated ester group. Activated ester groups are known to the person skilled in the art. An activated ester group is herein defined as an ester group comprising a good leaving group, wherein the ester carbonyl group is bonded to said good leaving group. Good leaving groups are known to the person skilled in the art. It is further preferred that the activated ester is according to formula (9c), as shown below, wherein $R^5$ is selected from the group consisting of —N— succinimidyl (NHS), —N-sulfo-succinimidyl (sulfo-NHS), -(4-nitrophenyl), -pentafluorophenyl or -tetrafluorophenyl (TFP).

In another preferred embodiment, $Q^1$ is a carbonate group. When $Q^1$ is a carbonate group, it is preferred that the carbonate group is an activated carbonate group. Activated carbonate groups are known to a person skilled in the art. An activated carbonate group is herein defined as a carbonate group comprising a good leaving group, wherein the carbonate carbonyl group is bonded to said good leaving group. It is further preferred that the carbonate group is according to formula (9d), as shown below, wherein $R^7$ is selected from the group consisting of —N-succinimidyl, —N-sulfo-succinimidyl, -(4-nitrophenyl), -pentafluorophenyl or -tetrafluorophenyl.

In another preferred embodiment, $Q^1$ is a sulfonyl halide group according to formula (9e) as shown below, wherein X is selected from the group consisting of F, Cl, Br and I. Preferably X is Cl or Br, more preferably Cl.

In another preferred embodiment, $Q^1$ is a thiol group (9f), or a derivative or a precursor of a thiol group. A thiol group may also be referred to as a mercapto group. When $Q^1$ is a derivative or a precursor of a thiol group, the thiol derivative is preferably according to formula (9g), (9h) or (9zb) as shown below, wherein $R^8$ is an, optionally substituted, $C_1$-$C_{12}$ alkyl group or a $C_2$-$C_{12}$ (hetero)aryl group, V is O or S and $R^{16}$ is an, optionally substituted, $C_1$-$C_{12}$ alkyl group. More preferably $R^8$ is an, optionally substituted, $C_1$-$C_6$ alkyl group or a $C_2$-$C_6$ (hetero)aryl group, and even more preferably $R^8$ is methyl, ethyl, n-propyl, i-propyl, n-butyl, s-butyl, t-butyl or phenyl. Even more preferably, $R^8$ is methyl or phenyl, most preferably methyl. More preferably $R^{16}$ is an optionally substituted $C_1$-$C_6$ alkyl group, and even more preferably $R^{16}$ is methyl, ethyl, n-propyl, i-propyl, n-butyl, s-butyl or t-butyl, most preferably methyl. When $Q^1$ is a thiol-derivative according to formula (9g) or (9zb), and $Q^1$ is reacted with a reactive group $F^1$ on a biomolecule, said thiol-derivative is converted to a thiol group during the process. When $Q^1$ is according to formula (9h), $Q^1$ is —SC(O)OR$^8$ or —SC(S)OR$^8$, preferably SC(O)OR$^8$, wherein $R^8$, and preferred embodiments thereof, are as defined above.

In another preferred embodiment, $Q^1$ is an alkenyl group, wherein the alkenyl group is linear or branched, and wherein the alkenyl group is optionally substituted. The alkenyl group may be a terminal or an internal alkenyl group. The alkenyl group may comprise more than one C—C double bond, and if so, preferably comprises two C—C double bonds. When the alkenyl group is a dienyl group, it is further preferred that the two C—C double bonds are separated by one C—C single bond (i.e. it is preferred that the dienyl group is a conjugated dienyl group). Preferably said alkenyl group is a $C_2$-$C_{24}$ alkenyl group, more preferably a $C_2$-$C_{12}$ alkenyl group, and even more preferably a $C_2$-$C_6$ alkenyl group. It is further preferred that the alkenyl group is a terminal alkenyl group. More preferably, the alkenyl group is according to formula (9i) as shown below, wherein l is an integer in the range of 0 to 10, preferably in the range of 0 to 6, and p is an integer in the range of 0 to 10, preferably 0 to 6. More preferably, l is 0, 1, 2, 3 or 4, more preferably l is 0, 1 or 2 and most preferably l is 0 or 1. More preferably, p is 0, 1, 2, 3 or 4, more preferably p is 0, 1 or 2 and most preferably p is 0 or 1. It is particularly preferred that p is 0 and 1 is 0 or 1, or that p is 1 and 1 is 0 or 1.

In another preferred embodiment, $Q^1$ is an alkynyl group, wherein the alkynyl group is linear or branched, and wherein the alkynyl group is optionally substituted. The alkynyl group may be a terminal or an internal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. It is further preferred that the alkynyl group is a terminal alkynyl group. More preferably, the alkynyl group is according to formula (9j) as shown below, wherein 1 is an integer in the range of 0 to 10, preferably in the range of 0 to 6. More preferably, 1 is 0, 1, 2, 3 or 4, more preferably 1 is 0, 1 or 2 and most preferably 1 is 0 or 1.

In another preferred embodiment, $Q^1$ is a cycloalkenyl group. The cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_8$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to formula (9zi) or (9zj) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to formula (9k), (9l), (9m) or (9zc) as shown below, wherein T is $CH_2$ or O, $R^9$ is independently selected from the group consisting of hydrogen, a linear or branched $C_1$-$C_{12}$ alkyl group or a $C_4$-$C_{12}$ (hetero)aryl group, and $R^{19}$ is selected from the group consisting of hydrogen and fluorinated hydrocarbons. Preferably, $R^9$ is independently hydrogen or a $C_1$-$C_6$ alkyl group, more preferably $R^9$ is independently hydrogen or a $C_1$-$C_4$ alkyl group. Even more preferably $R^9$ is independently hydrogen or methyl, ethyl, n-propyl, i-propyl, n-butyl, s-butyl or t-butyl. Yet even more preferably $R^9$ is independently hydrogen or methyl. In a further preferred embodiment, $R^{19}$ is selected from the group of hydrogen and —$CF_3$, —$C_2F_5$, —$C_3F_7$ and —$C_4F_9$, more preferably hydrogen and —$CF_3$. In a further preferred embodiment, the cycloalkenyl group is according to formula (9k), wherein one $R^9$ is hydrogen and the other $R_9$ is a methyl group. In another further preferred embodiment, the cycloalkenyl group is according to formula (9l), wherein both $R^9$ are hydrogen. In these embodiments it is further preferred that 1 is 0 or 1. In another further preferred embodiment, the cycloalkenyl group is a norbornenyl (T is $CH_2$) or an oxanorbornenyl (T is O) group according to formula (9m), or a norbornadienyl (T is $CH_2$) or an oxanorbornadienyl (T is O) group according to formula (9zc), wherein $R^9$ is hydrogen and $R^{19}$ is hydrogen or —$CF_3$, preferably —$CF_3$.

In another preferred embodiment, $Q^1$ is a (hetero)cycloalkynyl group. The (hetero)cycloalkynyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. In a further preferred embodiment, the (hetero)cyclooctynyl group is according to formula (9n), also referred to as a DIBO group, (9o), also referred to as a DIBAC group or (9p), also referred to as a BARAC group, or (9zk), also referred to as a COMBO group, all as shown below, wherein U is O or $NR^9$, and preferred embodiments of $R^9$ are as defined above. The aromatic rings in (9n) are optionally O-sulfonylated at one or more positions, whereas the rings of (9o) and (9p) may be halogenated at one or more positions.

In an especially preferred embodiment, the nitrogen atom attached to $R^1$ in compound (4b) is the nitrogen atom in the ring of the heterocycloalkyne group such as the nitrogen atom in 9o. In other words, c, d and g are 0 in compound (4b) and $R^1$ and $Q^1$, together with the nitrogen atom they are attached to, form a heterocycloalkyne group, preferably a heterocyclooctyne group, most preferably the heterocyclooctyne group according to formula (9o) or (9p). Herein, the carbonyl moiety of (9o) is replaced by the sulfonyl group of the group according to formula (1). Alternatively, the nitrogen atom to which $R^1$ is attached is the same atom as the atom designated as U in formula (9n). In other words, when $Q^1$ is according to formula (9n), U may be the right nitrogen atom of the group according to formula (1), or U=$NR^9$ and $R^9$ is the remainder of the group according to formula (1) and $R^1$ is the cyclooctyne moiety.

In another preferred embodiment, $Q^1$ is an, optionally substituted, bicyclo[6.1.0]non-4-yn-9-yl] group, also referred to as a BCN group. Preferably, the bicyclo[6.1.0] non-4-yn-9-yl] group is according to formula (9q) as shown below.

In another preferred embodiment, $Q^1$ is a conjugated (hetero)diene group capable of reacting in a Diels-Alder reaction. Preferred (hetero)diene groups include optionally substituted tetrazinyl groups, optionally substituted 1,2-quinone groups and optionally substituted triazine groups. More preferably, said tetrazinyl group is according to formula (9r), as shown below, wherein $R^9$ is selected from the group consisting of hydrogen, a linear or branched $C_1$-$C_{12}$ alkyl group or a $C_4$-$C_{12}$ (hetero)aryl group. Preferably, $R^9$ is hydrogen, a $C_1$-$C_6$ alkyl group or a $C_4$-$C_{10}$ (hetero)aryl group, more preferably $R^9$ is hydrogen, a $C_1$-$C_4$ alkyl group or a $C_4$-$C_6$ (hetero)aryl group. Even more preferably $R^9$ is hydrogen, methyl, ethyl, n-propyl, i-propyl, n-butyl, s-butyl, t-butyl or pyridyl. Yet even more preferably $R^9$ is hydrogen, methyl or pyridyl. More preferably, said 1,2-quinone group is according to formula (9zl) or (9zm). Said triazine group may be any regioisomer. More preferably, said triazine group is a 1,2,3-triazine group or a 1,2,4-triazine group, which may be attached via any possible location, such as indicated in formula (9zn). The 1,2,3-triazine is most preferred as triazine group.

In another preferred embodiment, $Q^1$ is an azido group according to formula (9s) as shown below.

In another preferred embodiment, $Q^1$ is an, optionally substituted, triarylphosphine group that is suitable to undergo a Staudinger ligation reaction. Preferably, the phosphine group is according to formula (9t) as shown below, wherein $R^{10}$ is hydrogen or a (thio)ester group. When $R^{10}$ is a (thio)ester group, it is preferred that $R^{10}$ is —C(O)—V—$R^{11}$, wherein V is O or S and $R^{11}$ is a $C_1$-$C_{12}$ alkyl group. Preferably, $R^{11}$ is a $C_1$-$C_6$ alkyl group, more preferably a $C_1$-$C_4$ alkyl group. Most preferably, $R^{11}$ is a methyl group.

In another preferred embodiment, $Q^1$ is a nitrile oxide group according to formula (9u) as shown below.

In another preferred embodiment, $Q^1$ is a nitrone group. Preferably, the nitrone group is according to formula (9v) as shown below, wherein $R^{12}$ is selected from the group consisting of linear or branched $C_1$-$C_{12}$ alkyl groups and $C_6$-$C_{12}$ aryl groups. Preferably, $R^{12}$ is a $C_1$-$C_6$ alkyl group, more preferably R$^{12}$ is a C$_1$-C$_4$ alkyl group. Even more preferably R$^{12}$ is methyl, ethyl, n-propyl, i-propyl, n-butyl, s-butyl or t-butyl. Yet even more preferably R$^{12}$ is methyl.

In another preferred embodiment, Q$^1$ is a nitrile imine group. Preferably, the nitrile imine group is according to formula (9w) or (9zd) as shown below, wherein R$^{13}$ is selected from the group consisting of linear or branched C$_1$-C$_{12}$ alkyl groups and C$_6$-C$_{12}$ aryl groups. Preferably, R$^{13}$ is a C$_1$-C$_6$ alkyl group, more preferably R$^{13}$ is a C$_1$-C$_4$ alkyl group. Even more preferably R$^{13}$ is methyl, ethyl, n-propyl, i-propyl, n-butyl, s-butyl or t-butyl. Yet even more preferably R$^{13}$ is methyl.

In another preferred embodiment, Q$^1$ is a diazo group. Preferably, the diazo group is according to formula (9x) as shown below, wherein R$^{14}$ is selected from the group consisting of hydrogen or a carbonyl derivative. More preferably, R$^{14}$ is hydrogen.

In another preferred embodiment, Q$^1$ is a ketone group. More preferably, the ketone group is according to formula (9y) as shown below, wherein R$^{15}$ is selected from the group consisting of linear or branched C$_1$-C$_{12}$ alkyl groups and C$_6$-C$_{12}$ aryl groups. Preferably, R$^{15}$ is a C$_1$-C$_6$ alkyl group, more preferably R$^{15}$ is a C$_1$-C$_4$ alkyl group. Even more preferably R$^{15}$ is methyl, ethyl, n-propyl, i-propyl, n-butyl, s-butyl or t-butyl. Yet even more preferably R$^{15}$ is methyl.

In another preferred embodiment, Q$^1$ is an (O-alkyl) hydroxylamino group. More preferably, the (O-alkyl)hydroxylamino group is according to formula (9z) as shown below.

In another preferred embodiment, Q$^1$ is a hydrazine group. Preferably, the hydrazine group is according to formula (9za) as shown below.

In another preferred embodiment, Q$^1$ is a halogenated N-maleimidyl group or a sulfonylated N-maleimidyl group. When Q$^1$ is a halogenated or sulfonylated N-maleimidyl group, Q$^1$ is preferably according to formula (9ze) as shown below, wherein R$^6$ is independently selected from the group consisting of hydrogen F, Cl, Br, I and —S(O)$_2$R$_{18}$, wherein R$^{18}$ is selected from the group consisting of, optionally substituted, C$_1$-C$_{12}$ alkyl groups and C$_4$-C$_{12}$ (hetero)aryl groups, and with the proviso that at least one R$^6$ is not hydrogen. When R$^6$ is halogen (i.e. when R$^6$ is F, Cl, Br or I), it is preferred that R$^6$ is Br. When R$^6$ is —S(O)$_2$R$_{18}$, it is preferred that R$_{18}$ is a C$_1$-C$_6$ alkyl group or a C$_4$-C$_6$ (hetero) aryl group, preferably a phenyl group.

In another preferred embodiment, Q$^1$ is a carbonyl halide group according to formula (9zf) as shown below, wherein X is selected from the group consisting of F, Cl, Br and I. Preferably, X is Cl or Br, and most preferably, X is Cl.

In another preferred embodiment, Q$^1$ is an allenamide group according to formula (9zg).

In another preferred embodiment, Q$^1$ is a 1,1-bis(sulfonylmethyl)methylcarbonyl group according to formula (9zh), or an elimination derivative thereof, wherein R$^{18}$ is selected from the group consisting of, optionally substituted, C$_1$-C$_{12}$ alkyl groups and C$_4$-C$_{12}$ (hetero)aryl groups. More preferably, R$_{18}$ is an, optionally substituted, C$_1$-C$_6$ alkyl group or a C$_4$-C$_6$ (hetero)aryl group, and most preferably a phenyl group.

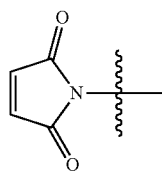

9a

-continued

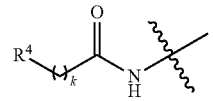

9b

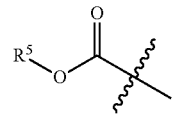

9c

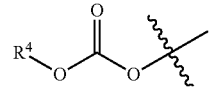

9d

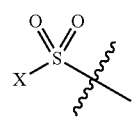

9e

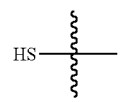

9f

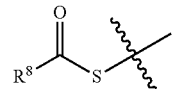

9g

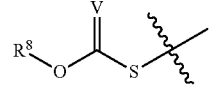

9h

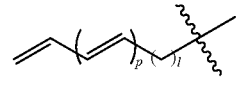

9i

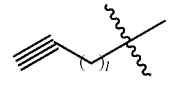

9j

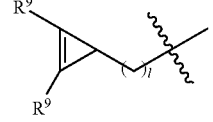

9k

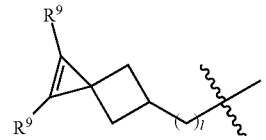

9l

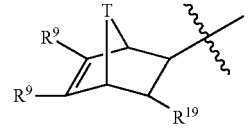

9m

-continued
9n 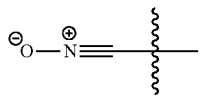
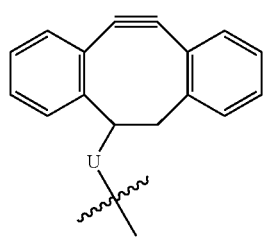
9o 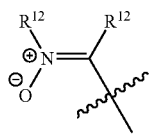
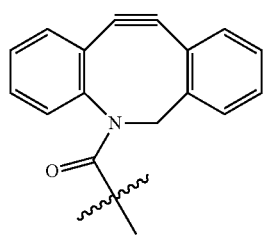
9p 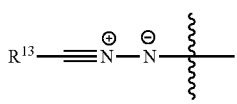
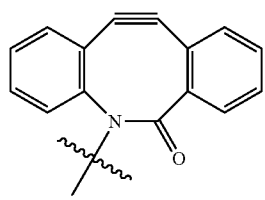
9q 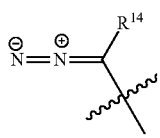
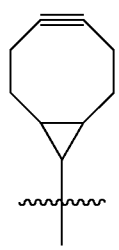
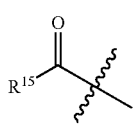
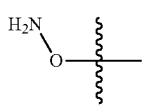
9r 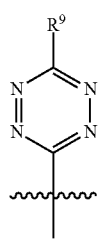
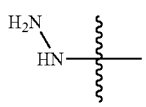
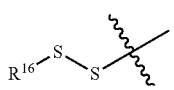
9s 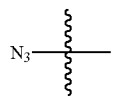
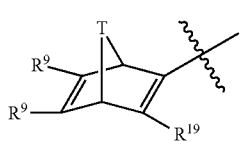
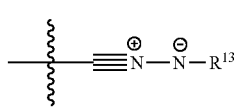
9t 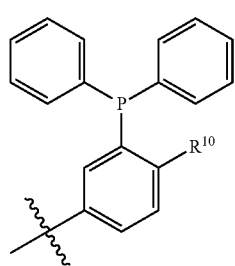
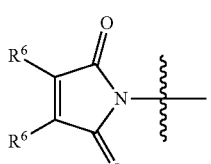
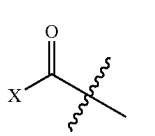
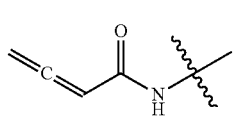

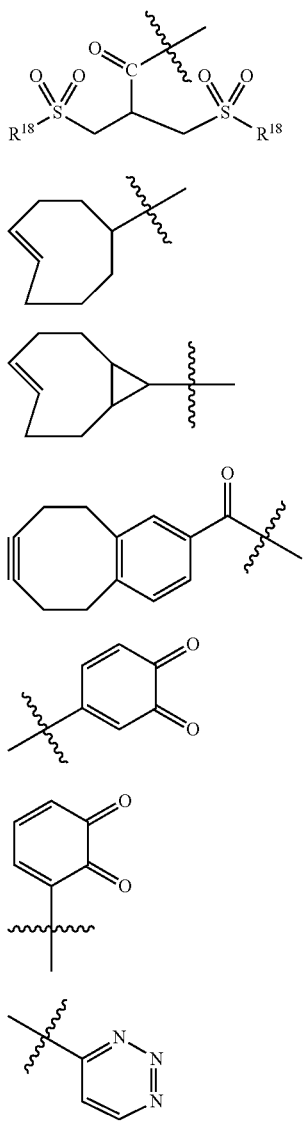

wherein k, l, X, T, U, V, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are as defined above.

In a preferred embodiment of the conjugation process according to the invention as described hereinbelow, conjugation is accomplished via a cycloaddition, such as a Diels-Alder reaction or a 1,3-dipolar cycloaddition, preferably the 1,3-dipolar cycloaddition. According to this embodiment, the reactive group $Q^1$ (as well as $F^1$ on the biomolecule) is selected from groups reactive in a cycloaddition reaction. Herein, reactive groups $Q^1$ and $F^1$ are complementary, i.e. they are capable of reacting with each other in a cycloaddition reaction.

For a Diels-Alder reaction, one of $F^1$ and $Q^1$ is a diene and the other of $F^1$ and $Q^1$ is a dienophile. As appreciated by the skilled person, the term "diene" in the context of the Diels-Alder reaction refers to 1,3-(hetero)dienes, and includes conjugated dienes ($R_2C=CR-CR=CR_2$), imines (e.g. $R_2C=CR-N=CR_2$ or $R_2C=CR-CR=NR$, $R_2C=N-N=CR_2$) and carbonyls (e.g. $R_2C=CR-CR=O$ or $O=CR-CR=O$). Hetero-Diels-Alder reactions with N- and O-containing dienes are known in the art. Any diene known in the art to be suitable for Diels-Alder reactions may be used as reactive group $Q^1$ or $F^1$. Preferred dienes include tetrazines as described above, 1,2-quinones as described above and triazines as described above. Although any dienophile known in the art to be suitable for Diels-Alder reactions may be used as reactive groups $Q^1$ or $F^1$, the dienophile is preferably an alkene or alkyne group as described above, most preferably an alkyne group. For conjugation via a Diels-Alder reaction, it is preferred that $F^1$ is the diene and $Q^1$ is the dienophile. Herein, when $Q^1$ is a diene, $F^1$ is a dienophile and when $Q^1$ is a dienophile, $F^1$ is a diene. Most preferably, $Q^1$ is a dienophile, preferably $Q^1$ is or comprises an alkynyl group, and $F^1$ is a diene, preferably a tetrazine, 1,2-quinone or triazine group.

For a 1,3-dipolar cycloaddition, one of $F^1$ and $Q^1$ is a 1,3-dipole and the other of $F^1$ and $Q^1$ is a dipolarophile. Any 1,3-dipole known in the art to be suitable for 1,3-dipolar cycloadditions may be used as reactive group $Q^1$ or $F^1$. Preferred 1,3-dipoles include azido groups, nitrone groups, nitrile oxide groups, nitrile imine groups and diazo groups. Although any dipolarophile known in the art to be suitable for 1,3-dipolar cycloadditions may be used as reactive groups $Q^1$ or $F^1$, the dipolarophile is preferably an alkene or alkyne group, most preferably an alkyne group. For conjugation via a 1,3-dipolar cycloaddition, it is preferred that $F^1$ is the 1,3-dipole and $Q^1$ is the dipolarophile. Herein, when $Q^1$ is a 1,3-dipole, $F^1$ is a dipolarophile and when $Q^1$ is a dipolarophile, $F^1$ is a 1,3-dipole. Most preferably, $Q^1$ is a dipolarophile, preferably $Q^1$ is or comprises an alkynyl group, and $F^1$ is a 1,3-dipole, preferably an azido group. Thus, in a preferred embodiment, $Q^1$ is selected from dipolarophiles and dienophiles. Preferably, $Q^1$ is an alkene or an alkyne group. In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q) and (9zk), as defined above and depicted below, more preferably selected from the formulae (9n), (9o), (9p), (9q) and (9zk). Most preferably, $Q^1$ is a bicyclo[6.1.0]non-4-yn-9-yl] group, preferably of formula (9q). These groups are known to be highly effective in the conjugation with azido-functionlized biomolecules as described herein, and when the sulfamide linker according to the invention is employed in such linker-conjugates and bioconjugates, any aggregation is beneficially reduced to a minimum. The sulfamide linker according to the invention provides a significant reduction in aggregation especially for such hydrophobic reactive groups of $Q^1$, and for the conjugated bioconjugates.

Figure 22:
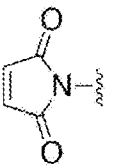
FIG. 22 shows a representative set of functional groups ($F^1$) in a biomolecule, either naturally present or introduced by engineering, which upon reaction with reactive group $Q^1$ lead to connecting group $Z^3$. Connecting group $Z^3$ may also be the result of a reaction between $F^2$ and $Q^2$. Functional group $F^1$ may also be artificially introduced (engineered) into a biomolecule at any position of choice.

As was described above, in the compound according to the invention, $Q^1$ is capable of reacting with a reactive group $F^1$ that is present on a biomolecule. Complementary reactive groups $F^1$ for reactive group $Q^1$ are known to a person skilled in the art, and are described in more detail below. Some representative examples of reaction between $F^1$ and $Q^1$ and their corresponding products are depicted in FIG. 22.

As described above, target molecule D and reactive group $Q^1$ are covalently attached to the linker in the linker-conjugate according to the invention. Covalent attachment of a target molecule D to the linker may occur for example via reaction of a functional group $F^2$ present on the target molecule with a reactive group $Q^2$ present on the linker. Suitable organic reactions for the attachment of a target molecule D to a linker are known to a person skilled in the art, as are functional groups $F^2$ that are complementary to a reactive group $Q^2$. Consequently, D may be attached to the linker via a connecting group Z.

The term "connecting group" herein refers to the structural element connecting one part of a compound and another part of the same compound. As will be understood by the person skilled in the art, the nature of a connecting group depends on the type of organic reaction with which the connection between the parts of said compound was obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—.

Reactive group $Q^1$ may be attached to the linker in a similar manner. Consequently, $Q^1$ may be attached to the spacer-moiety via a connecting group Z.

Numerous reactions are known in the art for the attachment of a target molecule to a linker, and for the attachment of a reactive group $Q^1$ to a linker. Consequently, a wide variety of connecting groups Z may be present in the linker-conjugate according to the invention.

The invention thus also relates to a compound according to the formula:

$(Q^1)_y$-$(Z^w)$-Sp-$(Z^x)$-$(D)_z$, wherein:
y is an integer in the range of 1 to 10;
z is an integer in the range of 1 to 10;
$Q^1$ is a reactive group capable of reacting with a functional group $F^1$ present on a biomolecule;
D is a target molecule;
Sp is a spacer moiety, wherein a spacer moiety is defined as a moiety that spaces (i.e. provides a certain distance between) and covalently links reactive group $Q^1$ and target molecule D;
$Z^w$ is a connecting group connecting reactive group $Q^1$ to said spacer moiety;
$Z^x$ is a connecting group connecting target molecule D to said spacer moiety; and
wherein said spacer moiety comprises a group according to Formula (1) or a salt thereof, wherein the group according to Formula (1) is as defined above.

In a preferred embodiment, a in the group according to formula (1) is 0. In another preferred embodiment, a in the group according to formula (1) is 1.

Preferred embodiments for y and z are as defined above for $(Q^1)_y$-Sp-$(D)_z$. It is further preferred that the compound is according to the formula $Q^1$-$(Z^w)$-Sp-$(Z^x)$-$(D)_4$, $Q^1$-$(Z^w)$—Sp-$(Z^x)$-$(D)_3$, $Q^1$-$(Z^w)$—Sp-$(Z^x)$-$(D)_2$ or $Q^1$-$(Z^w)$—Sp-$(Z^x)$-D, more preferably $Q^1$-$(Z^w)$-Sp-$(Z^x)$-$(D)_2$ or $Q^1$-$(Z^w)$-Sp-$(Z^x)$-D and most preferably $Q^1$-$(Z^w)$-Sp-$(Z^x)$-D, wherein $Z^w$ and $Z^x$ are as defined above.

Preferably, $Z^w$ and $Z^x$ are independently selected from the group consisting of —O—, —S—, —$NR^2$—, —N=N—, —C(O)—, —C(O)—$NR^2$—, —O—C(O)—, —O—C(O)—O—, —O—C(O)—$NR^2$, —$NR^2$—C(O)—, —$NR^2$—C(O)—O—, —$NR^2$—C(O)—$NR^2$—, —S—C(O)—, —S—C(O)—O—, —S—C(O)—$NR^2$—, —S(O)—, —$S(O)_2$—, —O—$S(O)_2$—, —O—$S(O)_2$—O—, —O—$S(O)_2$—$NR^2$—, —O—S(O)—, —O—S(O)—O—, —O—S(O)—$NR^2$—, —O—$NR^2$—C(O)—, —O—$NR^2$—C(O)—O—, —O—$NR^2$—C(O)—$NR^2$—, —$NR^2$—O—C(O)—, —$NR^2$—O—C(O)—O—, —$NR^2$—O—C(O)—$NR^2$—, —O—$NR^2$—C(S)—, —O—$NR^2$—C(S)—O—, —O—$NR^2$—C(S)—$NR^2$—, —$NR^2$—O—C(S)—, —$NR^2$—O—C(S)—O—, —$NR^2$—O—C(S)—$NR^2$—, —O—C(S)—, —O—C(S)—O—, —O—C(S)—$NR^2$—, —$NR^2$—C(S)—, —$NR^2$—C(S)—O—, —$NR^2$—C(S)—$NR^2$—, —S—$S(O)_2$—, —S—$S(O)_2$—O—, —S—$S(O)_2$—$NR^2$—, —$NR^2$—O—S(O)—, —$NR^2$—O—S(O)—O—, —$NR^2$—O—S(O)—$NR^2$—, —$NR^2$—O—$S(O)_2$—, —$NR^2$—O—$S(O)_2$—O—, —$NR^2$—O—$S(O)_2$—$NR^2$—, —O—$NR^2$—S(O)—, —O—$NR^2$—S(O)—O—, —O—$NR^2$—S(O)—$NR^2$—, —O—$NR^2$—$S(O)_2$—O—, —O—$NR^2$—$S(O)_2$—$NR^2$—, —O—$NR^2$—$S(O)_2$—, —O—P(O)$(R^2)_2$—, —S—P(O)$(R^2)_2$—, —$NR^2$—P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Preferred embodiments for D and $Q^1$ are as defined above.

More particularly, the present invention relates to a compound according to formula (4a) or (4b), or a salt thereof:

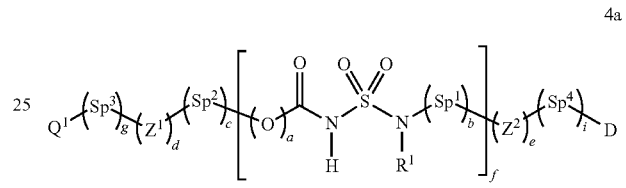

4a

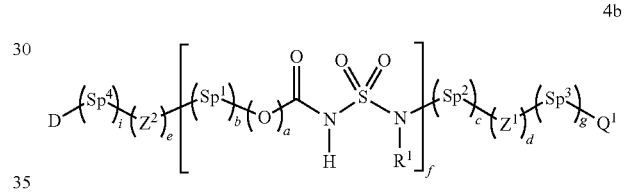

4b wherein:
a is independently 0 or 1;
b is independently 0 or 1;
c is 0 or 1;
d is 0 or 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or N($R^1$);
$Z^2$ is a connecting group that connects D or $Sp^4$ to $Sp^1$, N($R^1$), O or C(O); and
$R^1$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, -[$(Sp^1)_b$-$(Z^2)_e$—$(Sp^4)_i$-D] or -[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above.

The compound according to formula (4a) or (4b), or a salt thereof, may also be referred to as a linker-conjugate.

In a preferred embodiment, a is 1 in the compound according to formula (4a) or (4b). In another preferred embodiment, a is 0 in the compound according to formula (4a) or (4b).

As defined above, $Z^1$ is a connecting group that connects $Q^1$ or $Sp^3$ to $Sp^2$, O or C(O) or N($R^1$), and $Z^2$ is a connecting group that connects D or $Sp^4$ to $Sp^1$, N($R^1$), O or C(O). As described in more detail above, the term "connecting group" refers to a structural element connecting one part of a compound and another part of the same compound.

In a compound according to formula (4a), connecting group $Z^1$, when present (i.e. when d is 1), connects $Q^1$ (optionally via a spacer moiety $Sp^3$) to the O-atom or the C(O) group of the compound according to formula (4a), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the O-atom (a is 1) or to the C(O) group (a is 0) of the linker-conjugate according to formula (4a). When $Z^1$ is present (i.e. when d is 1), $Sp^3$ is present (i.e. g is 1) and $Sp^2$ is absent (i.e. c is 0), $Z^1$ connects spacer moiety $Sp^3$ to the O-atom (a is 1) or to the C(O) group (a is 0) of the linker-conjugate according to formula (4a). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4a). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4a).

In a compound according to formula (4b), connecting group $Z^1$, when present (i.e. when d is 1), connects $Q^1$ (optionally via a spacer moiety $Sp^3$) to the N-atom of the N($R^1$) group in the linker-conjugate according to formula (4b), optionally via a spacer moiety $Sp^2$. More particularly, when $Z^1$ is present (i.e. d is 1), and when $Sp^3$ and $Sp^2$ are absent (i.e. g is 0 and c is 0), $Z^1$ connects $Q^1$ to the N-atom of the N($R^1$) group of the linker-conjugate according to formula (4b). When $Z^1$ is present (i.e. when d is 1), $Sp^3$ is present (i.e. g is 1) and $Sp^2$ is absent (i.e. c is 0), $Z^1$ connects spacer moiety $Sp^3$ to the N-atom of the N($R^1$) group of the linker-conjugate according to formula (4b). When $Z^1$ is present (i.e. d is 1), and when $Sp^3$ and $Sp^2$ are present (i.e. g is 1 and c is 1), $Z^1$ connects spacer moiety $Sp^3$ to spacer moiety $Sp^2$ of the linker-conjugate according to formula (4b). When $Z^1$ is present (i.e. when d is 1), $Sp^3$ is absent (i.e. g is 0) and $Sp^2$ is present (i.e. c is 1), $Z^1$ connects $Q^1$ to spacer moiety $Sp^2$ of the linker-conjugate according to formula (4b).

In the compound according to formula (4a), when c, d and g are all 0, then $Q^1$ is attached directly to the O-atom (when a is 1) or to the C(O) group (when a is 0) of the linker-conjugate according to formula (4a).

In the compound according to formula (4b), when c, d and g are all 0, then $Q^1$ is attached directly to the N-atom of the N($R^1$) group of the linker-conjugate according to formula (4b).

In a compound according to formula (4a), connecting group $Z^2$, when present (i.e. when e is 1), connects D (optionally via a spacer moiety $Sp^4$) to the N-atom of the N($R^1$) group in the linker-conjugate according to formula (4a), optionally via a spacer moiety $Sp^1$. More particularly, when $Z^2$ is present (i.e. e is 1), and when $Sp^1$ and $Sp^4$ are absent (i.e. b is 0 and i is 0), $Z^2$ connects D to the N-atom of the N($R^1$) group of the linker-conjugate according to formula (4a). When $Z^2$ is present (i.e. when e is 1), $Sp^4$ is present (i.e. i is 1) and $Sp^1$ is absent (i.e. b is 0), $Z^2$ connects spacer moiety $Sp^4$ to the N-atom of the N($R^1$) group of the linker-conjugate according to formula (4a). When $Z^2$ is present (i.e. e is 1), and when $Sp^1$ and $Sp^4$ are present (i.e. b is 1 and i is 1), $Z^2$ connects spacer moiety $Sp^1$ to spacer moiety $Sp^4$ of the linker-conjugate according to formula (4a). When $Z^2$ is present (i.e. when e is 1), $Sp^4$ is absent (i.e. i is 0) and $Sp^1$ is present (i.e. b is 1), $Z^2$ connects D to spacer moiety $Sp^1$ of the linker-conjugate according to formula (4a).

In the compound according to formula (4a), when b, e and i are all 0, then D is attached directly to N-atom of the N($R^1$) group of the linker-conjugate according to formula (4a).

In the compound according to formula (4b), when b, e and i are all 0, then D is attached directly to the O-atom (when a is 1) or to the C(O) group (when a is 0) of the linker-conjugate according to formula (4b).

As will be understood by the person skilled in the art, the nature of a connecting group depends on the type of organic reaction with which the connection between the specific parts of said compound was obtained. A large number of organic reactions are available for connecting a reactive group $Q^1$ to a spacer moiety, and for connecting a target molecule to a spacer-moiety. Consequently, there is a large variety of connecting groups $Z^1$ and $Z^2$.

In a preferred embodiment of the linker-conjugate according to formula (4a) and (4b), $Z^1$ and $Z^2$ are independently selected from the group consisting of —O—, —S—, —S—S—, —$NR^2$—, —N=N—, —C(O)—, —C(O)—$NR^2$—, —O—C(O)—, —O—C(O)—O—, —O—C(O)—$NR^2$, —$NR^2$—C(O)—, —$NR^2$—C(O)—O—, —$NR^2$—C(O)—$NR^2$—, —S—C(O)—, —S—C(O)—O—, —S—C(O)—$NR^2$—, —S(O)—, —S(O)$_2$—, —O—S(O)$_2$—, —O—S(O)$_2$—O—, —O—S(O)$_2$—$NR^2$—, —O—S(O)—, —O—S(O)—O—, —O—S(O)—$NR^2$—, —O—$NR^2$—C(O)—, —O—$NR^2$—C(O)—O—, —O—$NR^2$—C(O)—$NR^2$—, —$NR^2$—O—C(O)—, —$NR^2$—O—C(O)—O—, —$NR^2$—O—C(O)—$NR^2$—, —O—$NR^2$—C(S)—, —O—$NR^2$—C(S)—O—, —O—$NR^2$—C(S)—$NR^2$—, —$NR^2$—O—C(S)—, —$NR^2$—O—C(S)—O—, —$NR^2$—O—C(S)—$NR^2$—, —O—C(S)—, —O—C(S)—O—, —O—C(S)—$NR^2$—, —$NR^2$—C(S)—, —$NR^2$—C(S)—O—, —$NR^2$—C(S)—$NR^2$—, —S—S(O)$_2$—, —S—S(O)$_2$—O—, —S—S(O)$_2$—$NR^2$—, —$NR^2$—O—S(O)—, —$NR^2$—O—S(O)—O—, —$NR^2$—O—S(O)—$NR^2$—, —$NR^2$—O—S(O)$_2$—, —$NR^2$—O—S(O)$_2$—O—, —$NR^2$—O—S(O)$_2$—$NR^2$—, —O—$NR^2$—S(O)—, —O—$NR^2$—S(O)—O—, —O—$NR^2$—S(O)—$NR^2$—, —O—$NR^2$—S(O)$_2$—O—, —O—$NR^2$—S(O)$_2$—$NR^2$—, —O—$NR^2$—S(O)$_2$—, —O—P(O)($R^2$)$_2$—, —S—P(O)($R^2$)$_2$—, —$NR^2$—P(O)($R^2$)$_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

As described above, in the compound according to formula (4a) or (4b), $Sp^1$, $Sp^2$, $Sp^3$ and $Sp^4$ are spacer-moieties. $Sp^1$, $Sp^2$, $Sp^3$ and $Sp^4$ may be, independently, absent or present (b, c, g and i are, independently, 0 or 1). $Sp^1$, if present, may be different from $Sp^2$, if present, from $Sp^3$ and/or from $Sp^4$, if present.

Spacer-moieties are known to a person skilled in the art. Examples of suitable spacer-moieties include (poly)ethylene glycol diamines (e.g. 1,8-diamino-3,6-dioxaoctane or equivalents comprising longer ethylene glycol chains), polyethylene glycol chains or polyethylene oxide chains, polypropylene glycol chains or polypropylene oxide chains and 1,x-diaminoalkanes wherein x is the number of carbon atoms in the alkane.

Another class of suitable spacer-moieties comprises cleavable spacer-moieties, or cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are disulfide-linkers that are cleaved upon reduction, peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas. Herein, suitable cleavable spacer-moieties also include spacer moieties comprising a specific, cleavable, sequence of amino acids. Examples include e.g. spacer-moieties comprising a Val-Cit (valine-citrulline) moiety. Bioconjugates containing a cleavable linker, such as Val-Cit linker, in particular Val-Cit-PABC, suffer considerably from aggregation in view of their limited water-solubility. For such bioconjugates, incorporating the sulfamide linker according to the invention is particularly beneficial. Also, conjugation reactions with a linker-conjugate comprising a cleavable linker are hampered by the limited water-solubility of the linker-conjugate. Hence, linker-conjugates comprising a cleavable linker, such as Val-Cit linker, in particular Val-Cit-PABC, and the sulfamide linker according to the invention outperform linker-conjugates comprising such a cleavable linker but lacking such sulfamide linker in conjugation to biomolecules.

Thus, in a preferred embodiment of the linker-conjugates according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Cit moiety, e.g. Val-Cit-PABC, Val-Cit-PAB, Fmoc-Val-Cit-PAB, etc. Preferably, a Val-Cit-PABC moiety is employed in the linker-conjugate.

In a preferred embodiment of the linker-conjugates according to formula (4a) and (4b), spacer moieties $Sp^1$, $Sp^2$, $Sp^3$ and $Sp^4$, if present, are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$, $Sp^2$, $Sp^3$ and $Sp^4$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably O, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or or S—S, wherein $R^3$ is independently selected from the group consisting of hydrogen and $C_1$-$C_4$ alkyl groups, preferably hydrogen or methyl.

Preferred spacer moieties $Sp^1$, $Sp^2$, $Sp^3$ and $Sp^4$ thus include —$(CH_2)_n$—, —$(CH_2CH_2)_n$—, —$(CH_2CH_2O)_n$—, —$(OCH_2CH_2)_n$—, —$(CH_2CH_2O)_nCH_2CH_2$—, —$CH_2CH_2(OCH_2CH_2)_n$—, —$(CH_2CH_2CH_2O)_n$—, —$(OCH_2CH_2CH_2)_n$—, —$(CH_2CH_2CH_2O)_n$ $CH_2CH_2CH_2$— and —$CH_2CH_2CH_2(OCH_2CH_2 CH_2)_n$—, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Since $Sp^1$, $Sp^2$, $Sp^3$ and $Sp^4$ are independently selected, $Sp^1$, if present, may be different from $Sp^2$, if present, from $Sp^3$ and/or from $Sp^4$, if present.

Reactive groups $Q^1$ are described in more detail above. In the linker-conjugate according to formula (4a) and (4b), it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, carbonyl halide groups, allenamide groups and 1,1-bis(sulfonylmethyl)methylcarbonyl groups or elimination derivatives thereof. In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above. In a preferred embodiment, $Q^1$ is according to formula (9a), (9b), (9c), (9f), (9j), (9n), (9o), (9p), (9q), (9s), (9t), (9zh), (9r), (9zl), (9zm) or (9zn). In an even further preferred embodiment, $Q^1$ is according to formula (9a), (9n), (9o), (9q), (9p), (9t), (9zh) or (9s), and in a particularly preferred embodiment, $Q^1$ is according to formula (9a), (9q), (9n), (9o), (9p), (9t) or (9zh), and preferred embodiments thereof, as defined above.

Target molecule D and preferred embodiments for target molecule D in the linker-conjugate according to formula (4a) and (4b) are as defined above. In a preferred embodiment of the linker-conjugates according to formula (4a) and (4b), D is selected from the group consisting of an active substance, a reporter molecule, a polymer, a solid surface, a hydrogel, a nanoparticle, a microparticle and a biomolecule. Active substances, reporter molecules, polymers, hydrogels, solid surfaces, nano- and microparticles and biomolecules, and preferred embodiments thereof, are described in more detail above.

As described above, $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is D, -[$(Sp^1)_b$-$(Z^2)_e$—$(Sp^4)_i$-D] or -[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above.

In a preferred embodiment, $R^1$ is hydrogen or a $C_1$-$C_{20}$ alkyl group, more preferably $R^1$ is hydrogen or a $C_1$-$C_{16}$ alkyl group, even more preferably $R^1$ is hydrogen or a $C_1$-$C_{10}$ alkyl group, wherein the alkyl group is optionally substituted and optionally interrupted by one or more heteroatoms selected from O, S and $NR^3$, preferably O, wherein $R^3$ is independently selected from the group consisting of hydrogen and $C_1$-$C_4$ alkyl groups. In a further preferred embodiment, $R^1$ is hydrogen. In another further preferred embodiment, $R^1$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^1$ is a polyethyleneglycol chain comprising a terminal —OH group. In another further preferred embodiment, $R^1$ is a $C_1$-$C_{12}$ alkyl group, more preferably a $C_1$-$C_6$ alkyl group, even more preferably a $C_1$-$C_4$ alkyl group, and yet even more preferably $R^1$ is selected from the group consisting of methyl, ethyl, n-propyl, i-propyl, n-butyl, s-butyl and t-butyl.

In another preferred embodiment, $R^1$ is a target molecule D, -[$(Sp^1)_b$-$(Z^2)_e$—$(Sp^4)_i$-D] or -[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above. When $R^1$ is D or -[$(Sp^1)_b$-$(Z^2)_e$—$(Sp^4)_i$-D], it is further preferred that the linker-conjugate is according to formula (4a). In this embodiment, linker-conjugate (4a) comprises two target molecules D, which may be the same or different. When $R^1$ is -[$(Sp^1)_b$-$(Z^2)_e$—$(Sp^4)_i$-D], $Sp^1$, b, $Z^2$, e, $Sp^4$, i and D in -[$(Sp^1)_b$—$(Z^2)_e$—$(Sp^4)_i$-D] may be the same or different from $Sp^1$, b, $Z^2$, e, $Sp^4$, i and D in the other -[$(Sp^1)_b$-$(Z^2)_e$—$(Sp^4)_i$-D] that is attached to the N-atom of $N(R^1)$. In a preferred embodiment, both -[$(Sp^1)_b$-$(Z^2)_e$—$(Sp^4)_i$-D] groups on the N-atom of $N(R^1)$ are the same.

When $R^1$ is -[$(Sp^2)_c$-$(Z^1)_d$—$(Sp^3)_g$-$Q^1$], it is further preferred that the linker-conjugate is according to formula (4b). In this embodiment, linker-conjugate (4b) comprises two target molecules $Q^1$, which may be the same or different.

When $R^1$ is $-[(Sp^2)_c-(Z^1)_d-(Sp^3)_g-Q^1]$, $Sp^2$, c, $Z^1$, d, $Sp^3$, g and D in $-[(Sp^1)_b-(Z^2)_e-(Sp^4)_i-D]$ may be the same or different from $Sp^1$, b, $Z^2$, e, $Sp^4$, i and $Q^1$ in the other $-[(Sp^2)_c-(Z^1)_d-(Sp^3)_g-Q^1]$ that is attached to the N-atom of $N(R^1)$. In a preferred embodiment, $-[(Sp^2)_c-(Z^1)_d-(Sp^3)_g-Q^1]$ groups on the N-atom of $N(R^1)$ are the same.

In the linker-conjugates according to formula (4a) and (4b), f is an integer in the range of 1 to 150. The linker-conjugate may thus comprise more than one group according to formula (1), the group according to formula (1) being as defined above. When more than one group according to formula (1) is present, i.e. When f is 2 or more, then a, b, $Sp^1$ and $R^1$ are independently selected. In other words, when f is 2 or more, each a is independently 0 or 1, each b is independently 0 or 1, each $Sp^1$ may be the same or different and each $R^1$ may be the same or different. In a preferred embodiment, f is an integer in the range of 1 to 100, preferably in the range of 1 to 50, more preferably in the range of 1 to 25, and even more preferably in the range of 1 to 15. More preferably, f is 1, 2, 3, 4, 5, 6, 7, 8, 9 or 10, even more preferably f is 1, 2, 3, 4, 5, 6, 7 or 8, yet even more preferably f is 1, 2, 3, 4, 5 or 6, yet even more preferably f is 1, 2, 3 or 4, and most preferably f is 1 in this embodiment. In another preferred embodiment, f is an integer in the range of 2 to 150, preferably in the range of 2 to 100, more preferably in the range of 2 to 50, more preferably in the range of 2 to 25, and even more preferably in the range of 2 to 15. More preferably, f is 2, 3, 4, 5, 6, 7, 8, 9 or 10, even more preferably f is 2, 3, 4, 5, 6, 7 or 8, yet even more preferably f is 2, 3, 4, 5 or 6, yet even more preferably f is 2, 3 or 4, and most preferably f is 2 in this embodiment.

As described above, in a preferred embodiment, a is 0 in the compound according to formula (4a) or (4b). The invention therefore also relates to a compound according to formula (6a) or (6b), or a salt thereof:

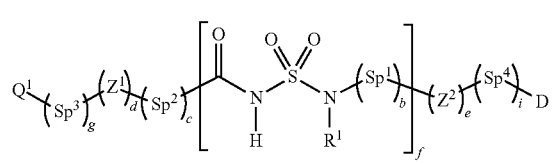

6a

6b wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

As described above, in another preferred embodiment, a is 1 in the compound according to formula (4a) or (4b). The invention therefore also relates to a compound according to formula (7a) or (7b), or a salt thereof:

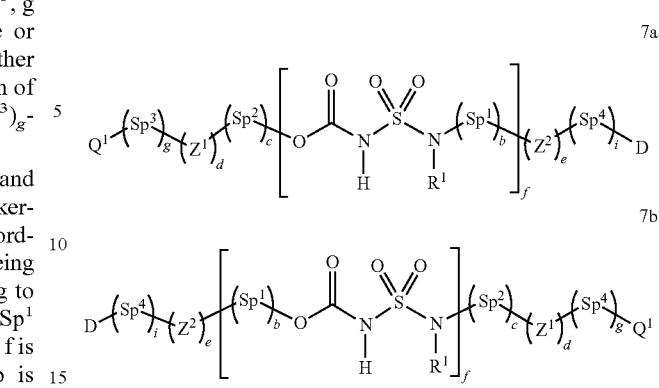

7a

7b wherein a, b, c, d, e, f, g, i, D, $Q^1$, $Sp^1$, $Sp^2$, $Sp^3$, $Sp^4$, $Z^1$, $Z^2$ and $R^1$, and their preferred embodiments, are as defined above for (4a) and (4b).

When $Sp^4$ is absent in the linker-conjugate according to formula (4a), i.e. when i is 0, target molecule D is linked to $Z^2$ (when e is 1), to $Sp^1$ (when e is 0 and b is 1) or to $N(R^1)$ (when e is 0 and b is 0). When $Sp^4$ is absent in the linker-conjugate according to formula (4b), i.e. when i is 0, target molecule D is linked to $Z^2$ (when e is 1), to $Sp^1$ (when e is 0 and b is 1), to the O-atom (when a is 1 and b and e are 0) or to the C(O) group (when a is 0 and b and e are 0). The invention therefore also relates to a linker-conjugate according to formula (4c) or (4d), or a salt thereof:

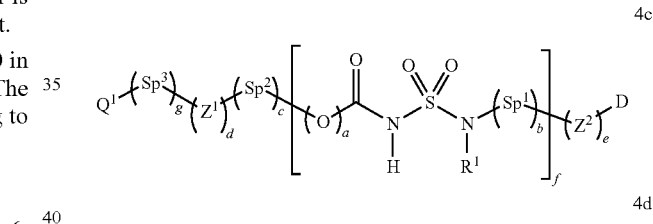

4c

4d wherein:
a, b, c, d, e, f, g, D, $Q^1$, $Sp^1$, $Sp^2$, $Sp^3$, $Z^1$, $Z^2$ and $R^1$, and their preferred embodiments, are as defined above for (4a) and (4b).

In a preferred embodiment, in the linker-conjugate according to formula (4c) or (4d), a is 0. In another preferred embodiment, in the linker-conjugate according to formula (4c) or (4d), a is 1.

In a specific embodiment of the linker-conjugate according to the invention, particularly a linker-conjugate according to formula (4a), (4b), (4c), (4d), (6a), (6b), (7a) or (7b), $Sp^1$, $Sp^2$ $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg) (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above. In a preferred embodiment, $Q^1$ is according to formula (9a), (9b), (9c), (9f), (9j), (9n), (9o), (9p), (9q), (9s) (9t), (9zh), (9r), (9zl), (9zm) or (9zn). In an even further preferred embodiment, $Q^1$ is according to formula (9a), (9n), (9o), (9p), (9q), (9t), (9zh) or (9s), and in a particularly preferred embodiment, $Q^1$ is according to formula (9a), (9q), (9n), (9p), (9t), (9zh) or (9o), and preferred embodiments thereof, as defined above.

A linker is herein defined as a moiety that connects two or more elements of a compound.

Consequently, in the linker-conjugate according to formula (4a), (4b), (4c), (4d), (6a), (6b), (7a) or (7b) as defined above, linker as defined above may be represented by formula (8a) and (8b), respectively:

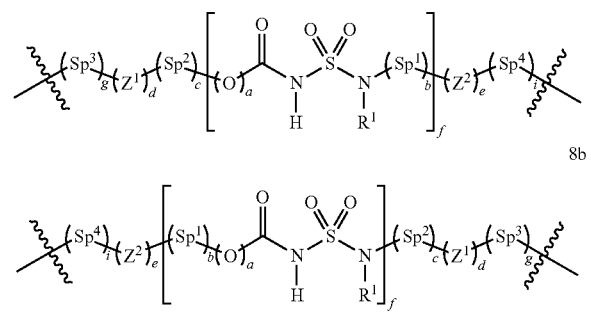

As will be understood by the person skilled in the art, preferred embodiments of spacer-moieties (8a) and (8b) may depend on e.g. the nature of reactive groups $Q^1$ and D in the linker-conjugate, the synthetic method to prepare the linker-conjugate (e.g. the nature of complementary functional group $F^2$ on a target molecule), the nature of a bioconjugate that is prepared using the the linker-conjugate (e.g. the nature of complementary functional group $F^1$ on the biomolecule).

When $Q^1$ is for example a cyclooctynyl group according to formula (9n), (9o), (9p), (9q) or (9zk) as defined above, then preferably $Sp^3$ is present (g is 1).

When for example the linker-conjugate was prepared via reaction of a reactive group $Q^2$ that is a cyclooctynyl group according to formula (9n), (9o), (9p), (9q) or (9zk) with an azido functional group $F^2$, then preferably $Sp^4$ is present (i is 1).

Furthermore, it is preferred that at least one of $Sp^1$, $Sp^2$, $Sp^3$ and $Sp^4$ is present, i.e. at least one of b, c, g, and i is not 0. In another preferred embodiment, at least one of $Sp^1$ and $Sp^4$ and at least one of $Sp^2$ and $Sp^3$ are present.

When f is 2 or more, it is preferred that $Sp^1$ is present (b is 1).

These preferred embodiments of the linker-moiety (8a) and (8b) also hold for the linker-moiety in bioconjugates according to the invention as described in more detail below.

Preferred embodiments of $Sp^1$, $Sp^2$, $Sp^3$ and $Sp^4$ are as defined above.

Linker-Construct

A linker-construct is herein defined as a compound wherein a reactive group $Q^1$ is covalently connected to a reactive group $Q^2$ via a linker. A linker-construct comprises a reactive group $Q^1$ capable of reacting with a reactive group $F^1$ present on a biomolecule, and a reactive group $Q^2$ capable of reacting with a reactive group $F^2$ present on a target molecule. $Q^1$ and $Q^2$ may be the same, or different. A linker-construct may comprise more than one reactive group $Q^1$ and/or more than one reactive group $Q^2$. When more than one reactive groups $Q^1$ are present the groups $Q^1$ may be the same or different, and when more than one reactive groups $Q^2$ are present the groups $Q^2$ may be the same or different.

The present invention also relates to a compound, more particularly to a linker-construct, said compound comprising an alpha-end and an omega-end, the compound comprising on the alpha-end a functional group $Q^1$ capable of reacting with a functional group $F^1$ present on a biomolecule and on the omega-end a functional group $Q^2$ capable of reacting with a functional group $F^2$ present on a target molecule, the compound further comprising a group according to formula (1), or a salt thereof, wherein said group according to formula (1) is as defined above, and wherein the group according to formula (1), or a salt thereof, is situated in between said alpha-end and said omega-end of the compound.

Reactive group $Q^1$ is covalently bonded to the alpha-end of the compound, and reactive group $Q^2$ is covalently bonded to a omega-end of the compound.

This compound according to the invention may also be referred to as a linker-construct. In the linker-construct according to the invention, a reactive group $Q^2$ is covalently connected to a reactive group $Q^1$ via a linker, and said linker comprises a group according to formula (1), or a salt thereof, as defined above. When the linker-construct according to the invention comprises a salt of the group according to formula (1), the salt is preferably a pharmaceutically acceptable salt.

The linker-construct according to the invention may comprise more than one reactive group $Q^2$. Consequently, the linker may thus comprise e.g. a third (fourth, fifth, etc.)—end, which may be referred to as a psi, chi, phi, etc.—end, the third (fourth, fifth, etc.) end comprising a reactive group $Q^2$. Similarly, the linker-conjugate may comprise more than one reactive group $Q^1$.

The linker-construct according to the invention may therefore also be denoted as $(Q^1)_y$-Sp-$(Q^2)_z$, wherein y is an integer in the range of 1 to 10 and z is an integer in the range of 1 to 10.

The invention thus also relates to a linker-construct according to the formula:

$(Q^1)_y$-Sp-$(Q^2)_z$, wherein:
y is an integer in the range of 1 to 10;
z is an integer in the range of 1 to 10;
$Q^1$ is a reactive group capable of reacting with a functional group $F^1$ present on a biomolecule;
$Q^2$ is a reactive group capable of reacting with a functional group $F^2$ present on a target molecule;
Sp is a spacer moiety, wherein a spacer moiety is defined as a moiety that spaces (i.e. provides a certain distance between) and covalently links reactive group $Q^1$ and reactive group $Q^2$; and
wherein said spacer moiety comprises a group according to Formula (1) or a salt thereof, wherein the group according to Formula (1) is as defined above.

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the linker-construct is according to the formula $Q^1$-Sp-$(Q^2)_4$, $Q^1$-Sp-$(Q^2)_3$, $Q^1$-Sp-$(Q^2)_2$ or $Q^1$-Sp-$Q^2$.

The linker-construct according to the invention comprises a group according to formula (1) as defined above, or a salt thereof. In a preferred embodiment, the linker-construct according to the invention comprises a group according to formula (1) wherein a is 0, or a salt thereof. In this embodiment, the linker-construct thus comprises a group according to formula (2) or a salt thereof:

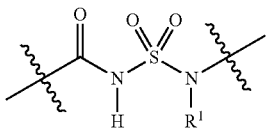

2 wherein $R^1$ is as defined above.

In another preferred embodiment, the linker-construct according to the invention comprises a group according to formula (1) wherein a is 1, or a salt thereof. In this embodiment, the linker-construct thus comprises a group according to formula (3) or a salt thereof:

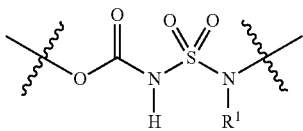

3 wherein $R^1$ is as defined above.

In the linker-construct according to the invention, $R^1$ and preferred embodiments of $R^1$ are as defined above. Furthermore, reactive group $Q^1$ and spacer moiety Sp, as well as preferred embodiments thereof, are as defined above for the linker-conjugate according to the invention.

More particular, the invention relates to a compound according to the formula:

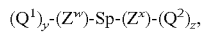

wherein:
y is an integer in the range of 1 to 10;
z is an integer in the range of 1 to 10;
$Q^1$ is a reactive group capable of reacting with a functional group $F^1$ present on a biomolecule;
$Q^2$ is a reactive group capable of reacting with a functional group $F^2$ present on a biomolecule;
Sp is a spacer moiety, wherein a spacer moiety is defined as a moiety that spaces (i.e. provides a certain distance between) and covalently links reactive groups $Q^1$ and $Q^2$;
$Z^w$ is a connecting group connecting reactive group $Q^1$ to said spacer moiety;
$Z^x$ is a connecting group connecting reactive group $Q^2$ to said spacer moiety; and
wherein said spacer moiety comprises a group according to Formula (1) or a salt thereof, wherein the group according to Formula (1) is as defined above.

In a preferred embodiment, a in the group according to formula (1) is 0. In another preferred embodiment, a in the group according to formula (1) is 1.

Preferred embodiments for y and z are as defined above for $(Q^1)_y$-Sp-$(Q^2)_z$. It is further preferred that the compound is according to the formula $Q^1$-$(Z^w)$-Sp-$(Z^x)$-$(Q^2)_4$, $Q^1$-$(Z^w)$-Sp-$(Z^x)$-$(Q^2)_3$, $Q^1$-$(Z^w)$-Sp-$(Z^x)$-$(Q^2)_2$ or $Q^1$-$(Z^w)$-Sp-$(Z^x)$-$Q^2$, more preferably $Q^1$-$(Z^w)$-Sp-$(Z^x)$-$(Q^2)_2$ or $Q^1$-$(Z^w)$-Sp-$(Z^x)$-$Q^2$ and most preferably $Q^1$-$(Z^w)$-Sp-$(Z^x)$-$Q^2$, wherein $Z^w$ and $Z^x$ are as defined above.

In the linker compound according to the invention, Z and $Z^x$ are preferably independently selected from the group consisting of —O—, —S—, —$NR^2$—, —N=N—, —C(O)—, —C(O)—$NR^2$—, —O—C(O)—, —O—C(O)—O—, —O—C(O)—$NR^2$, —$NR^2$—C(O)—, —$NR^2$—C(O)—O—, —$NR^2$—C(O)—$NR^2$—, —S—C(O)—, —S—C(O)—O—, —S—C(O)—$NR^2$—, —S(O)—, —S(O)$_2$—, —O—S(O)$_2$—, —O—S(O)$_2$—O—, —O—S(O)$_2$—$NR^2$—, —O—S(O)—, —O—S(O)—O—, —O—S(O)—$NR^2$—, —O—$NR^2$—C(O)—, —O—$NR^2$—C(O)—O—, —O—$NR^2$—C(O)—$NR^2$—, —$NR^2$—O—C(O)—, —$NR^2$—O—C(O)—O—, —$NR^2$—O—C(O)—$NR^2$—, —O—$NR^2$—C(S)—, —O—$NR^2$—C(S)—O—, —O—$NR^2$—C(S)—$NR^2$—, —$NR^2$—O—C(S)—, —$NR^2$—O—C(S)—O—, —$NR^2$—O—C(S)—$NR^2$—, —O—C(S)—, —O—C(S)—O—, —O—C(S)—$NR^2$—, —$NR^2$—C(S)—, —$NR^2$—C(S)—O—, —$NR^2$—C(S)—$NR^2$—, —S—S(O)$_2$—, —S—S(O)$_2$—O—, —S—S(O)$_2$—$NR^2$—, —$NR^2$—O—S(O)—, —$NR^2$—O—S(O)—O—, —$NR^2$—O—S(O)—$NR^2$—, —$NR^2$—O—S(O)$_2$—, —$NR^2$—S(O)$_2$—, —$NR^2$—O—S(O)$_2$—$NR^2$—, —O—$NR^2$—S(O)—, —O—$NR^2$—S(O)—O—, —O—$NR^2$—S(O)—$NR^2$—, —O—$NR^2$—S(O)$_2$—O—, —O—$NR^2$—S(O)$_2$—$NR^2$—, —O—$NR^2$—S(O)$_2$—, —O—P(O)$(R^2)_2$—, —S—P(O)$(R^2)_2$—, —$NR^2$—P(O)$(R^2)_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Preferred embodiments for $Q^1$ are as defined above.

In the linker-construct according to the invention, $Q^2$ is a reactive group capable of reacting with a functional group $F^2$ present on a target molecule. Reactive groups $Q^2$ capable of reacting with such a functional group $F^2$ are known to a person skilled in the art. In a preferred embodiment, $Q^2$ is a reactive group selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl] groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)-methylcarbonyl groups or elimination derivatives thereof, carbonyl halide groups and allenamide groups, —$[C(R^{17})_2C(R^{17})_2O]_q$—$R^{17}$, wherein q is in the range of 1 to 200, —CN, —NCV, —VCN, —$VR^{17}$, —$N(R^{17})_2$, —$^+N(R^{17})_3$—$C(V)N(R^{17})_2$, —$C(R^{17})_2VR^{17}$, —$C(V)R^{17}$, —$C(V)VR^{17}$, —$S(O)R^{17}$, —$S(O)_2R^{17}$, —$S(O)OR^{17}$, —$S(O)_2OR^{17}$, —$S(O)N(R^{17})_2$, —$S(O)_2N(R^{17})_2$, —$OS(O)R^{17}$, —$OS(O)_2R^{17}$, —$OS(O)OR^{17}$, —$OS(O)_2OR^{17}$, —$P(O)(R^{17})(OR^{17})$, —$P(O)(OR^{17})_2$, —$OP(O)(OR^{17})_2$, —$Si(R^{17})_3$, —VC(V)R$^{17}$, —VC(V)VR$^{17}$, —VC(V)N(R$^{17}$)$_2$, —N(R$^{17}$)C(V)R$^{17}$, N(R$^{17}$)C(V)VR$^{17}$ and —N(R$^{17}$)C(V)N(R$^{17}$)$_2$, wherein V is O or S and wherein R$^{17}$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups.

In a further preferred embodiment, Q$^2$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above. In this embodiment it is further preferred that Q$^2$ is according to formula (9a), (9b), (9c), (9f), (9j), (9n), (9o), (9p), (9q), (9s), (9t), (9zh), (9r), (9zl), (9zm) or (9zn), more preferably according to formula (9a), (9n), (9o), (9p), (9q), (9t), (9zh) or (9s), and even more preferably Q$^2$ is according to formula (9a), (9p), (9q), (9n), (9t), (9zh), or (9o), and preferred embodiments thereof, as defined above. Most preferably, Q$^2$ is according to formula (9a), (9p), (9q), (9n), (9t), (9zh) or (9o), and preferred embodiments thereof, as defined above.

In another further preferred embodiment, Q$^2$ is selected from the group consisting of —[C(R$^{17}$)$_2$C(R$^{17}$)$_2$O]$_q$—R$^{17}$, wherein q is in the range of 1 to 200, —CN, —NCV, —VCN, —VR$^{17}$, —$^+$N(R$^{17}$)$_2$, —$^+$N(R$^{17}$)$_3$, —C(V)N(R$^{17}$)$_2$, —C(R$^{17}$)$_2$VR$^{17}$, —C(V)R$^{17}$, —C(V) VR$^{17}$, —S(O)R$^{17}$, —S(O)$_2$R$^{17}$, —S(O)OR$^{17}$, —S(O)$_2$OR$^{17}$, —S(O)N(R$^{17}$)$_2$, —S(O)$_2$N(R$^{17}$)$_2$, —OS(O)R$^{17}$, —OS(O)$_2$R$^{17}$, —OS(O)OR$^{17}$, —OS(O)$_2$OR$^{17}$, —P(O)(R$^{17}$)(OR$^{17}$), —P(O)(OR$^{17}$)$_2$, —OP(O)(OR$^{17}$)$_2$, —Si(R$^{17}$)$_3$, —VC(V)R$^{17}$, —VC(V)VR$^{17}$, —VC(V)N(R$^{17}$)$_2$, —N(R$^{17}$)C(V)R$^{17}$, —N(R$^{17}$)C(V)VR$^{17}$ and —N(R$^{17}$)C(V)N(R$^{17}$)$_2$, wherein V and R$^{17}$ are as defined above. In this embodiment it is further preferred that Q$^2$ is selected from the group consisting of —OR$^{17}$, —SR$^{17}$, —N(R$^{17}$)$_2$, —$^+$N(R$^{17}$)$_3$, —C(O)N(R$^{17}$)$_2$, —C(R$^{17}$)$_2$OR$^{17}$, —C(O)R$^{17}$, —C(O)OR$^1$ 7, —S(O)R$^{17}$, —S(O)$_2$R$^{17}$, —S(O)OR$^{17}$, —S(O)$_2$R$^{17}$, —S(O)N(R$^{17}$)$_2$, —S(O)$_2$N(R$^{17}$)$_2$, —OS(O)R$^{17}$, —OS(O)$_2$R$^{17}$, —OS(O)OR$^{17}$, —OS(O)$_2$OR$^{17}$, —P(O)(R$^{17}$)(OR$^{17}$), —P(O)(OR$^{17}$)$_2$, —OP(O)(OR$^{17}$)$_2$, —Si(R$^{17}$)$_3$, —OC(O)R$^{17}$, —OC(O)OR$^{17}$, —OC(O)N(R$^{17}$)$_2$, —N(R$^{17}$)C(O)R$^{17}$, —N(R$^{17}$)C(O)OR$^{17}$ and —N(R$^{17}$)C(O)N(R$^{17}$)$_2$, wherein R$^{17}$ is as defined above.

In a specific embodiment of the linker-construct according to the invention, Q$^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above; and spacer moiety Sp is selected from the group consisting of linear or branched C$_1$-C$_{20}$ alkylene groups, the alkylene groups being optionally substituted and optionally interrupted by one or more heteroatoms selected from the group consisting of O, S and NR$^3$, wherein R$^3$ is independently selected from the group consisting of hydrogen and C$_1$-C$_4$ alkyl groups; wherein the spacer moiety Sp is interrupted by one or more groups according to formula (1) or a salt thereof, and wherein (1) is as defined above.

In a preferred embodiment, said spacer moiety Sp is interrupted by one or more groups according to formula (2), or a salt thereof, wherein (2) is as defined above. In another preferred embodiment, said spacer moiety Sp is interrupted by one or more groups according to formula (3), or a salt thereof, wherein (3) is as defined above.

In a further preferred embodiment, Q$^1$ is according to formula (9a), (9b), (9c), (9f), (9j), (9n), (9o), (9p), (9q), (9s), (9t), (9zh), (9zk), (9r), (9zl), (9zm) or (9zn). In an even further preferred embodiment, Q$^1$ is according to formula (9a), (9n), (9o), (9p), (9q), (9t), (9zh) or (9s), and in a particularly preferred embodiment, Q$^1$ is according to formula (9a), (9p), (9q), (9n), (9t), (9zh), (9zk) or (90), and preferred embodiments thereof, as defined above. Most preferably Q$^1$ is according to formula (9a), (9p), (9q), (9n), (9t), (9zh) or (90), and preferred embodiments thereof, as defined above.

Process for the Preparation of a Linker-Conjugate

The present invention also relates to a process for the preparation of a linker-conjugate according to the invention. In particular, the invention relates to a process for the preparation of a linker-conjugate according to the invention, the process comprising the step of reacting a functional group Q$^2$ of a linker-construct with a functional group F$^2$ of a target molecule, wherein said linker-construct is a compound comprising an alpha-end and an omega-end, the compound comprising on the alpha-end a functional group Q$^1$ capable of reacting with a functional group F$^1$ present on a biomolecule and on the omega-end a functional group Q$^2$ capable of reacting with a functional group F$^2$ present on said target molecule, the compound further comprising a group according to formula (1), or a salt thereof, wherein said group according to formula (1) is as defined above, and wherein the group according to formula (1), or the salt thereof, is situated in between said alpha-end and said omega-end of the compound.

The linker-construct and preferred embodiments thereof, including preferred embodiments of Q$^1$, Q$^2$ and target molecule D, are described in detail above.

In a preferred embodiment of the process for the preparation of a linker-conjugate, the linker-construct is according to (Q$^1$)$_y$-Sp-(Q$^2$)$_z$ as defined above. In a further preferred embodiment of the process for the preparation of a linker-conjugate, the linker-construct is according to (Q$^1$)$_y$-(Z$^w$)—Sp-(Z$^x$)-(Q$^2$)$_z$ as defined above.

The invention further relates to the use of a sulfamide linker-construct according to the invention in a bioconjugation process. The linker-construct according to the invention, and preferred embodiments therefore, are described in detail above. The invention particularly relates to the use of a linker-construct according to formula (Q$^1$)-Sp-(Q$^2$)$_z$ in a bioconjugation process, and to the use of a linker-construct according to formula (Q$^1$)$_y$-(Z$^w$)—Sp-(Z$^x$)-(Q$^2$)$_z$ in a bioconjugation process.

The invention also relates to the use of a linker-conjugate according to the invention in a bioconjugation process. The linker-conjugate according to the invention, and preferred embodiments therefore, are described in detail above. The invention particularly relates to the use of a linker-conjugate according to formula (4a), (4b), (4c), (4d), (6a), (6b), (7a) or (7b) in a bioconjugation process.

Bioconjugate

A bioconjugate is herein defined as a compound wherein a biomolecule is covalently connected to a target molecule via a linker. A bioconjugate comprises one or more biomolecules and/or one or more target molecules. The linker may comprise one or more spacer moieties. The bioconjugate according to the invention is conveniently prepared by the process for preparation of a bioconjugate according to the invention, wherein the linker-conjugate comprising reactive group $Q^1$ is conjugated to a biomolecule comprising reactive group $F^1$. In this conjugation reaction, reactive groups $Q^1$ and $F^1$ react with each other to form a linker moiety, which joins the linker-conjugate with the biomolecule. All preferred embodiments described herein for the linker-conjugate and the biomolecule thus equally apply to the bioconjugate according to the invention, except for all said for $Q^1$ and $F^1$, wherein the bioconjugate according to the invention contains the reaction product of $Q^1$ and $F^1$ as defined herein.

The invention also relates to a compound, the compound comprising an alpha-end and an omega-end, the compound comprising on the alpha-end a biomolecule and on the omega-end a target molecule, the compound further comprising a group according to formula (1) or a salt thereof:

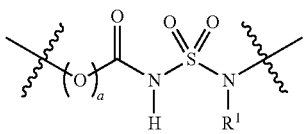

wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or
$R^1$ is a target molecule D, wherein the target molecule is optionally connected to N via a spacer moiety;
and wherein the group according to formula (1), or the salt thereof, is situated in between said alpha-end and said omega-end.

In a preferred embodiment, the compound further comprises a moiety that is obtainable by a cycloaddition reaction, preferably a 1,3-dipolar cycloaddition reaction, most preferably a 1,2,3-triazole ring, which is located between said alpha-end and said group according to formula (1). Herein, the compound thus comprises, when view for the alpha end to the omega end, a biomolecule, a moiety that is obtainable by a cycloaddition reaction, a group according to formula (1) and a target molecule.

In a further preferred embodiment, the target molecule is hydrophobic as defined hereinabove.

This compound according to the invention may also be referred to as a bioconjugate. When the bioconjugate according to the invention comprises a salt of the group according to formula (1), the salt is preferably a pharmaceutically acceptable salt.

The biomolecule is covalently attached to the alpha-end, and the target molecule is covalently attached to the omega-end of the bioconjugate according to the invention.

The bioconjugate according to the invention may comprise more than one target molecule. Similarly, the bioconjugate may comprise more than one biomolecule. Biomolecule B and target molecule D, and preferred embodiments thereof, are described in more detail above. Preferred embodiments for D in the bioconjugate according to the invention correspond to preferred embodiments of D in the linker-conjugate according to the invention as were described in more detail above. Preferred embodiments for the linker (8a) or (8b) in the bioconjugate according to the invention correspond to preferred embodiments of the linker in the linker-conjugate according to the invention, as were described in more detail above.

In the bioconjugate according to the invention, biomolecule B is preferably selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. Most preferably, biomolecule B is selected from the group consisting of proteins, including glycoproteins and antibodies, polypeptides, peptides and glycans.

The bioconjugate according to the invention may also be defined as a bioconjugate wherein a biomolecule is conjugated to a target molecule via a spacer-moiety, wherein the spacer-moiety comprises a group according to formula (1), or a salt thereof, wherein the group according to formula (1) is as defined above.

The bioconjugate according to the invention may also be denoted as $(B)_y$—Sp-$(D)_z$, wherein y is an integer in the range of 1 to 10 and z is an integer in the range of 1 to 10.

The invention thus also relates to a bioconjugate according to the formula:

$(B)_y$-Sp-$(D)_z$, wherein:
y is an integer in the range of 1 to 10;
z is an integer in the range of 1 to 10;
B is a biomolecule;
D is a target molecule;
Sp is a spacer moiety, wherein a spacer moiety is defined as a moiety that spaces (i.e. provides a certain distance between) and covalently links biomolecule B and target molecule D; and
wherein said spacer moiety comprises a group according to formula (1) or a salt thereof, wherein the group according to formula (1) is as defined above.

In a preferred embodiment, said spacer moiety further comprises a moiety that is obtainable by a cycloaddition reaction, preferably a 1,3-dipolar cycloaddition reaction, most preferably a 1,2,3-triazole ring, which is located between B and said group according to formula (1).

Preferably, y is 1, 2, 3 or 4, more preferably y is 1 or 2 and most preferably, y is 1. Preferably, z is 1, 2, 3, 4, 5 or 6, more preferably z is 1, 2, 3 or 4, even more preferably z is 1, 2 or 3, yet even more preferably z is 1 or 2 and most preferably z is 1. More preferably, y is 1 or 2, preferably 1, and z is 1, 2, 3 or 4, yet even more preferably y is 1 or 2, preferably 1, and z is 1, 2 or 3, yet even more preferably y is 1 or 2, preferably 1, and z is 1 or 2, and most preferably y is 1 and z is 1. In a preferred embodiment, the bioconjugate is according to the formula B-Sp-$(D)_4$, B-Sp-$(D)_3$, B-Sp-$(D)_2$ or B-Sp-D.

As described above, the bioconjugate according to the invention comprises a group according to formula (1) as defined above, or a salt thereof. In a preferred embodiment, the bioconjugate comprises a group according to formula (1)

wherein a is 0, or a salt thereof. In this embodiment, the bioconjugate thus comprises a group according to formula (2) or a salt thereof, wherein (2) is as defined above.

In another preferred embodiment, the bioconjugate comprises a group according to formula (1) wherein a is 1, or a salt thereof. In this embodiment, the bioconjugate thus comprises a group according to formula (3) or a salt thereof, wherein (3) is as defined above.

In the bioconjugate according to the invention, $R^1$, spacer moiety Sp, as well as preferred embodiments of $R^1$ and Sp, are as defined above for the linker-conjugate according to the invention.

In a preferred embodiment, the bioconjugate is according to formula (5a) or (5b), or a salt thereof:

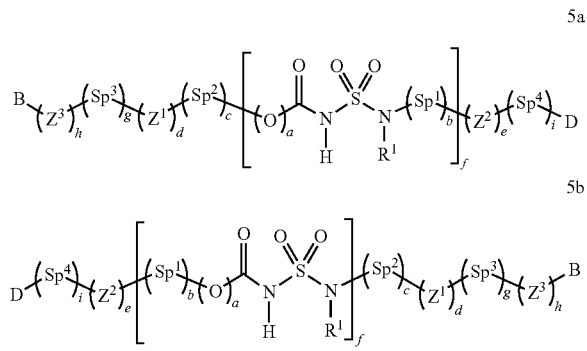

wherein a, b, c, d, e, f, g, h, i, D, $Sp^1$, $Sp^2$, $Sp^3$, $Sp^4$, $Z^1$, $Z^2$, $Z^3$ and $R^1$, and preferred embodiments thereof, are as defined above for linker-conjugate (4a) and (4b); and
h is 0 or 1;
$Z^3$ is a connecting group that connects B to $Sp^3$, $Z^1$, $Sp^2$, O or C(O); and
B is a biomolecule.

Preferably, h is 1.

Preferred embodiments of biomolecule B are as defined above.

When the bioconjugate according to the invention is a salt of (5a) or (5b), the salt is preferably a pharmaceutically acceptable salt.

$Z^3$ is a connecting group. As described above, the term "connecting group" herein refers to the structural element connecting one part of a compound and another part of the same compound. Typically, a bioconjugate is prepared via reaction of a reactive group $Q^1$ present in a linker-conjugate with a functional group $F^1$ present in a biomolecule. As will be understood by the person skilled in the art, the nature of connecting group $Z^3$ depends on the type of organic reaction that was used to establish the connection between a biomolecule and a linker-conjugate. In other words, the nature of $Z^3$ depends on the nature of reactive group $Q^1$ of the linker-conjugate and the nature of functional group $F^1$ in the biomolecule. Since there is a large number of different chemical reactions available for establishing the connection between a biomolecule and a linker-conjugate, consequently there is a large number of possibilities for $Z^3$.

Several examples of suitable combinations of $F^1$ and $Q^1$, and of connecting group $Z^3$ that will be present in a bioconjugate when a linker-conjugate comprising $Q^1$ is conjugated to a biomolecule comprising a complementary functional group $F^1$, are shown in FIG. 22.

When $F^1$ is for example a thiol group, complementary groups $Q^1$ include N-maleimidyl groups and alkenyl groups, and the corresponding connecting groups $Z^3$ are as shown in FIG. 22. When $F^1$ is a thiol group, complementary groups $Q^1$ also include allenamide groups.

When $F^1$ is for example an amino group, complementary groups $Q^1$ include ketone groups, activated ester groups and azido groups, and the corresponding connecting groups $Z^3$ are as shown in FIG. 22.

When $F^1$ is for example a ketone group, complementary groups $Q^1$ include (O-alkyl)hydroxylamino groups and hydrazine groups, and the corresponding connecting groups $Z^3$ are as shown in FIG. 22.

When $F^1$ is for example an alkynyl group, complementary groups $Q^1$ include azido groups, and the corresponding connecting group $Z^3$ is as shown in FIG. 22.

When $F^1$ is for example an azido group, complementary groups $Q^1$ include alkynyl groups, and the corresponding connecting group $Z^3$ is as shown in FIG. 22.

When $F^1$ is for example a cyclopropenyl group, a trans-cyclooctene group or a cyclooctyne group, complementary groups $Q^1$ include tetrazinyl groups, and the corresponding connecting group $Z^3$ is as shown in FIG. 22. In these particular cases, $Z^3$ is only an intermediate structure and will expel $N_2$, thereby generating a dihydropyridazine (from the reaction with alkene) or pyridazine (from the reaction with alkyne).

Additional suitable combinations of $F^1$ and $Q^1$, and the nature of resulting connecting group $Z^3$ are known to a person skilled in the art, and are e.g. described in G. T. Hermanson, "Bioconjugate Techniques", Elsevier, 3$^{rd}$ Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "Bioconjugate Techniques", Elsevier, 3$^{rd}$ Ed. 2013 (ISBN:978-0-12-382239-0), and the content of this Table is expressly incorporated by reference herein.

In the bioconjugate according to (5a) and (5b), it is preferred that at least one of $Z^3$, $Sp^3$, $Z^1$ and $Sp^2$ is present, i.e. at least one of h, g, d and c is not 0. It is also preferred that at least one of $Sp^1$, $Z^2$ and $Sp^4$ is present, i.e. that at least one of b, e and i is not 0. More preferably, at least one of $Z^3$, $Sp^3$, $Z^1$ and $Sp^2$ is present and at least one of $Sp^1$, $Z^2$ and $Sp^4$ is present, i.e. it is preferred that at least one of b, e and i is not 0 and at least one of h, g, d and c is not 0.

Process for the Preparation of a Bioconjugate

The present invention also relates to a process for the preparation of a bioconjugate, the process comprising the step of reacting a reactive group $Q^1$ of a linker-conjugate according to the invention with a functional group $F^1$ of a biomolecule. The linker-conjugate according to the invention, and preferred embodiments thereof, are described in more detail above.

FIG. 1 shows the general concept of conjugation of biomolecules: a biomolecule of interest (BOI) comprising one or more functional groups $F^1$ is incubated with (excess of) a target molecule D (also referred to as molecule of interest or MOI) covalently attached to a reactive group $Q^1$ via a specific linker. In the process of bioconjugation, a chemical reaction between $F^1$ and $Q^1$ takes place, thereby forming a bioconjugate comprising a covalent bond between the BOI and the MOI. The BOI may e.g. be a peptide/protein, a glycan or a nucleic acid. In the process according to the invention, the linker is a sulfamide linker.

The present invention thus relates to a process for the preparation of a bioconjugate, the process comprising the step of reacting a reactive group $Q^1$ of a linker-conjugate with a functional group $F^1$ of a biomolecule, wherein the linker-conjugate is a compound comprising an alpha-end and an omega-end, the compound comprising on the alpha-end a reactive group $Q^1$ capable of reacting with a functional group $F^1$ present on the biomolecule and on the omega-end a target molecule, the compound further comprising a group according to formula (1) or a salt thereof:

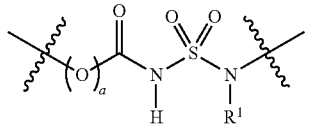

wherein:
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety;
and wherein the group according to formula (1), or the salt thereof, is situated in between said alpha-end and said omega-end of the linker conjugate.

In a preferred embodiment, the invention concerns a process for the preparation of a bioconjugate via a cycloaddition, such as a (4+2)-cycloaddition (e.g. a Diels-Alder reaction) or a (3+2)-cycloaddition (e.g. a 1,3-dipolar cycloaddition). Preferably, the conjugation is the Diels-Alder reaction or the 1,3-dipolar cycloaddition. The preferred Diels-Alder reaction is the inverse-electron demand Diels-Alder cycloaddition. In another preferred embodiment, the 1,3-dipolar cycloaddition is used, more preferably the alkyne-azide cycloaddition, and most preferably wherein $Q^1$ is or comprises an alkyne group and $F^1$ is an azido group. Cycloadditions, such as Diels-Alder reactions and 1,3-dipolar cycloadditions are known in the art, and the skilled person knows how to perform them. In a further preferred embodiment, the invention concerns a process for the preparation of a bioconjugate, wherein the target molecule is hydrophobic (i.e. weakly soluble in water), most preferably wherein the target molecule has a water solubility of at most 0.1% (w/w) in water (20° C. and 100 kPa). In an especially preferred embodiment, the invention concerns a process for the preparation of a bioconjugate via cycloaddition, preferably a 1,3-dipolar cycloaddition, more preferably the alkyne-azide cycloaddition, and most preferably wherein $Q^1$ is or comprises an alkyne group and $F^1$ is an azido group, and wherein the target molecule is hydrophobic, most preferably wherein the target molecule has a water solubility of at most 0.1% (w/w) in water (20° C. and 100 kPa).

In the process according to the invention, $Q^1$ reacts with $F^1$, forming a covalent connection between the biomolecule and the linker-moiety. Complementary reactive groups $Q^1$ and functional groups $F^1$ are described in more detail above and below.

In a preferred embodiment of the process according to the invention, a is 0 in the group according to formula (1). In this embodiment, the linker-conjugate thus comprises a group according to formula (2), as defined above. In another preferred embodiment of the process according to the invention, a is 1 in the group according to formula (1). In this embodiment, the linker-conjugate thus comprises a group according to formula (3), as defined above.

Biomolecules are described in more detail above. Preferably, in the process according to the invention the biomolecule is selected from the group consisting of proteins (including glycoproteins and antibodies), polypeptides, peptides, glycans, lipids, nucleic acids, oligonucleotides, polysaccharides, oligosaccharides, enzymes, hormones, amino acids and monosaccharides. More preferably, biomolecule B is selected from the group consisting of proteins (including glycoproteins and antibodies), polypeptides, peptides, glycans, nucleic acids, oligonucleotides, polysaccharides, oligosaccharides and enzymes. Most preferably, biomolecule B is selected from the group consisting of proteins, including glycoproteins and antibodies, polypeptides, peptides and glycans.

Target molecules are described in more detail above. In a preferred embodiment of the process according to the invention, the target molecule is selected from the group consisting of an active substance, a reporter molecule, a polymer, a solid surface, a hydrogel, a nanoparticle, a microparticle and a biomolecule. Active substances, reporter molecules, polymers, solid surfaces, hydrogels, nanoparticles and microparticles are described in detail above, as are their preferred embodiments. In view of the significantly improved water solubility of the linker-conjugate when the sulfamide linker according to the invention is employed, a preferred embodiment of the process for the preparation of a bioconjugate employs a hydrophobic target molecule. The hydrophobic target molecule in its unconjugated form typically has a water solubility of at most 1% (w/w), preferably at most 0.1% (w/w), most preferably at most 0.01% (w/w), determined at 20° C. and 100 kPa.

In the process according to the invention, it is preferred that reactive group $Q^1$ is selected from the group consisting of, optionally substituted, N-maleimidyl groups, halogenated N-alkylamido groups, sulfonyloxy N-alkylamido groups, ester groups, carbonate groups, sulfonyl halide groups, thiol groups or derivatives thereof, alkenyl groups, alkynyl groups, (hetero)cycloalkynyl groups, bicyclo[6.1.0]non-4-yn-9-yl]groups, cycloalkenyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, halogenated N-maleimidyl groups, 1,1-bis(sulfonylmethyl)methylcarbonyl groups or elimination derivatives thereof, carbonyl halide groups and allenamide groups.

In a further preferred embodiment, $Q^1$ is according to formula (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm) or (9zn), wherein (9a), (9b), (9c), (9d), (9e), (9f), (9g), (9h), (9i), (9j), (9k), (9l), (9m), (9n), (9o), (9p), (9q), (9r), (9s), (9t), (9u), (9v), (9w), (9x), (9y), (9z), (9za), (9zb), (9zc), (9zd), (9ze), (9zf), (9zg), (9zh), (9zi), (9zj), (9zk), (9zl), (9zm), (9zn) and preferred embodiments thereof, are as defined above for the linker-conjugate according to the invention. More preferably, $Q^1$ is according to formula (9a), (9b), (9c), (9f), (9j), (9n), (9o), (9p), (9q), (9s), (9t), (9zh), (9r), (9zl), (9zm) or (9zn). Even more preferably, $Q^1$ is according to formula (9a), (9n), (9o), (9p), (9q), (9t), (9zh) or (9s), and most preferably, $Q^1$ is according to formula (9a), (9p), (9q), (9n), (9t), (9zh) or (9o), and preferred embodiments thereof, as defined above.

In an especially preferred embodiment, $Q^1$ comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably $Q^1$ is selected from the formulae (9j), (9n), (9o), (9p), (9q) and (9zk), as defined above. Most preferably, $Q^1$ is a bicyclo [6.1.0]non-4-yn-9-yl] group, preferably of formula (9q).

In a further preferred embodiment of the process according to the invention, the linker-conjugate is according to formula (4a) or (4b), or a salt thereof:

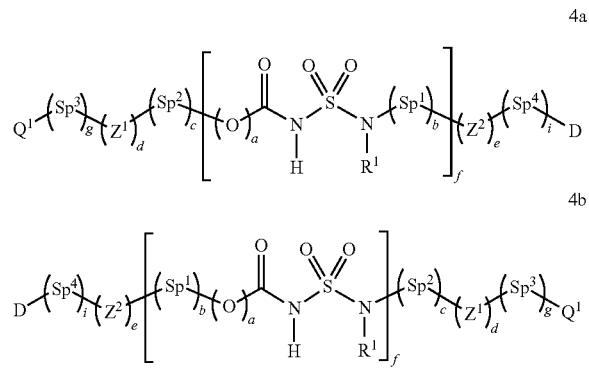

wherein:
a is independently 0 or 1;
b is independently 0 or 1;
c is 0 or 1;
d is 0 or 1;
e is 0 or 1;
f is an integer in the range of 1 to 150;
g is 0 or 1;
i is 0 or 1;
D is a target molecule;
$Q^1$ is a reactive group capable of reacting with a functional group $F^1$ present on a biomolecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or $N(R^1)$;
$Z^2$ is a connecting group that connects D or $Sp^4$ to $Sp^1$, $N(R^1)$, O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero) arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or
$R^1$ is D, -[$(Sp^1)_b$-$(Z^2)_e$—$(Sp^4)_i$-D] or -[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above.

$Sp^1$, $Sp^2$, $Sp^3$ and $Sp^4$ are, independently, spacer moieties, in other words, $Sp^1$, $Sp^2$, $Sp^3$ and $Sp^4$ may differ from each other. $Sp^1$, $Sp^2$, $Sp^3$ and $Sp^4$ may be present or absent (b, c, g and i are, independently, 0 or 1). However, it is preferred that at least one of $Sp^1$, $Sp^2$, $Sp^3$ and $Sp^4$ is present, i.e. it is preferred that at least one of b, c, g and i is not 0.

If present, preferably $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$, $Sp^2$, $Sp^3$ and $Sp^4$, if present, are independently selected from the group consisting of linear or branched $C_1$-$C_{100}$ alkylene groups, $C_2$-$C_{100}$ alkenylene groups, $C_2$-$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_9$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$, $Sp^2$, $Sp^3$ and $Sp^4$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_5$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$, $Sp^2$, $Sp^3$ and $Sp^4$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^3$, preferably 0, wherein $R^3$ is independently selected from the group consisting of hydrogen and $C_1$-$C_4$ alkyl groups, preferably hydrogen or methyl.

Most preferably, spacer moieties $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^3$, preferably O and/or S—S, wherein $R^3$ is independently selected from the group consisting of hydrogen and $C_1$-$C_4$ alkyl groups, preferably hydrogen or methyl.

Particularly preferred spacer moieties $Sp^1$, $Sp^2$, $Sp^3$ and $Sp^4$ include —$(CH_2)_n$—, —$(CH_2CH_2)_n$—, —$(CH_2CH_2O)_n$—, —$(OCH_2CH_2)_n$—, —$(CH_2CH_2O)_nCH_2CH_2$—, —$CH_2CH_2(OCH_2CH_2)_n$—, —$(CH_2CH_2CH_2O)_n$—, —$(OCH_2CH_2CH_2)_n$—, —$(CH_2CH_2CH_2O)_nCH_2CH_2CH_2$— and —$CH_2CH_2CH_2(OCH_2CH_2CH_2)_n$—, wherein n is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

In another preferred embodiment of the process according to the invention, in the linker-conjugates according to formula (4a) and (4b), spacer moieties $Sp^1$, $Sp^2$, $Sp^3$ and/or $Sp^4$, if present, comprise a sequence of amino acids. Spacer-moieties comprising a sequence of amino acids are known in the art, and may also be referred to as peptide linkers. Examples include spacer-moieties comprising a Val-Cit moiety, e.g. val-cit-PABC, val-cit-PAB Fmoc-val-cit-PAB, etc.

As described above, $Z^1$ and $Z^2$ are a connecting groups. In a preferred embodiment of the process according to the invention, $Z^1$ and $Z^2$ are independently selected from the group consisting of —O—, —S—, —$NR^2$—, —N=N—, —C(O)—, —C(O)$NR^2$—, —O—C(O)—, —O—C(O)—O—, —O—C(O)—$NR^2$, —$NR^2$—C(O)—, —$NR^2$—C(O)—O—, —$NR^2$—C(O)—$NR^2$—, —S—C(O)—, —S—C(O)—O—, —S—C(O)—$NR^2$—, —S(O)—, —S(O)$_2$—, —O—S(O)$_2$—, —O—S(O)$_2$—O—, —O—S(O)$_2$—$NR^2$—, —O—S(O)—, —O—S(O)—O—, —O—S(O)—$NR^2$—, —O—$NR^2$—C(O)—, —O—$NR^2$—C(O)—O—, —O—$NR^2$—C(O)—$NR^2$—, —$NR^2$—O—C(O)—, —$NR^2$—O—C(O)—O—, —$NR^2$—O—C(O)—$NR^2$—, —O—$NR^2$—C(S)—, —O—$NR^2$—C(S)—O—, —O—$NR^2$—C(S)—$NR^2$—, —$NR^2$—O—C(S)—, —$NR^2$—O—C(S)—O—, —$NR^2$—O—C(S)—$NR^2$—, —O—C(S)—, —O—C(S)—O—, —O—C(S)—$NR^2$—, —$NR^2$—C(S)—, —$NR^2$—C(S)—O—, —$NR^2$—C(S)—$NR^2$—, —S—S(O)$_2$—, —S—S(O)$_2$—O—, —S—S(O)$_2$—$NR^2$—, —$NR^2$—O—S(O)—, —$NR^2$—O—S(O)—O—, —$NR^2$—O—S(O)—$NR^2$—, —$NR^2$—O—S(O)$_2$—, —$NR^2$—O—S(O)$_2$—O—, —$NR^2$—O—S(O)$_2$—$NR^2$—, —O—$NR^2$—S(O)—, —O—$NR^2$—S(O)—O—, —O—$NR^2$—S(O)—$NR^2$—, —O—$NR^2$—S(O)$_2$—O—, —O—$NR^2$—S(O)$_2$—$NR^2$—, —O—$NR^2$—S(O)$_2$—, —O—P(O)($R^2$)$_2$—, —S—P(O)($R^2$)$_2$—, —$NR^2$—P(O)($R^2$)$_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In a particularly preferred process according to the invention, $Sp^1$, $Sp^2$, $Sp^3$ and $Sp^4$, if present, are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, wherein $R^3$ is independently selected from the group consisting of hydrogen and $C_1$-$C_4$ alkyl groups, and wherein $Q^1$ is according to formula (9a), (9p), (9q), (9n), (9t), (9zh) or (9o):

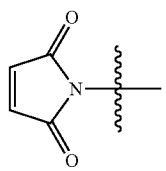

9a

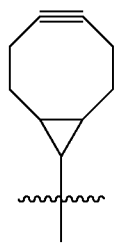

9q

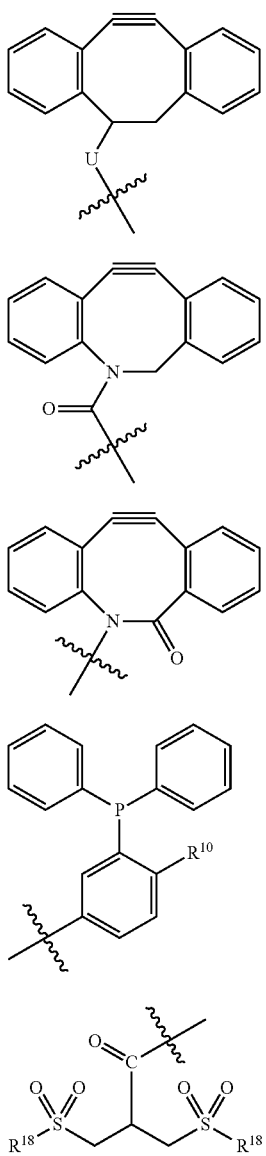

wherein:

R$^{10}$ is hydrogen or a (thio)ester group; and
R$^{18}$ is selected from the group consisting of, optionally substituted, C$_1$-C$_{12}$ alkyl groups and C$_4$-C$_{12}$ (hetero)aryl groups.

As described above, in the process for the preparation of a bioconjugate, a reactive group Q$^1$ that is present in a linker-conjugate is reacted with a functional group F$^1$ that is present in a biomolecule. In the process according to the invention, more than one functional group may be present in the biomolecule. When two or more functional groups are present, said groups may be the same or different. Similarly, more than one reactive group may be present in the linker-conjugate. When two or more reactive groups are present, said groups may be the same or different. In a preferred embodiment of the process according to the invention, the linker-conjugate comprises one reactive group Q$^1$, and one or more target molecules D which may be the same or different. The linker-conjugate comprises for example 1, 2, 3, 4, 5 or 6, preferably 1, 2, 3 or 4, more preferably 1, 2 or 3, even more preferably 1 or 2 target molecule D. In a particularly preferred embodiment the linker-conjugate comprises 1 target molecule D. In another particularly preferred embodiment, the linker-conjugate comprises 2 target molecules D, which may be the same or different. In another preferred embodiment, the biomolecule comprises two or more functional groups F, which may be the same or different, and two or more functional groups react with a complementary reactive group Q of a linker-conjugate. For example a biomolecule comprising two functional groups F, i.e. F$^1$ and F$^2$, may react with two linker-conjugates comprising a functional group Q$^1$, which may be the same or different, to form a bioconjugate.

Examples of a functional group F$^1$ in a biomolecule comprise an amino group, a thiol group, a carboxylic acid, an alcohol group, a carbonyl group, a phosphate group, or an aromatic group. The functional group in the biomolecule may be naturally present or may be placed in the biomolecule by a specific technique, for example a (bio)chemical or a genetic technique. The functional group that is placed in the biomolecule may be a functional group that is naturally present in nature, or may be a functional group that is prepared by chemical synthesis, for example an azide, a terminal alkyne, a cyclopropene moiety or a phosphine moiety. In view of the preferred mode of conjugation by cycloaddition, it is preferred that F$^1$ is group capable of reacting in a cycloaddition, such as a diene, a dienophile, a 1,3-dipole or a dipolarophile, preferably F$^1$ is selected from a 1,3-dipole (typically an azido group, nitrone group, nitrile oxide group, nitrile imine group or diazo group) or a dipolarophile (typically an alkenyl or alkynyl group). Herein, F$^1$ is a 1,3-dipole when Q$^1$ is a dipolarophile and F$^1$ is a dipolarophile when Q$^1$ is a 1,3-dipole, or F$^1$ is a diene when Q$^1$ is a dienophile and F$^1$ is a dienophile when Q$^1$ is a diene. Most preferably, F$^1$ is a 1,3-dipole, preferably F$^1$ is or comprises an azido group.

Figure 2:
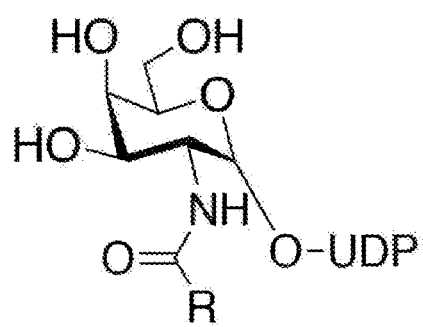
FIG. 2 shows several structures of derivatives of UDP sugars of galactosamine, which may be modified with e.g. a 3-mercaptopropionyl group (11a), an azidoacetyl group (11b), or an azidodifluoroacetyl group (11c).

Several examples of a functional group that is placed into a biomolecule are shown in FIG. 2. FIG. 2 shows several structures of derivatives of UDP sugars of galactosamine, which may be modified with e.g. a thiopropionyl group (11a), an azidoacetyl group (11b), or an azidodifluoroacetyl group (11c).

Figure 3:
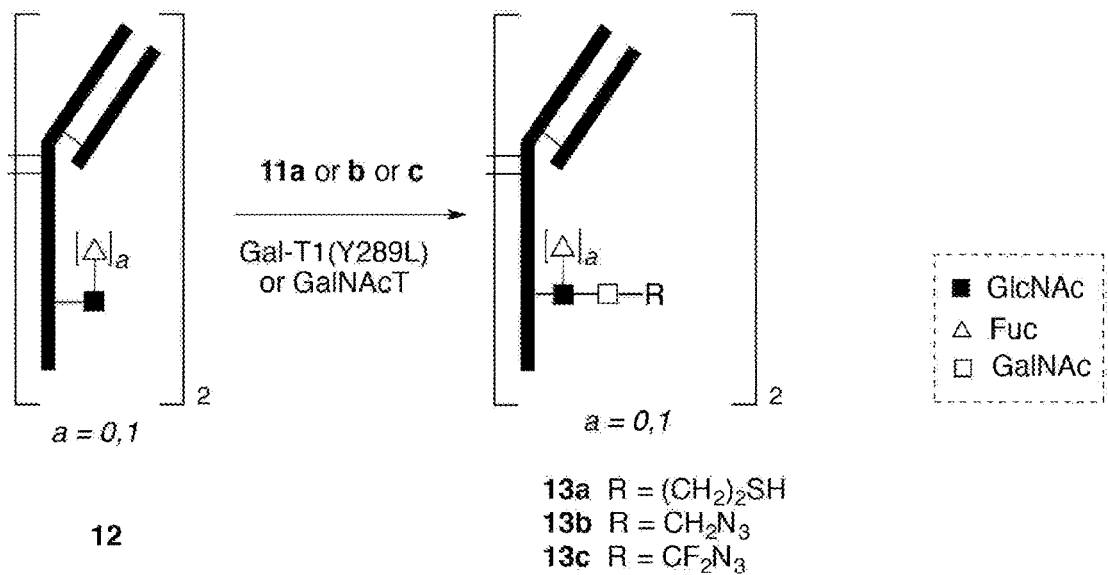
FIG. 3 schematically displays how any of the UDP-sugars 11a-c may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a (3-glycosidic 1-4 linkage between a GalNAc derivative and GlcNAc (compounds 13a-c, respectively).

FIG. 3 schematically displays how any of the UDP-sugars 11a-c may be attached to a glycoprotein comprising a GlcNAc moiety 12 (e.g. a monoclonal antibody the glycan of which is trimmed by an endoglycosidase) under the action of a galactosyltransferase mutant or a GalNAc-transferase, thereby generating a (3-glycosidic 1-4 linkage between a GalNAc derivative and GlcNAc (compounds 13a-c, respectively).

Preferred examples of naturally present functional groups F$^1$ include a thiol group and an amino group. Preferred examples of a functional group that is prepared by chemical synthesis for incorporation into the biomolecule include a ketone group, a terminal alkyne group, an azide group, a cyclo(hetero)alkyne group, a cyclopropene group, or a tetrazine group.

As was described above, complementary reactive groups Q$^1$ and functional groups F$^1$ are known to a person skilled in the art, and several suitable combinations of Q$^1$ and F$^1$ are described above, and shown in FIG. 22. A list of complementary groups Q$^1$ and F$^1$ is disclosed in in Table 3.1, pages 230-232 of Chapter 3 of G. T. Hermanson, "*Bioconjugate Techniques*", Elsevier, 3$^{rd}$ Ed. 2013 (ISBN:978-0-12-382239-0), and the content of this Table is expressly incorporated by reference herein.

Figure 4:
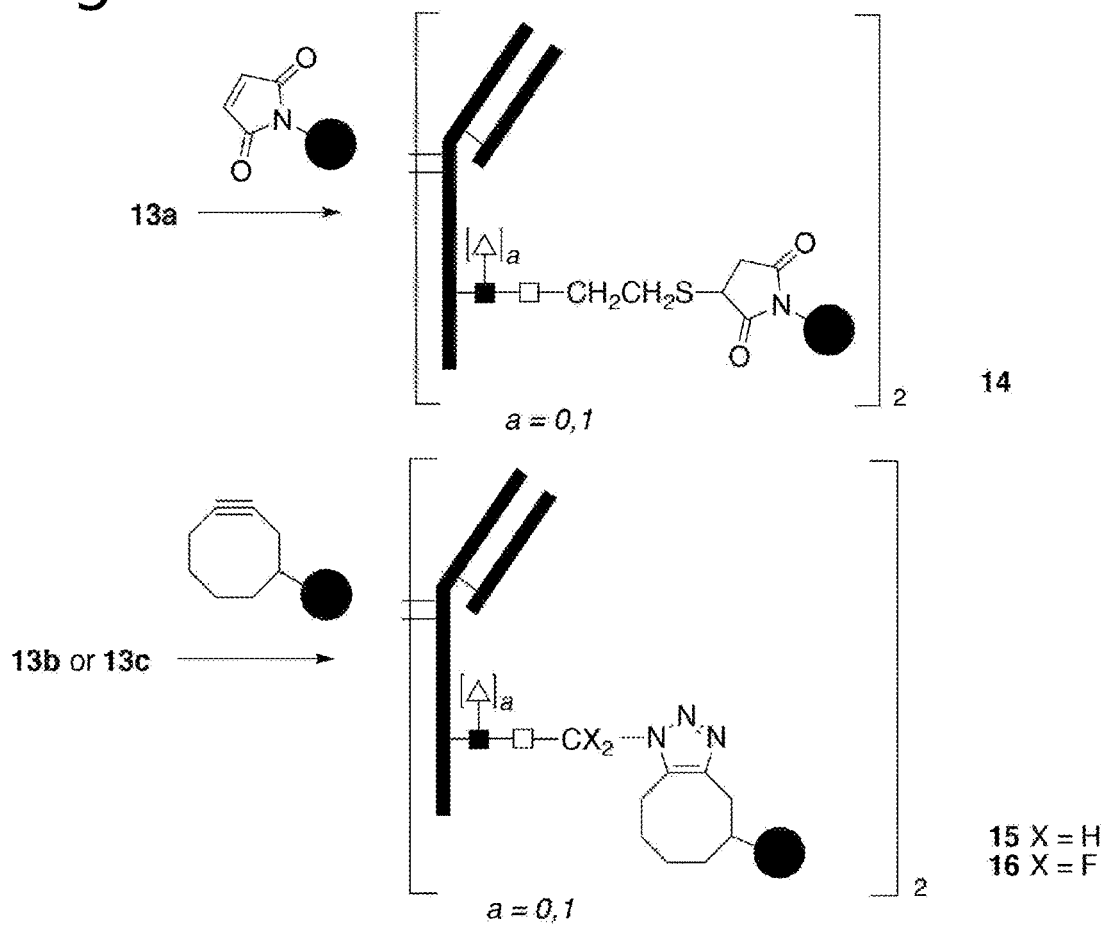
FIG. 4 shows how a modified antibody 13a-c may undergo a bioconjugation process by means of nucleophilic addition to maleimide (as for 13a, leading to thioether conjugate 14) or upon strain-promoted cycloaddition with a cyclooctyne reagent (as for 13b or 13c, leading to triazoles 15 or 16, respectively).

An embodiment of the process according to the invention is depicted in FIG. 4. FIG. 4 shows how a modified antibody 13a-c may undergo a bioconjugation process by means of nucleophilic addition with maleimide (as for 13a, leading to thioether conjugate 14) or upon strain-promoted cycloaddition with a cyclooctyne reagent (as for 13b or 13c, leading to triazoles 15 or 16, respectively).

The invention further relates to a bioconjugate obtainable by the process according to the invention for the preparation of a bioconjugate.

An advantage of the process according to the invention for the preparation of a bioconjugate, and of the linker-conjugate and sulfamide linker according to the invention is that conjugation efficiency increases in case a sulfamide linker is used instead of a typical polyethylene glycol (PEG) spacer. For example, as demonstrated in example 58, a competition experiment involving incubation of trastuzumab containing a single engineered free cysteine with a stoichiometric mixture of maleimide 17 (comprising a comparative linker) and 18 (comprising a sulfamide linker according to the invention) demonstrated that conjugation efficiency of the sulfamide-containing maleimide 18 is higher than with 17.

Figure 5:
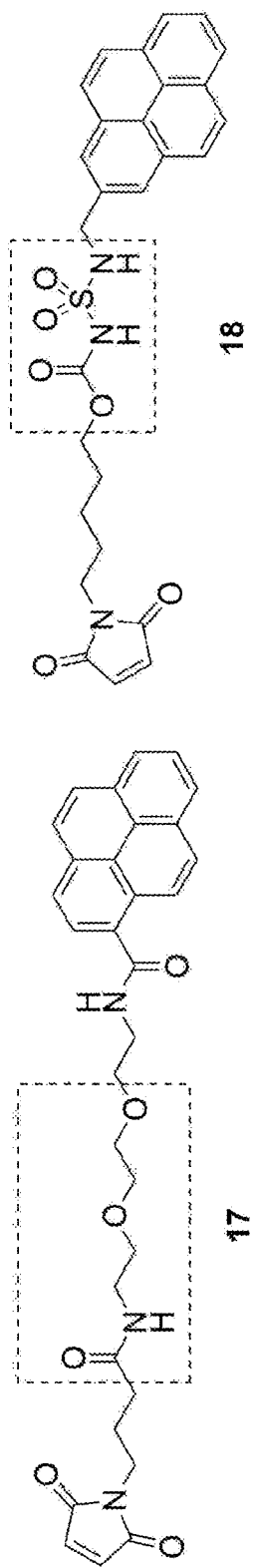
FIG. 5 shows the structures of several compounds wherein an N-maleimidyl reactive group $Q^1$ is connected to a pyrene group (D) via a linker unit.
Figure 16:
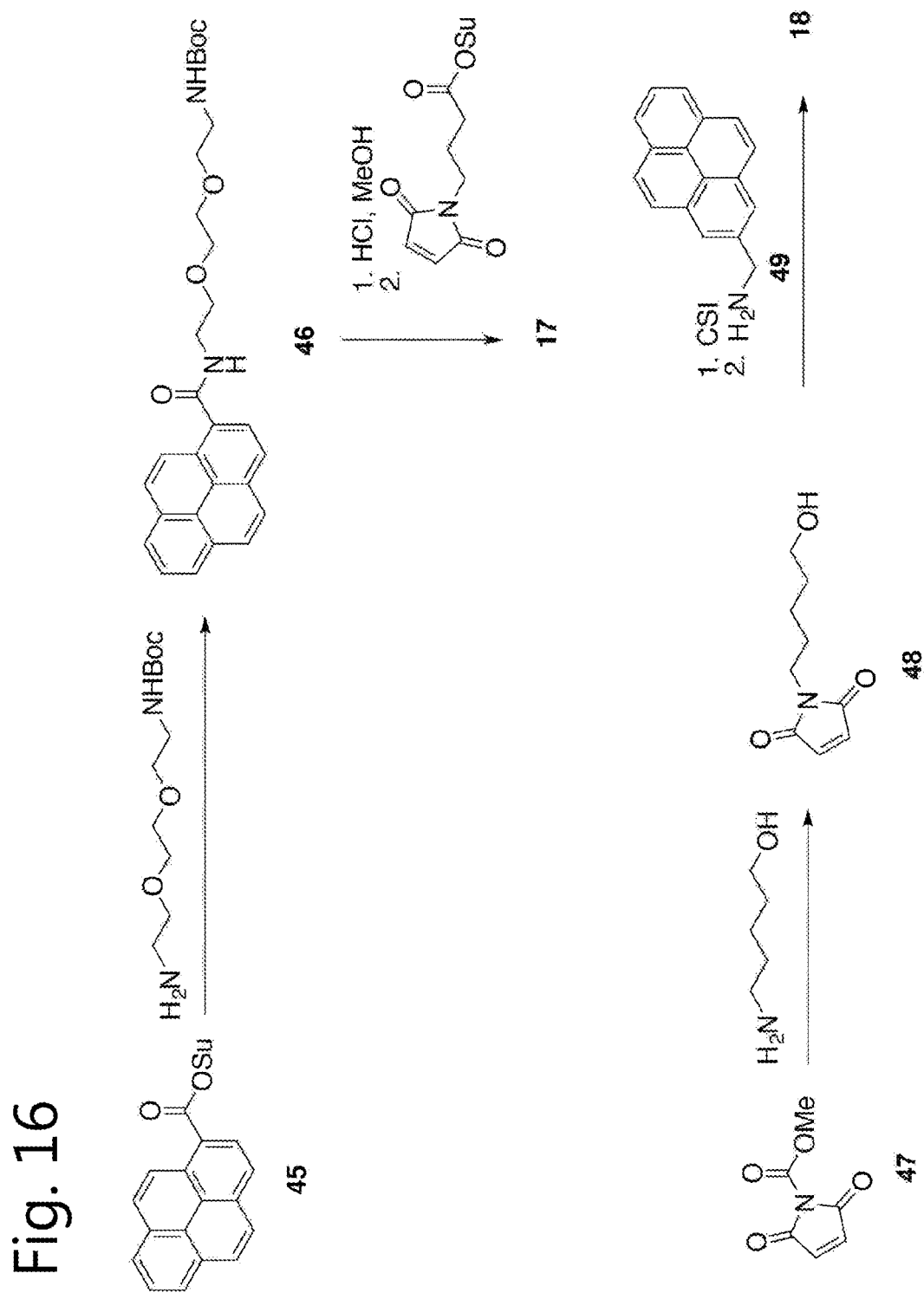
FIG. 16 shows the synthesis of several linker-conjugates wherein $Q^1$ is an N-maleimidyl group and D is a pyrene. Compound 18 is according to the invention, whereas compound 17 is a comparative example.

FIG. 5 shows the structure of linker-conjugates 17 and 18, wherein $Q^1$ is an N-maleimidyl group and D is a pyrene. Compound 18 is according to the invention, whereas compound 17 is a comparative example. FIG. 16 shows the synthesis of 17 and 18.

Likewise, conjugations of 19-35, depicted in FIGS. 6-9, with trastuzumab-$N_3$ show that a conjugation process based on azide-cyclooctyne cycloaddition is invariably faster for sulfamide-containing linker-conjugates in comparison to the traditional PEG-containing linker conjugates, and in most cases dramatically faster (see Table 1 and 2 and FIGS. 12-14).

Conjugates of 20, 21, 23, 26, 29, 33 and 35 with trastuzumab-$N_3$ are according to the invention, and conjugates of 19, 22, 24, 25, 27, 28, 30, 31, 32 and 34 are comparative examples. Moreover, in several instances conjugations with PEG-based constructs do not reach full conversion, even after prolonged incubation times, e.g. FIGS. 12a, 12b, 13b and 14a.

TABLE 1

| Compound | Conversion (%) | | | | | |
| --- | --- | --- | --- | --- | --- | --- |
| | 30' | 60' | 90' | 120' | 240' | 960' |
| 19 (comp.) | 0 | 0 | n.d. | n.d. | 10 | n.d. |
| 20 | 80 | 90 | n.d. | 95 | >95 | n.d. |
| 21 | n.d. | 60 | n.d. | n.d. | 90 | n.d. |
| 22 (comp.) | 0 | 5 | n.d. | 10 | 30 | n.d. |
| 23 | 20 | 30 | n.d. | 70* | >90* | n.d. |
| 24 (comp.) | 0 | 10 | 20 | 30 | n.d. | 80 |
| 25 (comp.) | 20 | 20 | 30 | 60 | n.d. | 80 |
| 26 | 70 | 80 | 85 | 95 | n.d. | 100 |
| 27 (comp.) | 20 | 25 | 30 | 30 | n.d. | 30 |
| 28 (comp.) | 30 | 40 | 60 | 65 | n.d. | 65 |
| 29 | 60 | 70 | 80 | 85 | n.d. | 90 |
| 30 (comp.) | 75 | >90 | n.d. | >95 | n.d. | >95 |
| 31 (comp.) | 25 | 45 | n.d. | 60 | n.d. | 95 |
| 32 (comp.) | 20 | 35 | n.d. | 70 | n.d. | 85 |
| 33 | 85 | 95 | n.d. | >95 | n.d. | >95 |
| 34 (comp.) | 25 | 50 | n.d. | 75 | n.d. | 95 |
| 35 | 95 | >95 | n.d. | >95 | n.d. | >95 |

*Based on remaining starting trastuzumab-$N_3$.
n.d. = not determined

TABLE 2

| compound | conversion (%) | | | | |
| --- | --- | --- | --- | --- | --- |
| | 30' | 60' | 120' | 240' | 3600' |
| 30 (comp.) | 25 | 40 | 65 | 95 | 95 |
| 31 (comp.) | 5 | 10 | 15 | 50 | 50 |
| 32 (comp.) | <5 | 5 | 10 | 80 | 80 |
| 33 | 25 | 40 | 65 | 95 | 95 |
| 34 (comp.) | <5 | <5 | 5 | 85 | 85 |
| 35 | 80 | 90 | 95 | >95 | >95 |

Figure 12A:
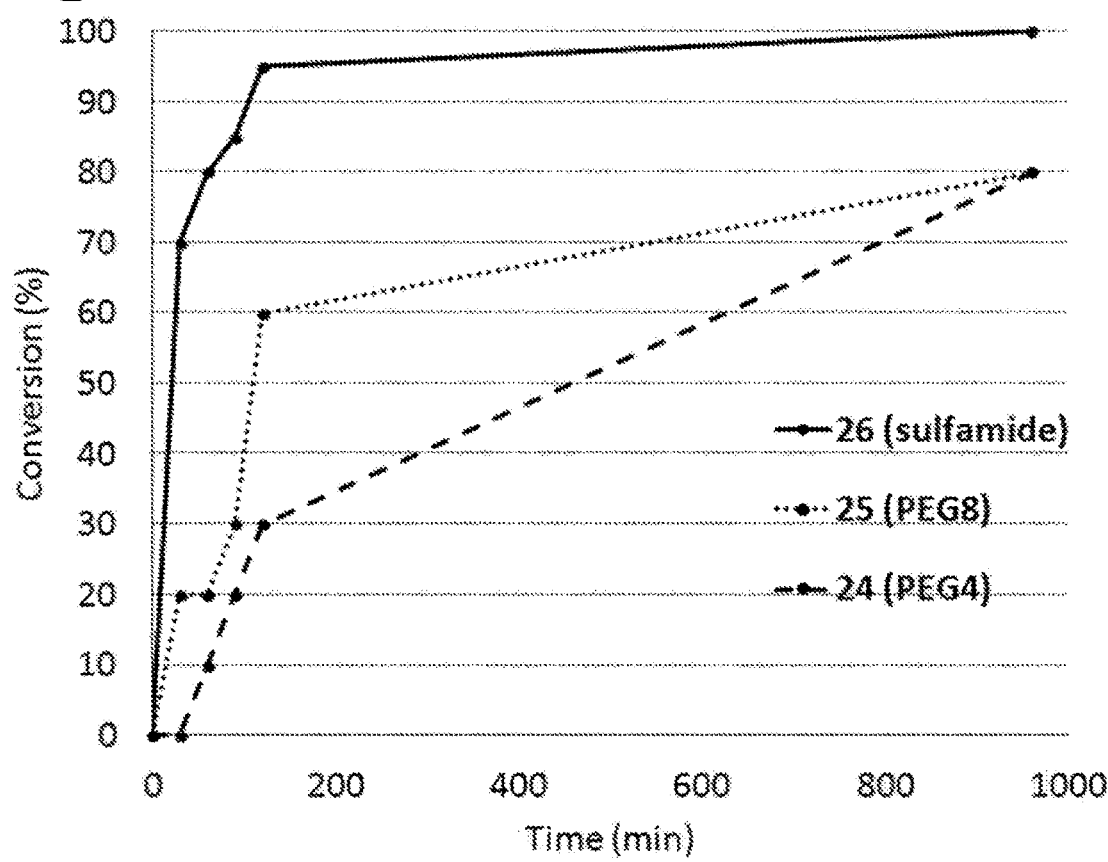
FIG. 12a shows the conjugation efficiency of BCN-pyrene derivatives conjugated via a sulfamide linker (compound 26) or short PEG linker (compounds 24 or 25) with trastuzumab-$N_3$ (compound 13b).

FIG. 12a shows the conjugation efficiency of BCN-pyrene derivatives conjugated via a sulfamide linker (compound 26) or short PEG linkers (compounds 24 or 25) with trastuzumab-$N_3$ (compound 13b).

Figure 12B:
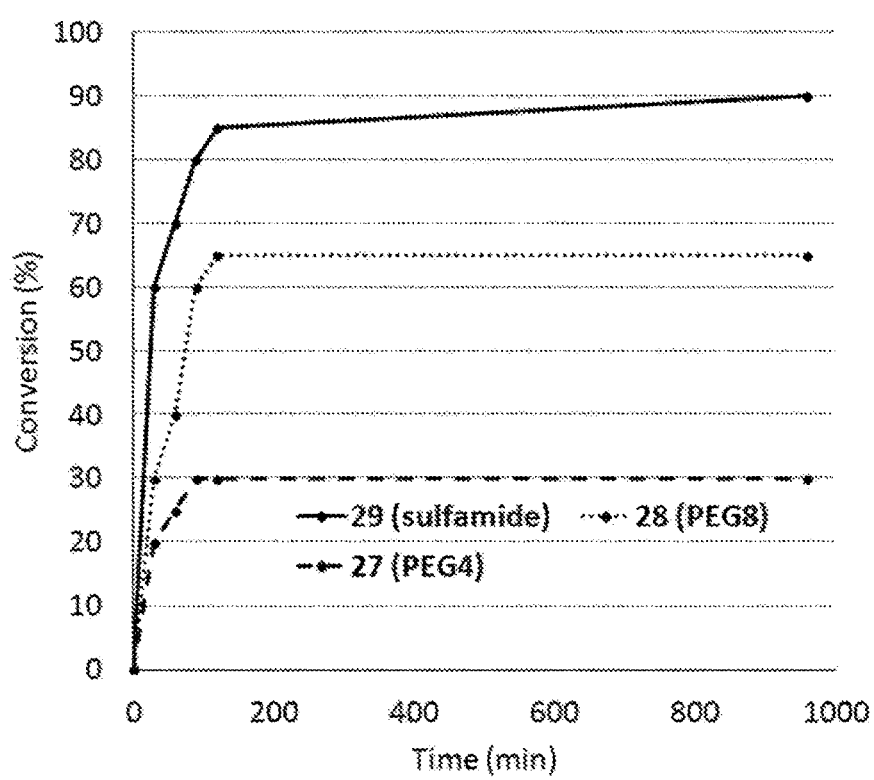
FIG. 12b shows the conjugation efficiency of DIBAC-pyrene derivatives conjugated via a sulfamide linker (compound 29) or short PEG linker (compounds 27 or 28) with trastuzumab-$N_3$ (compound 13b).

FIG. 12b shows the conjugation efficiency of DIBAC-pyrene derivatives conjugated via a sulfamide linker (compound 29) or short PEG linkers (compounds 27 or 28) with trastuzumab-$N_3$ (compound 13b).

Figure 13A:
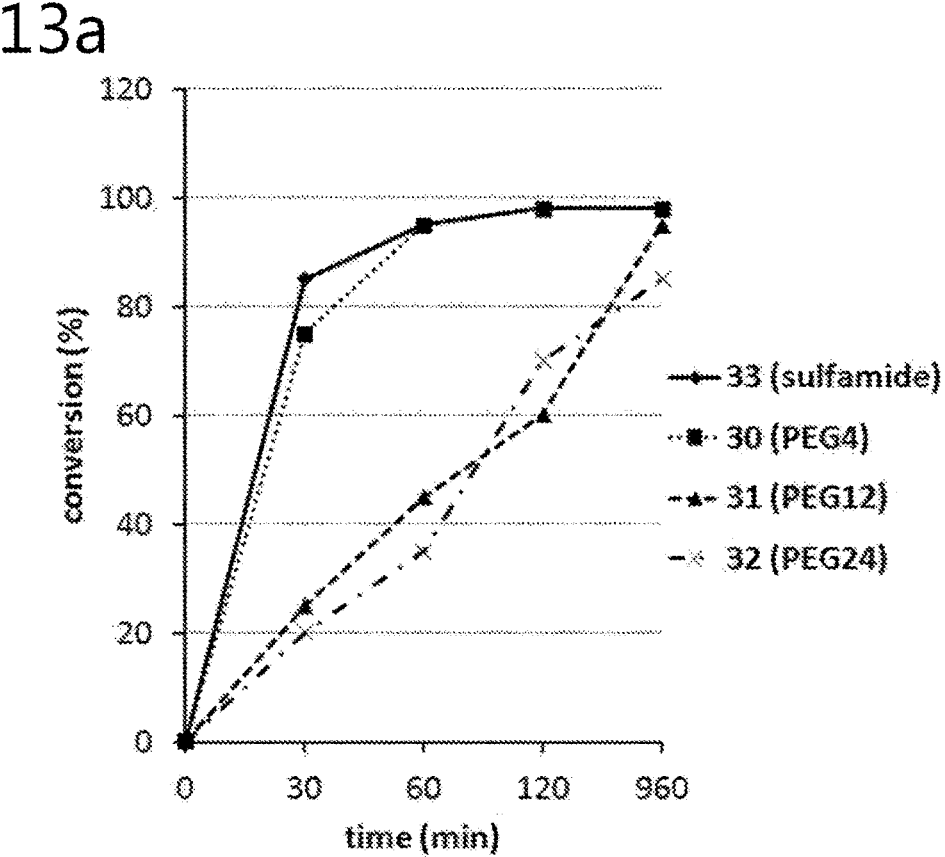
FIG. 13a shows the conjugation efficiency of BCN-maytansin derivatives conjugated via a sulfamide linker (compound 33) or short PEG linker (compounds 30-32) with trastuzumab-$N_3$ (compound 13b).

FIG. 13a shows the conjugation efficiency of BCN-maytansin derivatives conjugated via a sulfamide linker (compound 33) or short PEG linkers (compounds 30-32) with trastuzumab-$N_3$ (compound 13b).

Figure 13B:
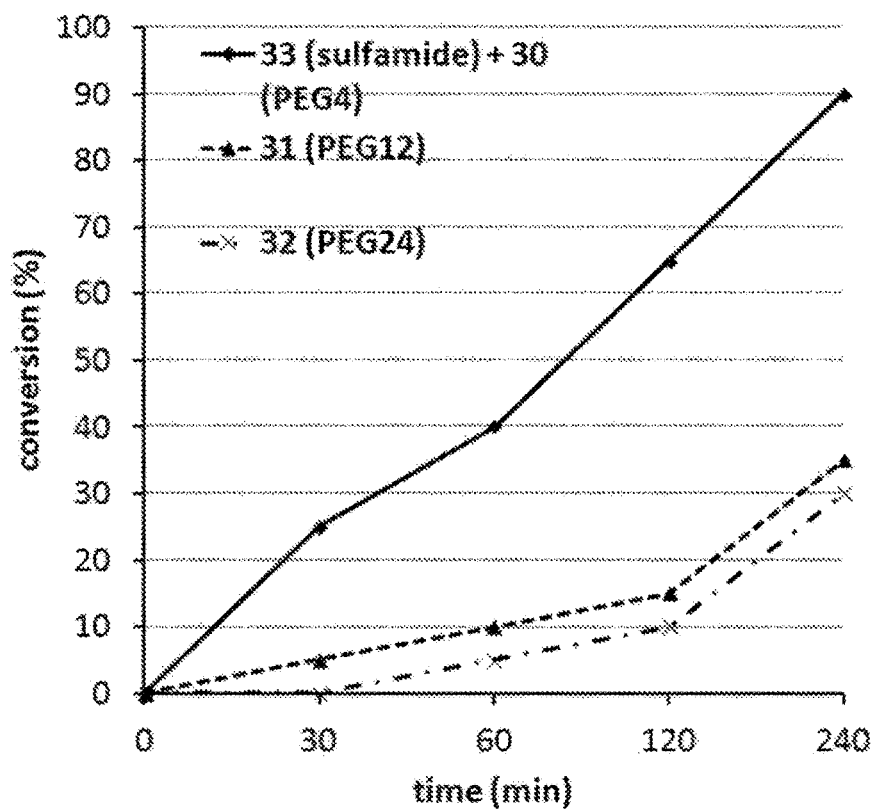
FIG. 13b shows the conjugation efficiency of BCN-maytansin derivatives conjugated via a sulfamide linker (compounds 33) or short PEG linker (compounds 30-32, with compound 30 overlapping with 33) with trastuzumab-$F_2$-GalNAz (compound 13c).

FIG. 13b shows the conjugation efficiency of BCN-maytansin derivatives conjugated via a sulfamide linker (compounds 33) or short PEG linkers (compounds 30-32, with compound 30 overlapping with 33) with trastuzumab-$F_2$-GalNAz (compound 13c).

Figure 14A:
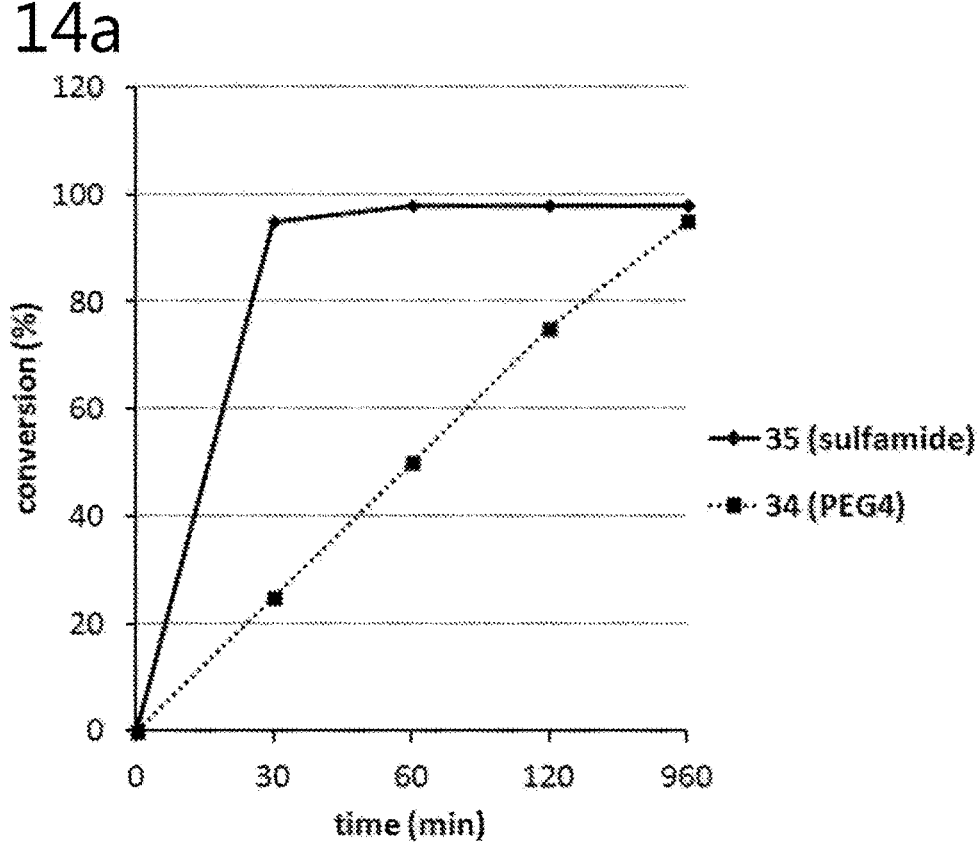
FIG. 14a shows the conjugation efficiency of BCN-duocarmycin derivatives conjugated via a sulfamide linker (compound 35) or short PEG linker (compound 34) with trastuzumab-$N_3$ (compound 13b).

FIG. 14a shows the conjugation efficiency of BCN-duocarmycin derivatives conjugated via a sulfamide linker (compound 35) or short PEG linker (compound 34) with trastuzumab-$N_3$ (compound 13b).

Figure 14B:
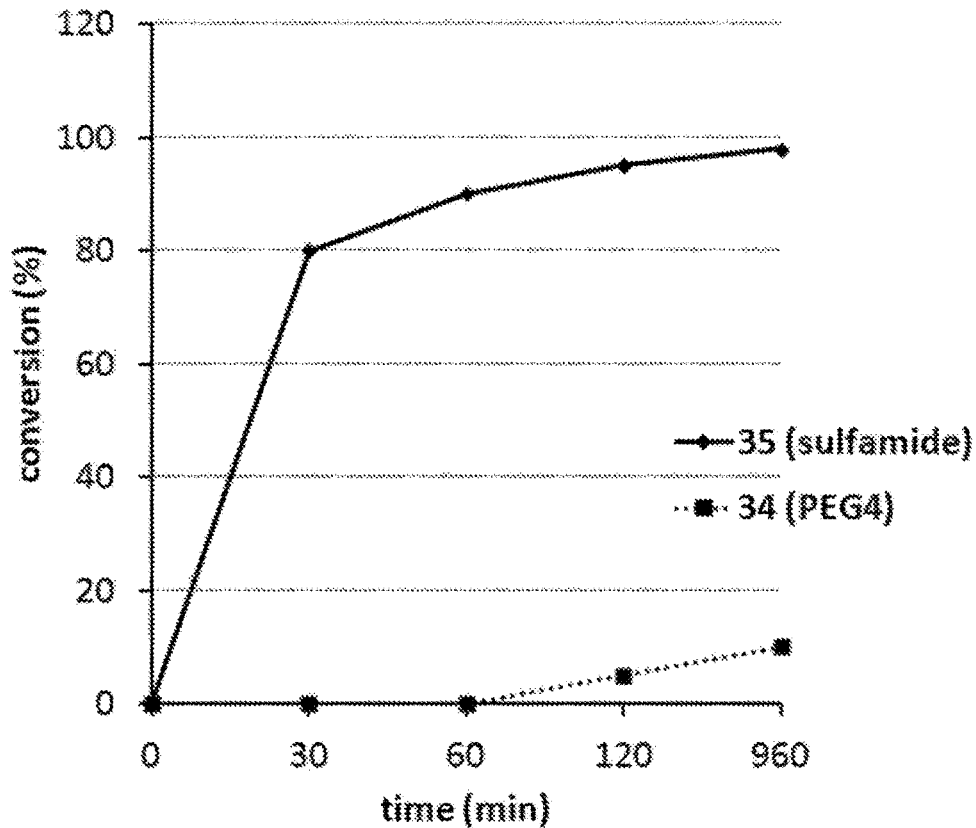
FIG. 14b shows the conjugation efficiency of BCN-duocarmycin derivatives conjugated via a sulfamide linker (compound 35) or short PEG linker (compound 34) with trastuzumab-$F_2$-GalNAz (compound 13c).

FIG. 14b shows the conjugation efficiency of BCN-duocarmycin derivatives conjugated via a sulfamide linker (compound 35) or short PEG linker (compound 34) with trastuzumab-$F_2$-GalNAz (compound 13c).

An additional advantage of a sulfamide group, in particular of an acylsulfamide or a carbamoylsulfamide group, is its high polarity, which imparts a positive effect on the solubility of a linker comprising such group, and on the construct as a whole, before, during and after conjugation. The increased polarity of the sulfamide spacer becomes clear from Table 3 (graphically depicted in FIG. 11), which summarizes the retention times of compounds 19-23 and 30-38 on RP-HPLC. In view of this increased polarity, conjugation with linker-conjugates containing the sulfamide linker according to the invention are particularly suited to conjugate hydrophobic target compounds to a biomolecule.

Figure 11:
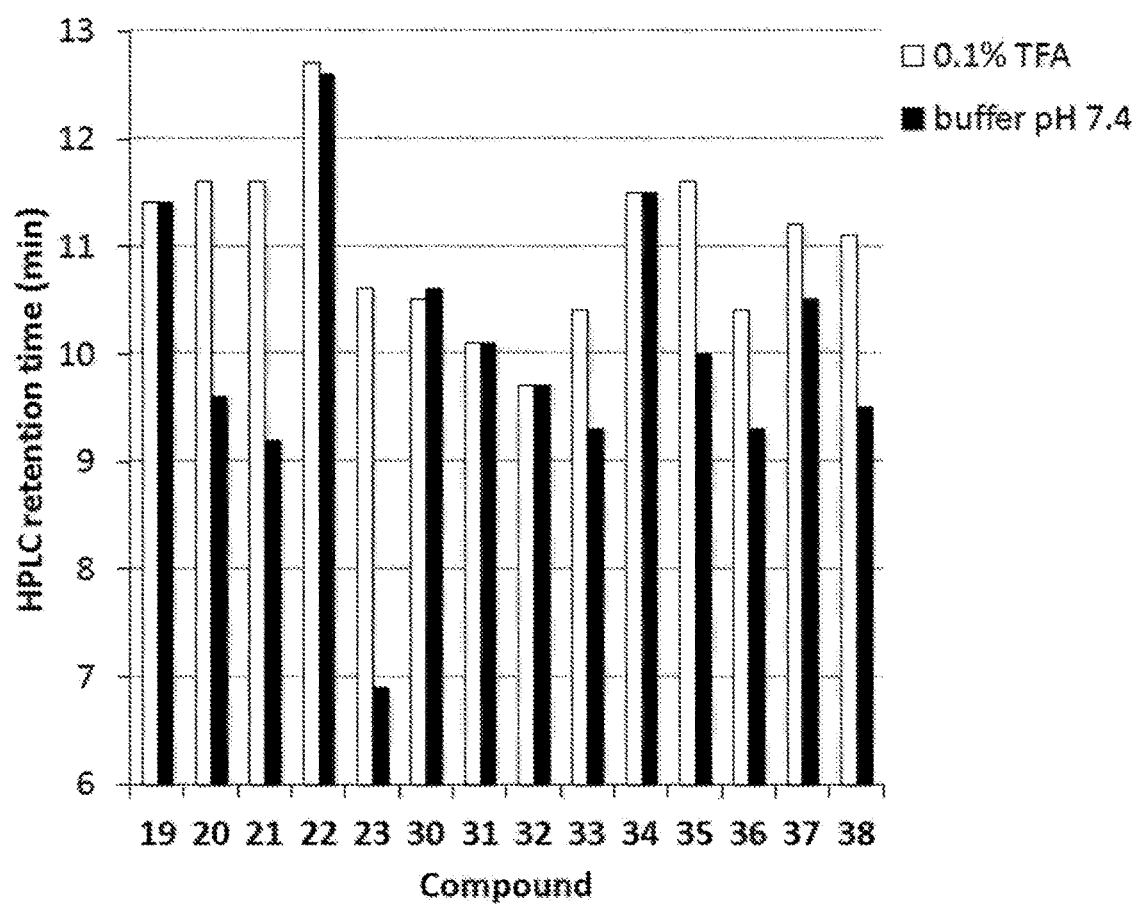
FIG. 11 shows the HPLC retention times of compounds 19-23 and 30-38 with 0.1% TFA or in buffer pH 7.4.

FIG. 11 shows the HPLC retention times of compounds 19-23 and 30-38 with 0.1% TFA or in buffer pH 7.4.

Figure 6:
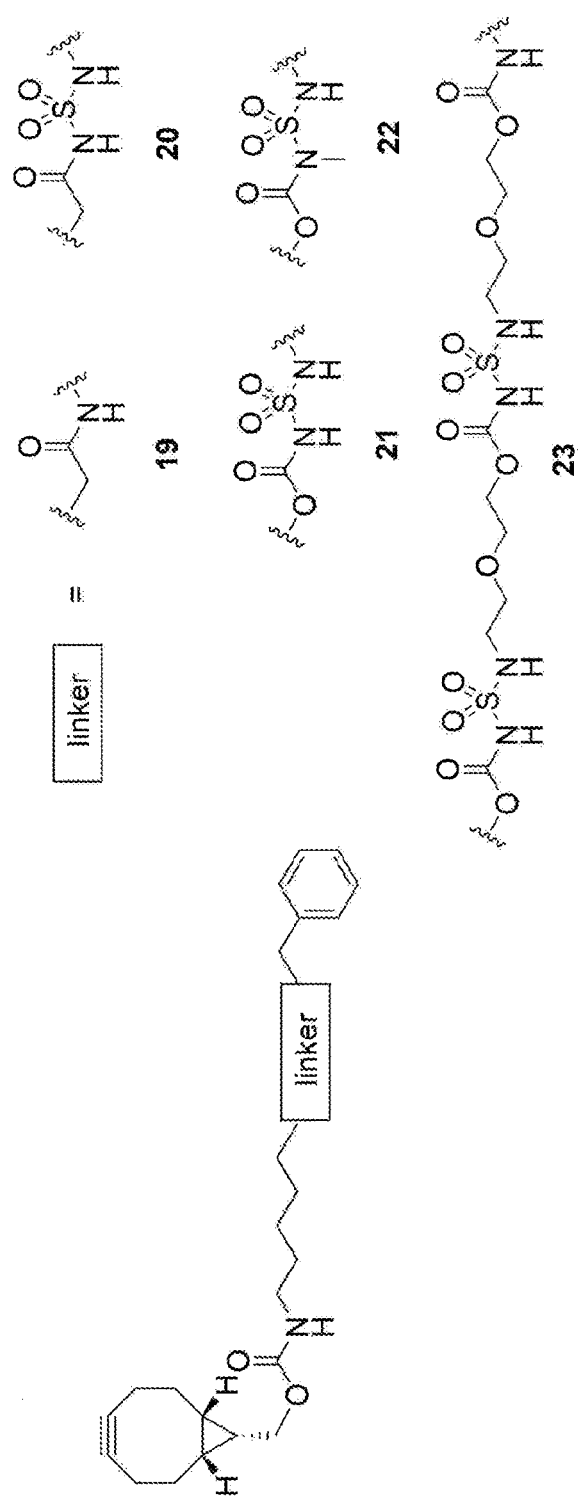
FIG. 6 shows the structures of several compounds wherein a bicyclo[6.1.0]non-4-yn-9-yl] reactive group $Q^1$ (also referred to as a BCN group) is connected to benzylamine (D) via a linker unit.
Figure 17:
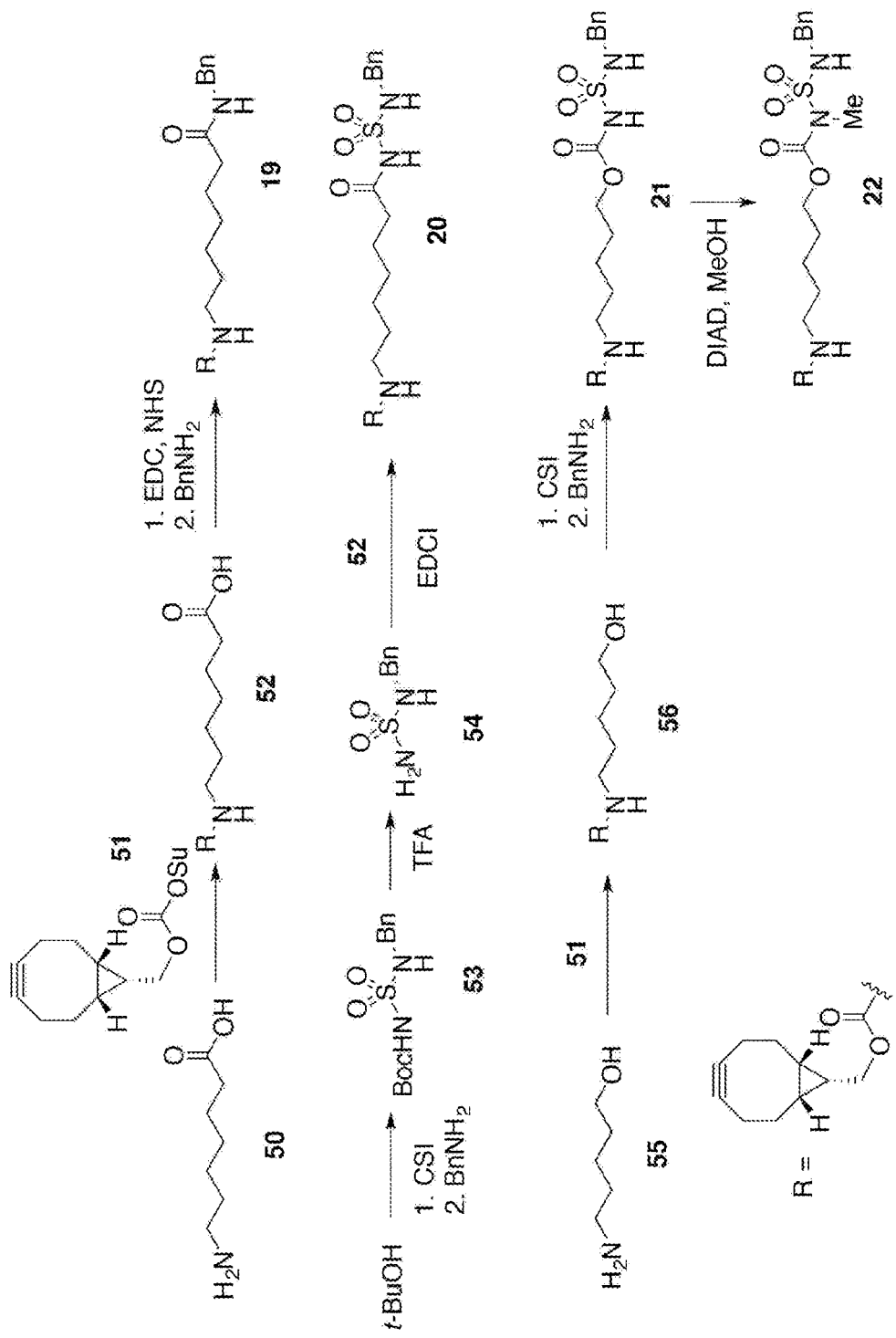
FIG. 17 shows the synthesis of several linker-conjugates, wherein $Q^1$ is a bicyclo[6.1.0]non-4-yn-9-yl] group (also referred to as a BCN group) and D is a benzyl group.
Figure 18:
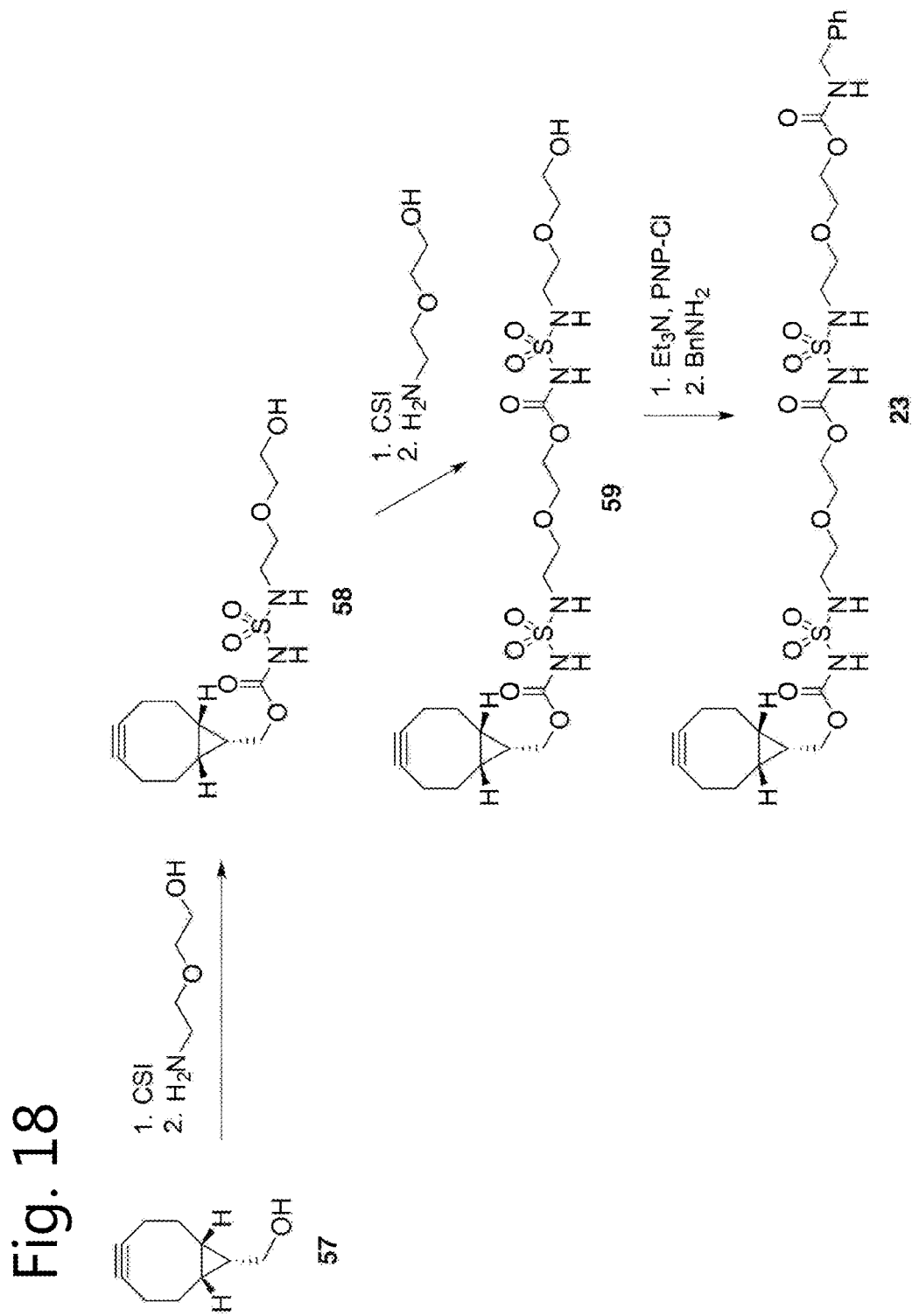
FIG. 18 shows the synthesis of a linker-conjugate bearing two sulfamide groups in the linker, wherein $Q^1$ is a bicyclo [6.1.0]non-4-yn-9-yl] group (also referred to as a BCN group) and D is a benzyl group.

FIG. 6 shows the structures of several compounds wherein a bicyclo[6.1.0]non-4-yn-9-yl] reactive group $Q^1$ (also referred to as a BCN group) is connected to benzylamine (D) via a linker unit. Compounds 20, 21 and 23 are according to the invention, whereas compounds 19 and 22 are comparative examples. FIG. 17 shows the synthesis of 19-22 (see also Examples 21-28) and FIG. 18 the synthesis of 23 (see also Examples 29-31).

Figure 7:
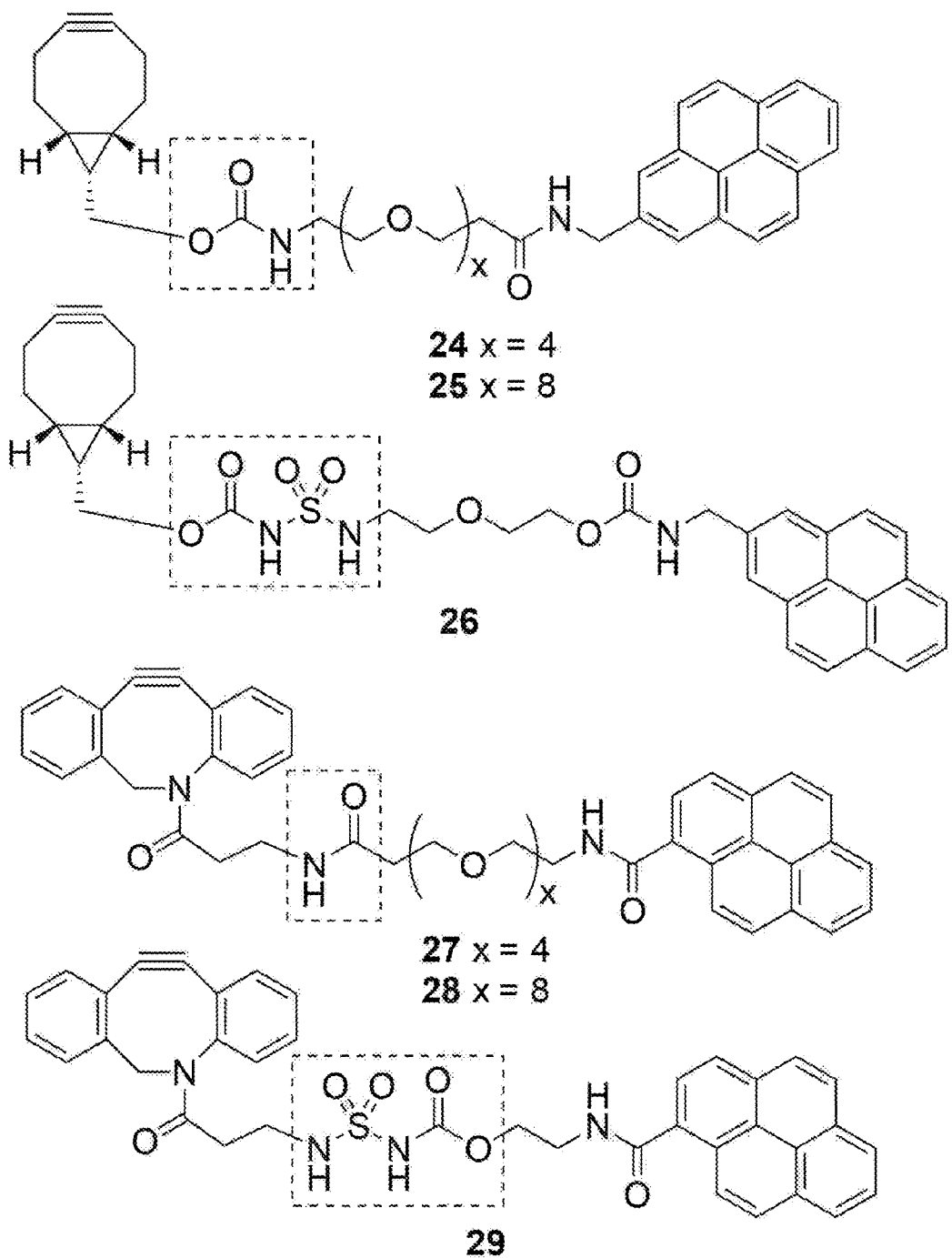
FIG. 7 shows the structures of several compounds wherein a bicyclo[6.1.0]non-4-yn-9-yl] reactive group $Q^1$ (also referred to as a BCN group) or a dibenzoazocyclooctyne reactive group $Q^1$ (also referred to as a DIBAC group or DBCO group) is connected to pyrene via a linker unit.
Figure 19:
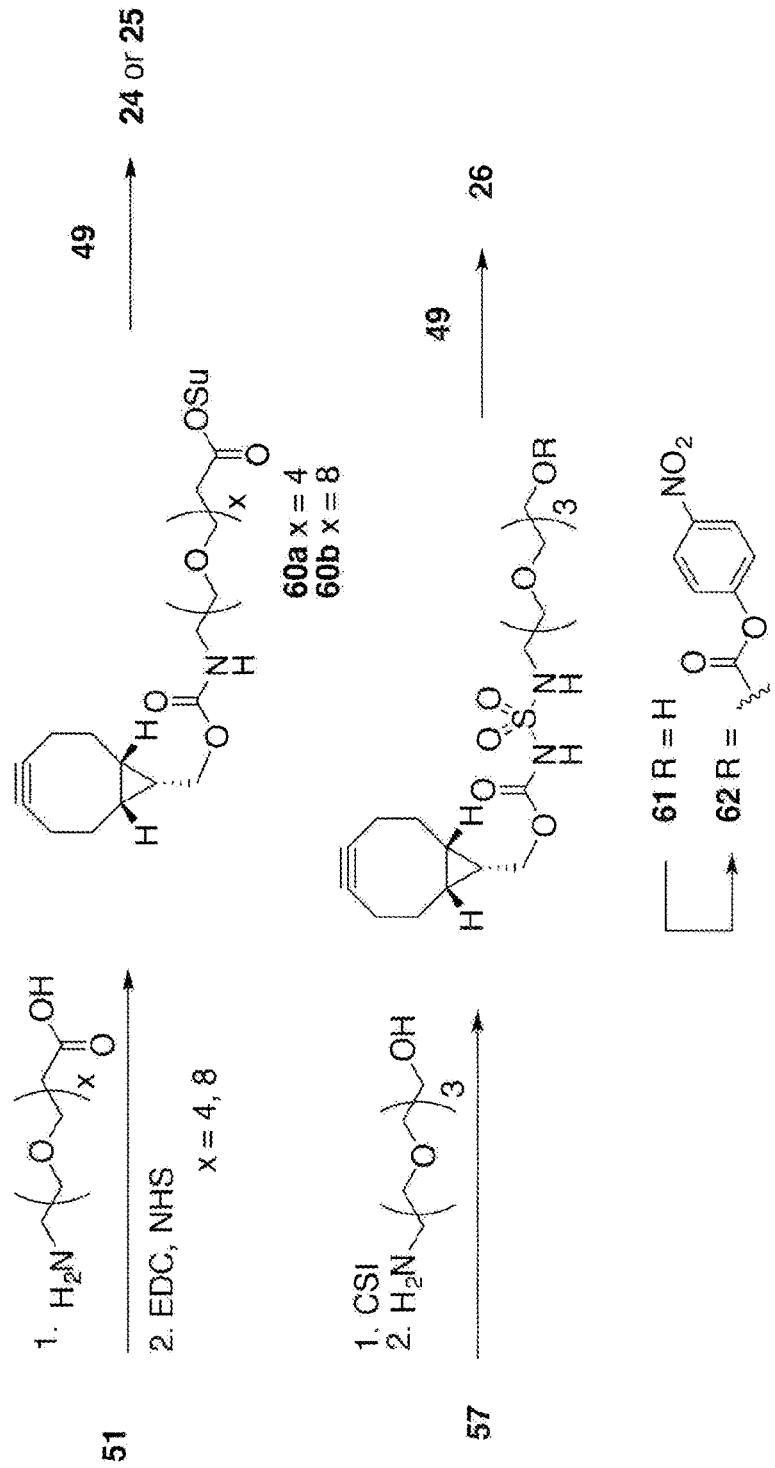
FIG. 19 shows the synthesis of several linker-conjugates, wherein $Q^1$ is a bicyclo[6.1.0]non-4-yn-9-yl] group (also referred to as a BCN group) and D is a pyrene group.
Figure 20:
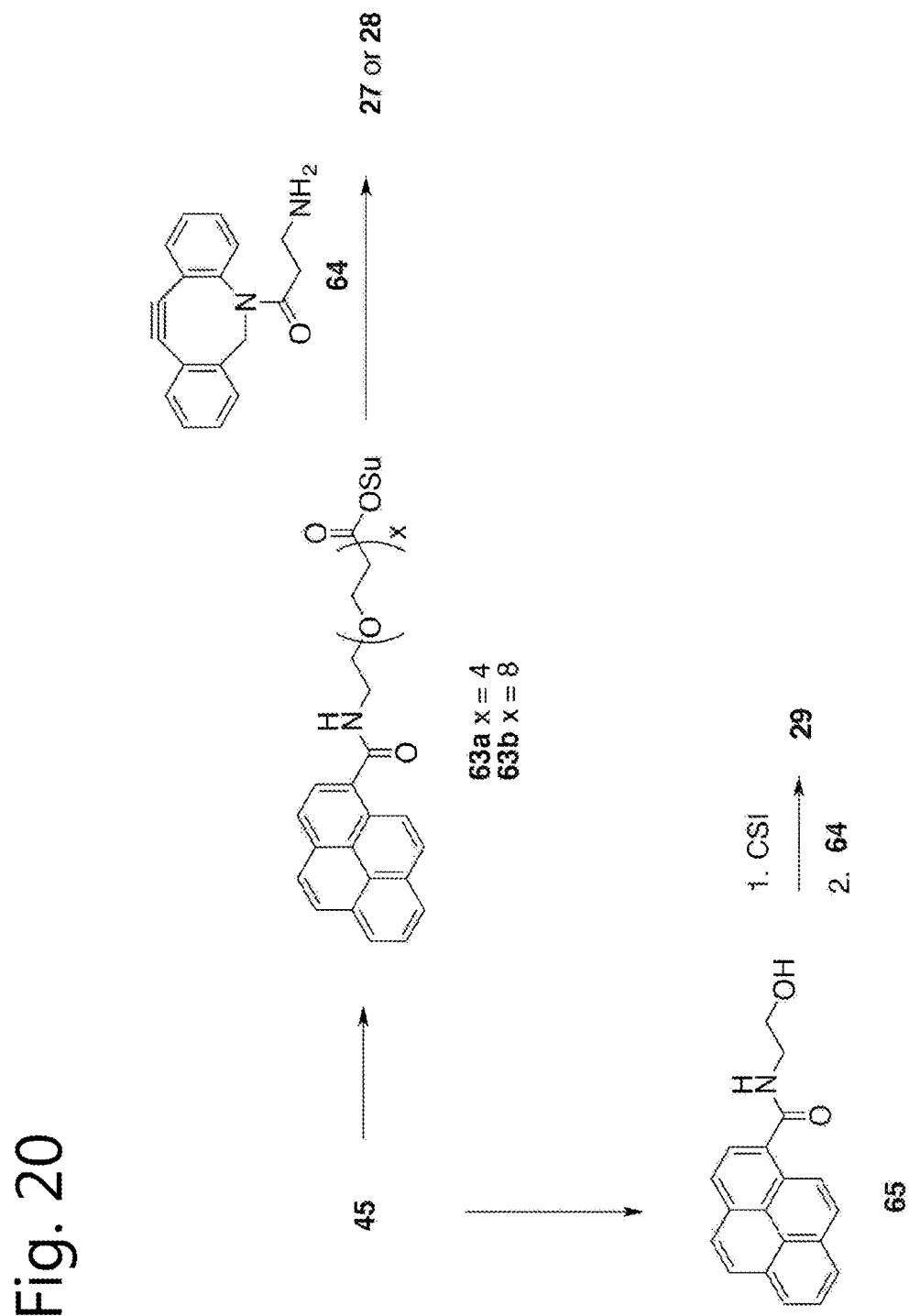
FIG. 20 shows the synthesis of several linker-conjugates wherein $Q^1$ is a heterocycloalkynyl group (DIBAC) and D is a pyrene group.

FIG. 7 shows the structures of several compounds wherein a bicyclo[6.1.0]non-4-yn-9-yl] reactive group $Q^1$ (also referred to as a BCN group) or a dibenzoazocyclooctyne reactive group $Q^1$ (also referred to as a DIBAC group or DBCO group) is connected to pyrene via a linker unit. Compounds 26 and 29 are according to the invention, whereas compounds 24, 25, 27 and 28 are comparative examples. FIG. 19 shows the synthetic routes leading to compounds 24-26, and FIG. 20 shows the synthetic routes leading to compounds 27-29.

Figure 8:
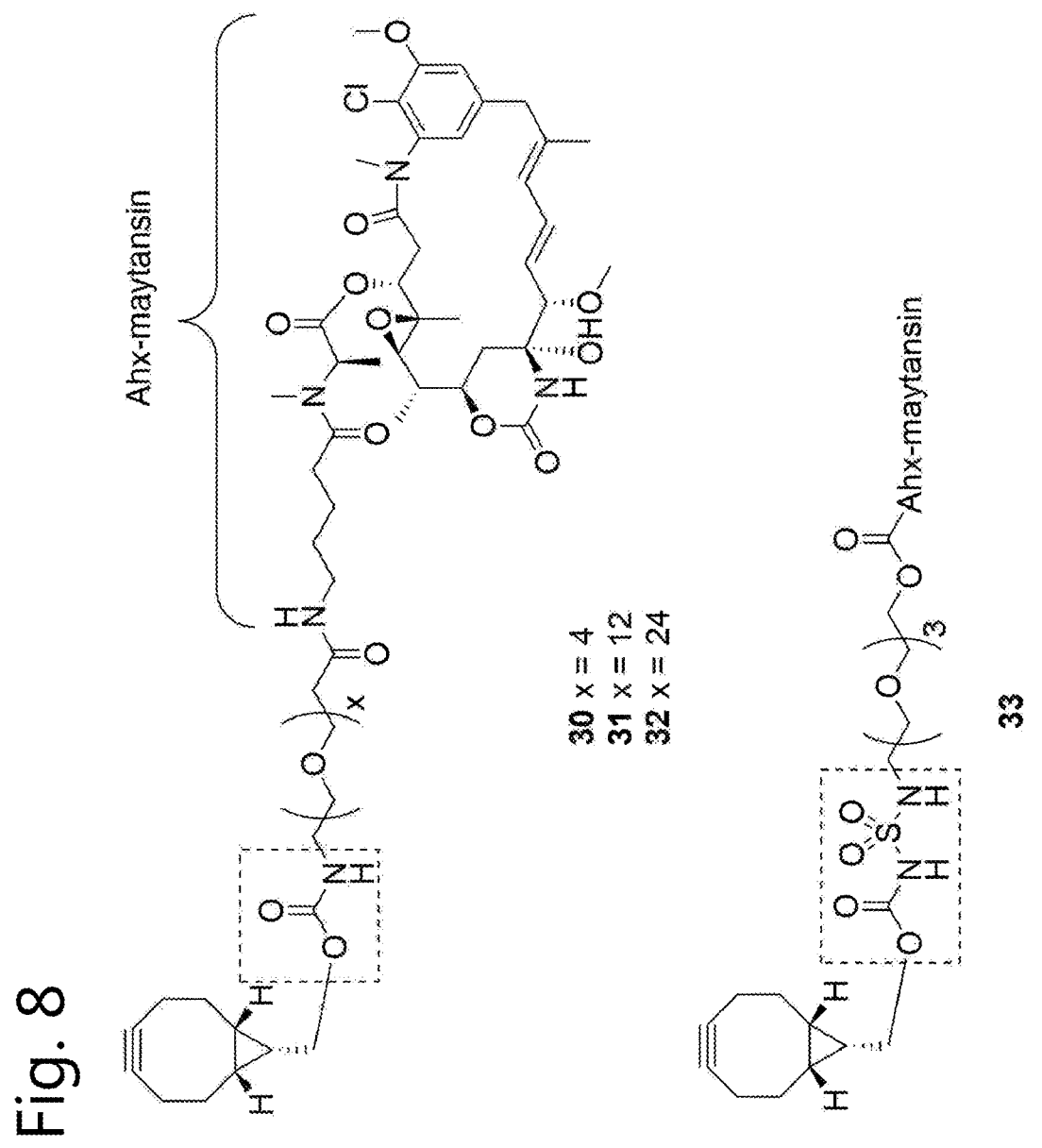

FIG. 8 shows the structures of several compounds wherein a bicyclo[6.1.0]non-4-yn-9-yl] reactive group $Q^1$ (also referred to as a BCN group) is connected to maytansin via a linker unit. Compound 33 is according to the invention, whereas compounds 30, 31 and 32 are comparative examples.

Figure 9:
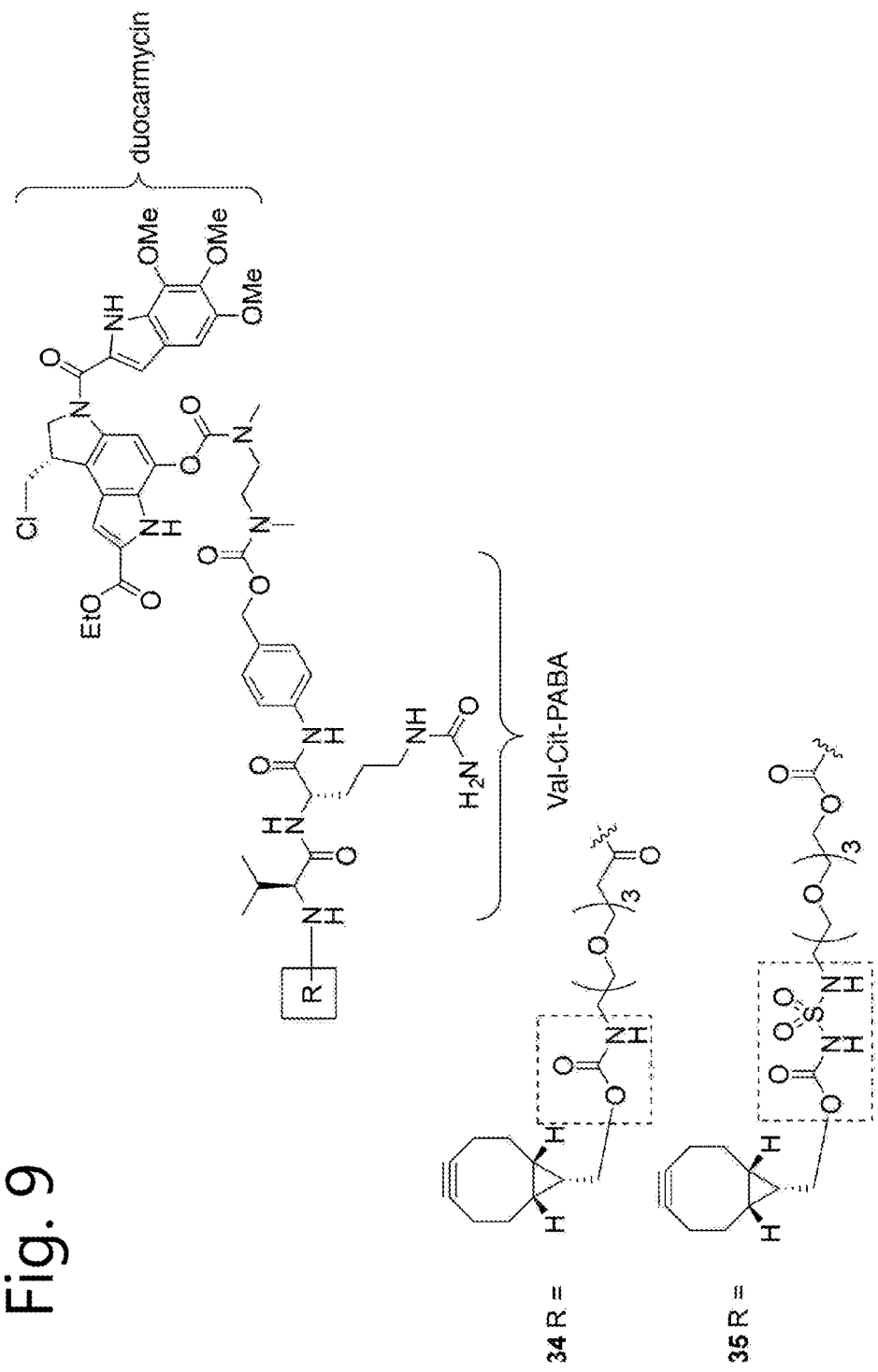
FIG. 9 shows the structures of several compounds wherein a bicyclo[6.1.0]non-4-yn-9-yl] reactive group $Q^1$ (also referred to as a BCN group) is connected to a Val-Cit-PABA-duocarmycin construct via a linker unit.

FIG. 9 shows the structures of several compounds wherein a bicyclo[6.1.0]non-4-yn-9-yl] reactive group $Q^1$ (also referred to as a BCN group) is connected to a Val-Cit-PABA-duocarmycin construct via a linker unit. Compound 35 is according to the invention, whereas compound 34 is a comparative example.

Figure 10:
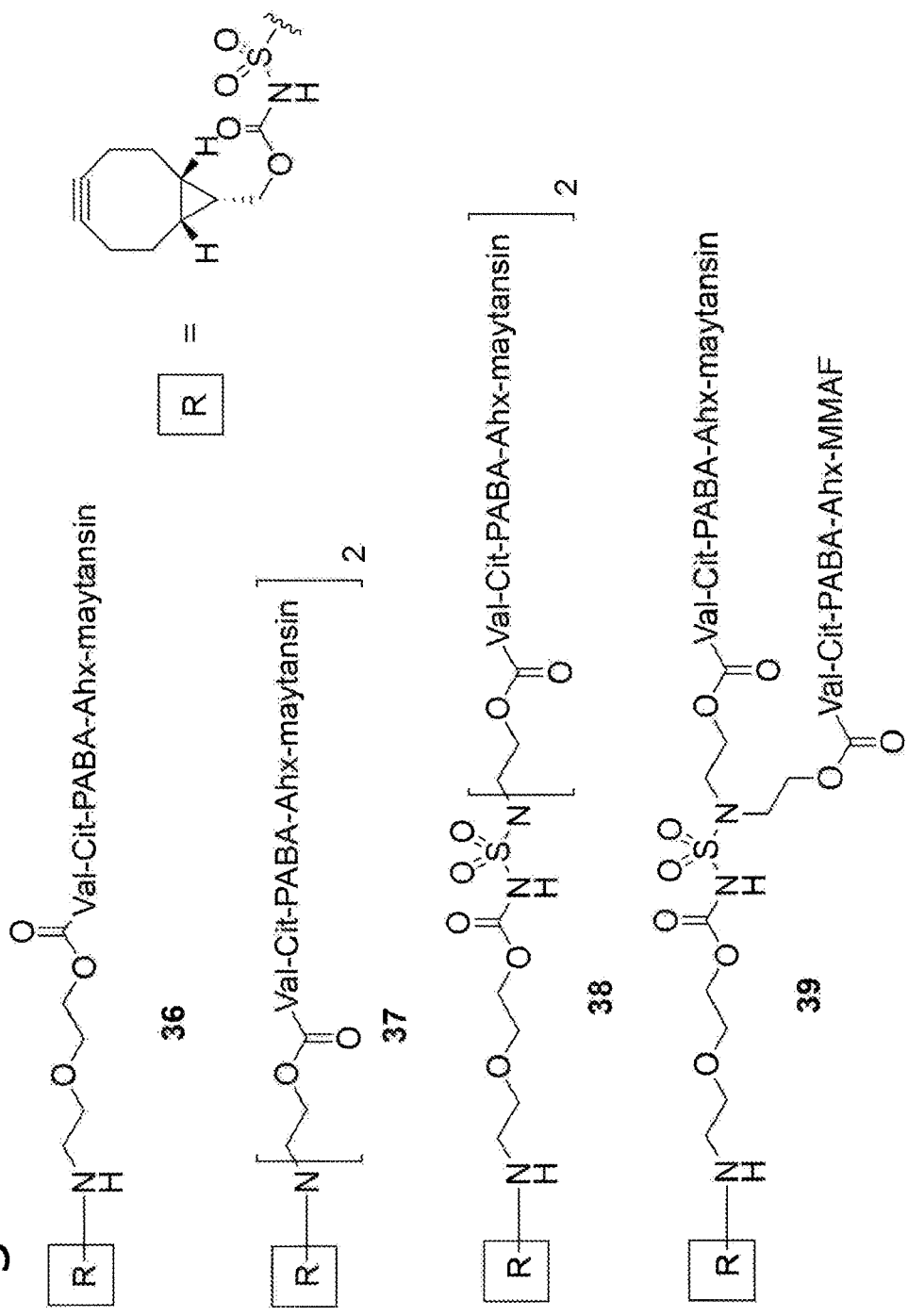
FIG. 10 shows the structures of several compounds according to the invention wherein a bicyclo[6.1.0]non-4-yn-9-yl] reactive group $Q^1$ (also referred to as a BCN group) is conjugated to Val-Cit-PABA-Ahx-maytansin via a linker unit.

FIG. 10 shows the structures of compounds 36-38 according to the invention wherein a bicyclo[6.1.0]non-4-yn-9-yl] reactive group $Q^1$ (also referred to as a BCN group) is conjugated to Val-Cit-PABA-Ahx-maytansin via a linker.

Figure 21:
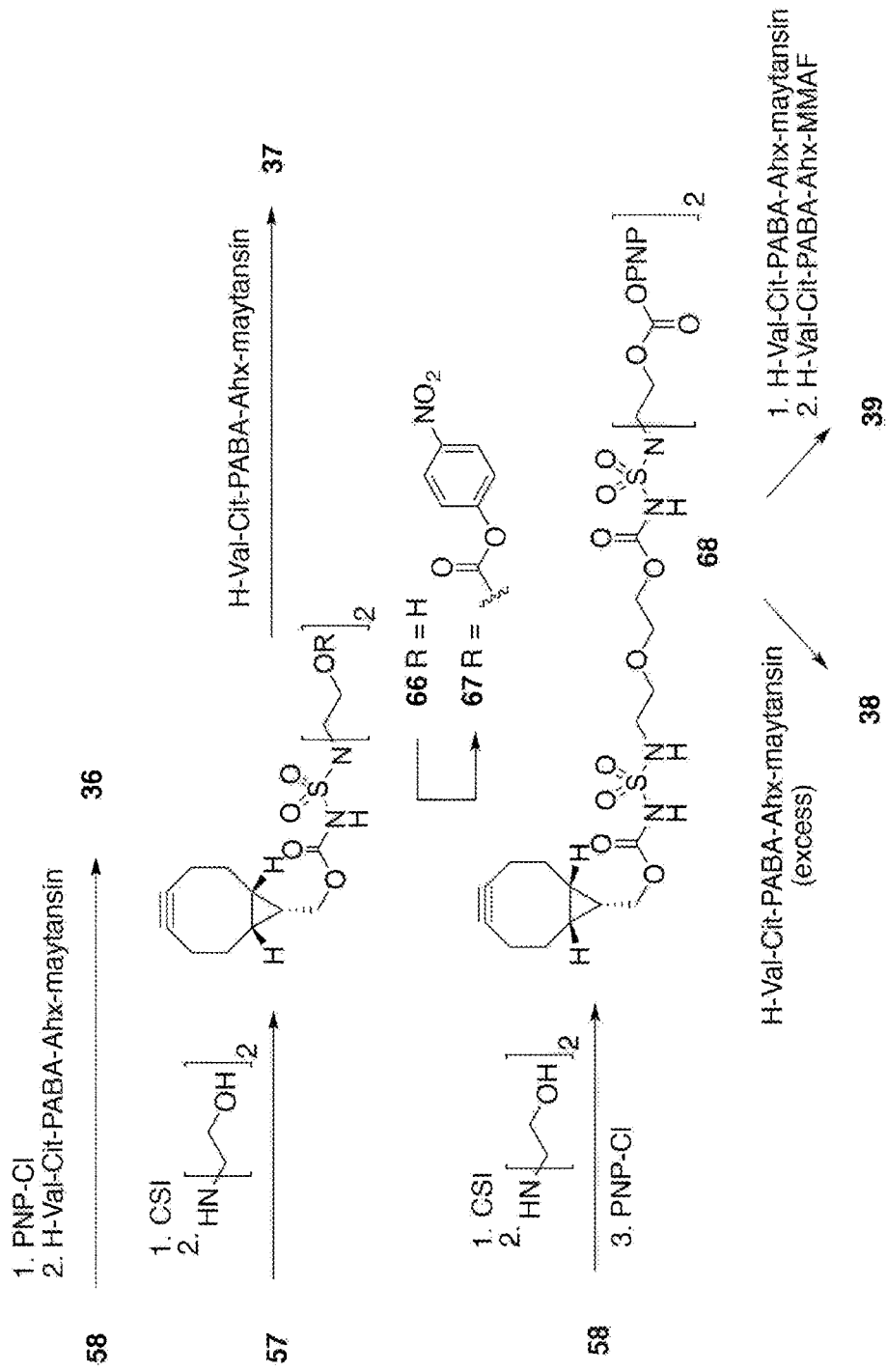
FIG. 21 shows the synthesis of a linker-conjugate comprising two target molecules D, wherein $Q^1$ is a bicyclo [6.1.0]non-4-yn-9-yl] group (also referred to as a BCN group) and D is a cytotoxin (maytansin).

The synthesis of compounds 30-35 is described in examples 43-49 and the synthetic routes for compounds 36-38 are graphically depicted in FIG. 21 and described in examples 50-55.

TABLE 3

Retention times of compounds 19-23 and 30-38 measured by RP-HPLC.

| compound | retention time (min) | |
|---|---|---|
| | 0.1% TFA | pH 7.4 |
| 19 (comp.) | 11.4 | 11.4 |
| 20 | 11.6 | 9.6 |
| 21 | 11.6 | 9.2 |
| 22 (comp.) | 12.7 | 12.6 |
| 23 | 10.6 | 6.9 |
| 30 (comp.) | 10.5 | 10.6 |
| 31 (comp.) | 10.1 | 10.1 |
| 32 (comp.) | 9.7 | 9.7 |
| 33 | 10.4 | 9.3 |
| 34 (comp.) | 11.5 | 11.5 |
| 35 | 11.6 | 10.0 |
| 36 | 10.4 | 9.3 |
| 37 | 11.2 | 10.5 |
| 38 | 11.1 | 9.5 |

As more polar compounds show reduced retention time, the lower values for compounds 20, 21 and 23 with respect to compound 19 and 22 at pH 7.4 (no effect is visible at low pH), clearly reflects the polarity of sulfamide spacers in comparison to normal amide-linker constructs (compound 19). Methylated compound 22, although also a sulfamide in the strict sense, does not display the enhanced polarity, due to the lack of an acidic proton at the acylated nitrogen. The fact that no clear difference in retention time is visible with 0.1% TFA (at which pH no deprotonation will take place) is also an indication that the acidic proton plays a key role in defining polarity. The bissulfamide compound 22 finally underlines that additional sulfamide units in a single linker (i.e. when f is 2 or more in the compounds and process according to the invention) further increases the polarity. The latter observation has also facilitated the smooth conjugation of a BCN-construct bearing two lipophilic toxins (maytansins), as in bissulfamide compound 38 and 39, to an azido-mAb.

The high polarity of the sulfamides also has a positive impact in case hydrophobic moieties are imparted onto a biomolecule of interest, which is known to require large amounts of organic cosolvent during conjugation and/or induce aggregation of the bioconjugate. High levels of cosolvent (up to 50% of DMA, propylene glycol, or DMSO) may induce protein denaturation during the conjugation process and/or may require special equipment in the manufacturing process. An example of the stability of the bioconjugate involves the highly polar bissulfamide-containing compound 38, which once conjugated to trastuzumab, displayed zero to negligible aggregation upon prolonged storage, which in fact also applied to monosulfamide 37.

In view of this reduced tendency to aggregate, the sulfamide linker according to the invention is particularly beneficial to be used to prepare bioconjugates wherein the reaction product of the conjugation reaction, i.e. reaction between reactive groups $Q^1$ and $F^1$, affords a linking moiety which is weakly water soluble. In an especially preferred embodiment, the conjugation is accomplished via a cycloaddition, preferably a 1,3-dipolar cycloaddition, more preferably alkyne-azide cycloaddition. As shown in the examples, any aggregation herein is beneficially reduced using the sulfamide linker according to the invention, which greatly improves the stability of the product by reducing the tendency to aggregate. Thus, the problem of aggregation associated with the hydrophobic linking moieties in bioconjugates is efficiently solved by using the sulfamide linker according to the invention in the spacer between the target molecule and the reactive group $Q^1$ in the linker-conjugate in the formation of the bioconjugate.

Figure 15:
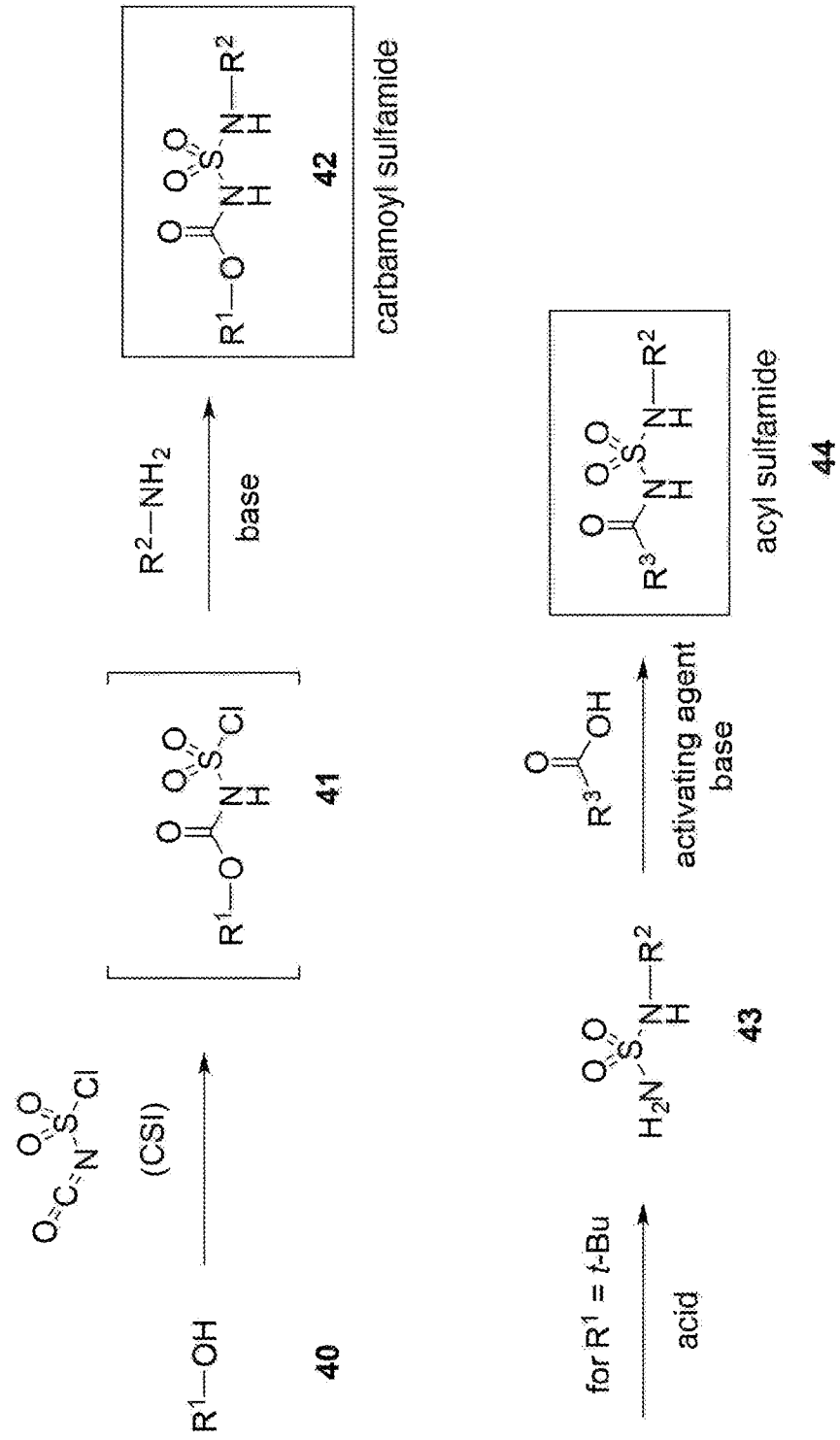
FIG. 15 shows the general synthetic scheme to convert an alcohol (40) into a carbamoyl sulfamide derivative (42) by consecutive treatment with chlorosulfonyl isocyanate (CSI) and an amine. The carbamoyl sulfamide 42 can be converted into an acylsulfamide (44) if the starting alcohol is tert-butanol, upon tert-butyl deprotection with acid to give sulfamide 43, which can be acylated to give 44.

An additional advantage of a sulfamide linker according the invention, and its use in bioconjugation processes, is its ease of synthesis and high yields. As schematically depicted in FIG. 15, synthesis of a carbamoyl sulfamide spacer involves the reaction of a primary alcohol 40 with the commercially available reagent CSI (chlorosulfonyl isocyanate), leading to an intermediate sulfonylchloride 41 that without work-up is reacted with an amine thereby affording the stable carbamoyl sulfamide 42. The latter compound can be easily converted into an acylsulfamide in case $R^1$ is a tert-butyl, which upon acid treatment affords a primary sulfamide product 43. Similarly, in case $R^1$=benzyl, deprotection can be affected with hydrogenation. The primary sulfamide 43 can be conveniently acylated with activated esters with common procedures to give acylsulfamide 44.

The ease of synthesis of sulfamide linkers according the invention, and their excellent performance in bioconjugation processes also becomes clear in the synthesis and utility of compounds 23 and 38, both bissulfamide constructs that are readily generated by repetition of the events summarized above, i.e. treatment of alcohol with CSI, followed by reaction with an aminoalcohol generates in return an alcohol that may again undergo the sequence of events, thereby generating a bissulfamide. Further repetition of the sequence generate tri-, tetra- and higher oligomers of sulfamide, depending on the number of repetitions.

The fact that the sulfamide linker in the final conjugate is short may have an additional advantage in the sense that it is known that in particular long PEG spacers (e.g. $PEG_{24}$), needed to counterbalance the hydrophobic character of a target molecules such as a cytotoxin, may have a negative impact on pharmacokinetics of the final protein conjugate, as is known for antibody-drug conjugates, in particular with high drug loading.

EXAMPLES

Example 1. Synthesis of α-2-azido-2-deoxy-3,4,6-tri-O-acetyl-D-galactose 1-phosphate α-2-Azido-2-deoxy-3,4,6-tri-O-acetyl-D-galactose 1-phosphate was prepared from D-galactosamine according to procedures described for D-glucosamine in Linhardt et al., *J. Org. Chem.* 2012, 77, 1449-1456, incorporated by reference.

$^1$H-NMR (300 MHz, CD$_3$OD): δ (ppm) 5.69 (dd, J=7.2, 3.3 Hz, 1H), 5.43-5.42 (m, 1H), 5.35 (dd, J=11.1, 3.3 Hz, 1H), 4.53 (t, J=7.2 Hz, 1H), 4.21-4.13 (m, 1H), 4.07-4.00 (m, 1H), 3.82 (dt, J=10.8, 2.7 Hz, 1H), 2.12 (s, 3H), 2.00 (s, 3H), 1.99 (s, 3H). LRMS (ESI−) m/z calcd for C$_{12}$H$_{17}$N$_3$O$_{11}$P (M−H$^+$)=410.06; found 410.00.

Example 2. Synthesis of α-UDP-2-azido-2-deoxy-3, 4, 6-tri-O-acetyl-D-galactose α-2-Azido-2-deoxy-3,4,6-tri-O-acetyl-D-galactose 1-phosphate, as prepared in example 1, was attached to UMP according to Baisch et al. *Bioorg. Med. Chem.*, 1997, 5, 383-391.

Thus, a solution of D-uridine-5'-monophosphate disodium salt (1.49 g, 4.05 mmol) in H$_2$O (15 mL) was treated with DOWEX 50W×8 (H$^+$ form) for 30 minutes and filtered. The filtrate was stirred vigorously at room temperature while tributylamine (0.97 mL, 4.05 mmol) was added dropwise. After 30 minutes of further stirring, the reaction mixture was lyophilized and further dried over P$_2$O$_5$ under vacuum for 5 h.

The resulting tributylammonium uridine-5'-monophosphate was dissolved in dry DMF (25 mL) in an argon atmosphere. Carbonyl diimidazole (1.38 g, 8.51 mmol) was added and the reaction mixture was stirred at r.t. for 30 min. Next, dry MeOH (180 μL) was added and stirred for 15 min to remove the excess carbonyldiimidazole. The leftover MeOH was removed under high vacuum for 15 min. The resulting compound (2.0 g, 4.86 mmol) was dissolved in dry DMF (25 mL) and added dropwise to the reaction mixture. The reaction was allowed to stir at rt for 2 d before concentration in vacuo.

The consumption of the imidazole-UMP intermediate was monitored by MS. Gradient flash column chromatography (7:2:1→5:2:1 EtOAc:MeOH:H$_2$O) afforded α-UDP-2-azido-2-deoxy-3,4,6-tri-O-acetyl-D-galactose (1.08 g, 1.51 mmol, 37%).

$^1$H-NMR (300 MHz, D$_2$O): δ (ppm) 7.96 (d, J=8.0 Hz, 1H), 5.98-5.94 (m, 2H), 5.81-5.79 (m, 1H), 5.70 (dd, J=7.1, 3.3 Hz, 1H), 5.49 (dd, J=15.2, 2.6 Hz, 1H), 5.30 (ddd, J=18.5, 11.0, 3.2 Hz, 2H), 4.57 (q, J=6.0 Hz, 2H), 4.35-4.16 (m, 9H), 4.07-3.95 (m, 2H), 2.17 (s, 3H), 2.08 (s, 3H), 2.07 (s, 3H). LRMS (ESI−) m/z calcd for C$_{21}$H$_{29}$N$_5$O$_{19}$P$_2$ (M−H$^+$)=716.09; found 716.3.

Example 3. Synthesis of α-UDP-2-azido-2-deoxy-D-galactose

Deacetylation of α-UDP-2-azido-2-deoxy-3,4,6-tri-O-acetyl-D-galactose, as prepared in example 2, was performed according to Kiso et al., *Glycoconj. J.*, 2006, 23, 565.

Thus, α-UDP-2-azido-2-deoxy-3,4,6-tri-O-acetyl-D-galactose (222 mg, 0.309 mmol) was dissolved in H$_2$O (2.5 mL) and Et$_3$N (2.5 mL) and MeOH (6 mL) were added. The reaction mixture was stirred for 3 h and then concentrated in vacuo to afford crude α-UDP-2-azido-2-deoxy-D-galactose.

$^1$H-NMR (300 MHz, D$_2$O): δ (ppm) 7.99 (d, J=8.2 Hz, 1H), 6.02-5.98 (m, 2H), 5.73 (dd, J=7.4, 3.4 Hz, 1H), 4.42-4.37 (m, 2H), 4.30-4.18 (m, 4H), 4.14-4.04 (m, 2H), 3.80-3.70 (m, 2H), 3.65-3.58 (m, 1H). LRMS (ESI−) m/z calcd for C$_{15}$H$_{23}$N$_5$O$_{16}$P$_2$(M−H$^+$)=590.05; found 590.20.

Example 4. Synthesis of α-UDP-D-galactosamine (UDP-GalNH$_2$)

To a solution of α-UDP-2-azido-2-deoxy-D-galactose, as prepared in example 3, in 1:1 H$_2$O-MeOH mixture (4 mL) was added Lindlar's catalyst (50 mg). The reaction was stirred under a hydrogen atmosphere for 5 h and filtered over celite. The filter was rinsed with H$_2$O (10 ml) and the filtrate was concentrated in vacuo to afford α-UDP-D-galactosamine (UDP-GalNH$_2$) (169 mg, 0.286 mmol, 92% yield over two steps). $^1$H-NMR (300 MHz, D$_2$O): δ (ppm) 7.93 (d, J=8.1 Hz, 1H), 5.99-5.90 (m, 2H), 5.76-5.69 (m, 1H), 4.39-4.34 (m, 2H), 4.31-4.17 (m, 5H), 4.05-4.01 (m, 1H), 3.94-3.86 (m, 1H), 3.82-3.70 (m, 3H), 3.30-3.16 (m, 1H). LRMS (ESI−) m/z calcd for C$_{15}$H$_{25}$N$_3$O$_{16}$P$_2$(M−H$^+$) =564.06; found 564.10.

Example 5. Synthesis of UDP-GalNProSAc

UDP-α-D-galactosamine (44 mg, 0.078 mmol) was dissolved in 0.1 M NaHCO$_3$ (1 mL). 3-AcS-propionic acid succinimidyl ester (38 mg, 0.156 mmol) and DMF (1 mL) were added and the reaction was stirred overnight at rt followed by concentration under reduced pressure. Gradient flash chromatography (7:2:1→5:2:1 EtOAc:MeOH:H$_2$O) afforded UDP-GalNProSAc (6 mg, 0.009 mmol, 11%)+ UDP-GalNAc contamination. LRMS (ESI−) calcd for C$_{20}$H$_{31}$N$_3$O$_{18}$P$_2$S (M−) 694.08 found 694.1.

$^1$H-NMR (300 MHz, D$_2$O): δ (ppm) 7.79 (m, 1H), 5.83-5.80 (m, 2H), 5.48-5.45 (m, 1H), 4.28-4.05 (m, 6H), 3.88-3.85 (m, 2H), 3.63-3.55 (m, 3H), 3.17-3.16 (m, 2H), 2.60-2.55 (m, 2H) 2.50 (s, 3H).

Example 6. Synthesis of UDP-GalNProSH (11a)

UDP-GalNProSAc (3 mg, 0.005 mmol) was dissolved in degassed 1M NaOH (1 mL) and stirred for 1.5 h followed by concentration in vacuo. The product was used crude in the glycosylation experiments.

$^1$H-NMR (400 MHz, D$_2$O): δ (ppm) 7.86 (d, J=8.0 Hz, 1H), 5.88-5.86 (m, 2H), 5.48-5.45 (m, 1H), 4.20-4.05 (m, 8H), 3.95-3.85 (m, 1H), 3.68-3.65 (m, 2H), 2.69-2.67 (m, 2H), 2.60-2.55 (m, 2H).

Example 7. Synthesis of ethyl 2-azido-2,2-difluoroacetate

To a solution of ethyl 2-bromo-2,2-difluoroacetate (950 mg, 4.68 mmol) in dry DMSO (5 mL) was added sodium azide (365 mg, 5.62 mmol). After stirring overnight at room temperature, the reaction mixture was poured into water (150 mL). The layers were separated, dichloromethane was added to the organic layer and the layer was dried over Na$_2$SO$_4$. After filtration, the solvent was removed under reduced pressure (300 mbar) at 35° C. affording crude ethyl 2-azido-2,2-difluoroacetate (250 mg, 1.51 mmol, 32%).

$^1$H-NMR (300 MHz, CDCl$_3$): δ (ppm) 4.41 (q, J=7.2 hz, 2H), 1.38 (t, J=6.9 Hz, 3H).

Example 8. Synthesis of α-2-amino-3,4,6-tri-O-acetyl-D-galactose 1-phosphate To a solution of α-2-azido-2-deoxy-3,4,6-tri-O-acetyl-D-galactose-1-phosphate (105 mg, 0.255 mmol), as prepared in example 1, in MeOH (3 mL) was added Pd/C (20 mg). The reaction was stirred under a hydrogen atmosphere for 2 h and filtered over celite. The filter was rinsed with MeOH (10 mL) and the filtrate was concentrated in vacuo to afford the free amine (94 mg, 0.244 mmol, 96%).

$^1$H-NMR (300 MHz, D$_2$O): δ (ppm) 5.87-5.76 (m, 1H), 5.44 (br. s, 1H), 5.30-5.20 (m, 1H), 4.55 (t, J=6.3 Hz, 1H), 4.28-4.00 (m, 3H), 2.11 (s, 3H), 2.03 (s, 3H), 2.00 (s, 3H). LRMS (ESI-) m/z calcd for C$_{12}$H$_{19}$NO$_{11}$P (M-H$^+$)=384.07; found 384.10.

Example 9. Synthesis of α-(2'-azido-2',2'-difluoro-acetamido)-3,4, 6-tri-O-acetyl-D-galactose 1-phosphate To a solution of α-2-amino-3,4,6-tri-O-acetyl-D-galactose 1-phosphate (94 mg, 0.244 mmol), as prepared in example 8, in dry DMF (3 mL), were added ethyl 2-azido-2,2-difluoroacetate (48 mg, 0.293 mmol) and Et$_3$N (68 μL, 0.488 mmol). The reaction was stirred for 6 h, followed by concentration in vacuo to afford the crude product. Gradient flash column chromatography (100:0→50:50 EtOAc:MeOH) afforded α-(2'-azido-2',2'-difluoroacetamido)-3,4,6-tri-O-acetyl-D-galactose 1-phosphate (63 mg, 0.125 mmol, 51%).

Example 10. Synthesis of UDP-α-(2'-azido-2',2'-difluoroacetamido)-3,4, 6-tri-O-acetyl-D-galactose α-(2'-Azido-2',2'-difluoroacetamido)-3,4,6-tri-O-acetyl-D-galactose 1-phosphate, as prepared in example 9, was coupled to UMP according to Baisch et al. *Bioorg. Med. Chem.*, 1997, 5, 383-391, incorporated by reference).

Thus, a solution of D-uridine-5'-monophosphate disodium salt (98 mg, 0.266 mmol) in H$_2$O (1 mL) was treated with DOWEX 50W×8 (H$^+$ form) for 40 minutes and filtered.

The filtrate was stirred vigorously at rt while tributylamine (63 μL, 0.266 mmol) was added dropwise. After 30 minutes of further stirring, the reaction mixture was lyophilized and further dried over P$_2$O$_5$ under vacuum for 5 h. The resulting tributylammonium uridine-5'-monophosphate was dissolved in dry DMF (15 mL) under an argon atmosphere. Carbonyl diimidazole (35 mg, 0.219 mmol) was added and the reaction mixture was stirred at rt for 30 min. Next, dry MeOH (4.63 μL) was added and stirred for 15 min to remove the excess carbonyl diimidazole. The remaining MeOH was removed under high vacuum (15 min.). Subsequently, N-methylimidazole.HCl (61 mg, 0.52 mmol) was added to the reaction mixture and the resulting compound (63 mg, 0.125 mmol) was dissolved in dry DMF (15 mL) and added dropwise to the reaction mixture. The reaction was stirred overnight at rt before concentrating the mixture under reduced pressure. The consumption of the imidazole-UMP intermediate was monitored by MS analysis. Gradient flash column chromatography (7:2:1→5:2:1 EtOAc:MeOH:H$_2$O) afforded UDP-α-(2'-azido-2',2'-difluoroacetamido)-3,4,6-tri-O-acetyl-D-galactose.

$^1$H-NMR (300 MHz, D$_2$O): δ (ppm) 7.87 (d, J=8.1 Hz, 1H), 5.913-5.85 (m, 2H), 5.67 (dd, J=6.6, 2.7 Hz, 1H), 5.56-5.50 (m, 1H), 5.47-5.43 (m, 1H), 5.31-5.25 (m, 2H), 4.61-4.43 (m, 2H), 4.31-4.05 (m, 5H), 2.16 (s, 3H), 2.02 (s, 3H), 1.94 (s, 3H). LRMS (ESI-) m/z calcd for C$_{23}$H$_{29}$F$_2$N$_6$O$_{20}$P$_2$(M-H$^+$)=809.09; found 809.1.

Example 11. Synthesis of α-UDP-2-(2'-azido-2',2'-difluoroacetamido)-2-deoxy-D-galactose (UDP-F2-GalNAz, 11c)

Deacetylation of UDP-α-(2'-azido-2',2'-difluoroacetamido)-3,4,6-tri-O-acetyl-D-galactose was performed according to Kiso et al., *Glycoconj. J.*, 2006, 23, 565, incorporated by reference.

Thus, UDP-α-(2'-azido-2',2'-difluoroacetamido)-3,4,6-tri-O-acetyl-D-galactose, as prepared in example 10, was dissolved in H$_2$O (1 mL) and triethylamine (1 mL) and MeOH (2.4 mL) were added. The reaction mixture was stirred for 2 h and then concentrated in vacuo. Gradient flash column chromatography (7:2:1→5:2:1 EtOAc:MeOH:H$_2$O) afforded α-UDP-2-(2'-azido-2',2'-difluoroacetamido)-2-deoxy-D-galactose (11c).

$^1$H-NMR (300 MHz, D$_2$O): δ (ppm) 7.86 (d, J=8.1 Hz, 1H), 5.91-5.85 (m, 2H), 5.54 (dd, J=6.6, 3.6 Hz, 1H), 4.31-3.95 (m, 9H), 3.74-3.62 (m, 2H). LRMS (ESI-) m/z calcd for C$_{17}$H$_{23}$F$_2$N$_6$O$_{17}$P$_2$(M-H$^+$)=683.06; found 683.10.

Trimming of Trastuzumab with endoS to Prepare 12

Mass Spectral Analysis of Monoclonal Antibodies

A solution of 50 μg (modified) IgG, 1 M Tris-HCl pH 8.0, 1 mM EDTA and 30 mM DTT in a total volume of approximately 70 μL was incubated for 20 minutes at 37° C. to reduce the disulfide bridges allowing to analyze both light and heavy chain. If present, azide-functionalities are also reduced to amines under these conditions. Reduced samples were washed three times with milliQ using an Amicon Ultra-0.5, Ultracel-10 Membrane (Millipore) and concentrated to 10 μM (modified) IgG. The reduced IgG was analyzed by electrospray ionization time-of-flight (ESI-TOF) on a JEOL AccuTOF. Deconvoluted spectra were obtained using Magtran software.

Example 12. Preparation of Trimmed Trastuzumab 12

Glycan trimming of trastuzumab was performed with endoS from *Streptococcus pyogenes* (commercially available from Genovis, Lund, Sweden). Thus, trastuzumab (10 mg/mL) was incubated with endoS (40 U/mL) in 25 mM Tris pH 8.0 for approximately 16 hours at 37° C. The deglycosylated IgG was concentrated and washed with 10 mM MnCl$_2$ and 25 mM Tris-HCl pH 8.0 using an Amicon Ultra-0.5, Ultracel-10 Membrane (Millipore).

A sample was subjected to MS analysis and after deconvolution of peaks, the mass spectrum showed one peak of the light chain and two peaks of the heavy chain. The two peaks of heavy chain belonged to one major product (49496 Da, 90% of total heavy chain), resulting from core GlcNAc (Fuc) substituted trastuzumab, and a minor product (49351 Da, +10% of total heavy chain), resulting from deglycosylated trastuzumab.

Transient Expression of a Trastuzumab Mutant and Glycosyltransferase Enzymes in CHO Proteins (enzymes and trastuzumab mutant) were transiently expressed in CHO K1 cells by Evitria (Zurich, Switzerland) at 20-25 mL scale.

```
GalT double mutant (Y289L, C342T) identified by
SEQ ID NO: 1
RDLRRLPQLVGVHPPLQGSSHGAAAIGQPSGELRLRGVAPPPPLQNSSKP

RSRAPSNLDAYSHPGPGPGPGSNLTSAPVPSTTTRSLTACPEESPLLVGP

MLIEFNIPVDLKLVEQQNPKVKLGGRYTPMDCISPHKVAIIIPFRNRQEH

LKYWLYYLHPILQRQQLDYGIYVINQAGESMFNRAKLLNVGFKEALKDYD

YNCFVFSDVDLIPMNDHNTYRCFSQPRHISVAMDKFGFSLPYVQLFGGVS
```

-continued

ALSKQQFLSINGFPNNYWGWGGEDDDIYNRLAFRGMSVSRPNAVIGKTRM

IRHSRDKKNEPNPQRFDRIAHTKETMLSDGLNSLTYMVLEVQRYPLYTKI

TVDIGTPS

CeGalNAcT [30-383] identified by SEQ ID NO: 2
KIPSLYENLTIGSSTLIADVDAMEAVLGNTASTSDDLLDTWNSTFSPISE

VNQTSFMEDIRPILFPDNQTLQFCNQTPPHLVGPIRVFLDEPDFKTLEKT

YPDTHAGGHGMPKDCVARHRVAIIVPYRDREAHLRIMLHNLHSLLAKQQL

DYAIFIVEQVANQTFNRGKLMNVGYDVASRLYPWQCFIFHDVDLLPEDDR

NLYTCPIQPRHMSVAIDKFNYKLPYSAIFGGISALTKDHLKKINGFSNDF

WGWGGEDDDLATRTSMAGLKVSRYPTQIARYKMIKHSTEATNPVNKCRYK

IMGQTKRRWTRDGLSNLKYKLVNLELKPLYTRAVVDLLEKDCRRELRRDF

PTCF

CeGalNAcT(30-383)-His$_6$) identified by SEQ ID NO: 3
KIPSLYENLTIGSSTLIADVDAMEAVLGNTASTSDDLLDTWNSTFSPISE

VNQTSFMEDIRPILFPDNQTLQFCNQTPPHLVGPIRVFLDEPDFKTLEKT

YPDTHAGGHGMPKDCVARHRVAIIVPYRDREAHLRIMLHNLHSLLAKQQL

DYAIFIVEQVANQTFNRGKLMNVGYDVASRLYPWQCFIFHDVDLLPEDDR

NLYTCPIQPRHMSVAIDKFNYKLPYSAIFGGISALTKDHLKKINGFSNDF

WGWGGEDDDLATRTSMAGLKVSRYPTQIARYKMIKHSTEATNPVNKCRYK

IMGQTKRRWTRDGLSNLKYKLVNLELKPLYTRAVVDLLEKDCRRELRRDF

PTCFHHHHHH

Trastuzumab (heavy chain N300C), identified by SEQ ID NO: 4
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYQ

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

Trastuzumab (light chain), identified by SEQ ID NO: 5
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK

Example 13-1. Purification of CeGalNAcT

The purification protocol is based on cation exchange on a SP column (GE Healthcare) followed by size exclusion chromatography.

In a typical purification experiment, CHO-produced supernatant containing the expressed CeGalNAcT was dialyzed against 20 mM Tris buffer, pH 7.5. The supernatant (typically 25 mL) was filtered through a 0.45 μM-pore diameter filter and subsequently purified over a cation exchange column (SP column, 5 mL, GE Healthcare), which was equilibrated with 20 mM Tris buffer, pH 7.5 prior to use. Purification was performed on an AKTA Prime chromatography system equipped with an external fraction collector. Samples were loaded from system pump A. The non-bound proteins were eluted from the column by washing the column with 10 column volumes (CVs) of 20 mM Tris buffer, pH 7.5. Retained protein was eluted with elution buffer (20 mM Tris, 1 NaCl, pH 7.5; 10 mL). Collected fractions were analyzed by SDS-PAGE on polyacrylamide gels (12%), and fractions containing the target protein were combined and concentrated using spin filtration to a volume of 0.5 mL. Next the protein was purified on a preparative Superdex size exclusion column, on an AKTA purifier system (UNICORN v6.3). This purification step led to the identification and separation of a dimer, and a monomer fraction of target protein. Both fractions were analyzed by SDS-PAGE and stored at −80 OC prior to further use Example 13-2. Purification of CeGalNAcT-His$_6$ In a typical purification experiment, CHO supernatant was filtered through a 0.45 μM-pore diameter filter and applied to a Ni-NTA column (GE Healthcare, 5 mL), which was equilibrated with buffer A (20 mM Tris buffer, 20 mM imidazole, 500 mM NaCl, pH 7.5) prior to use. Before filtration, imidazole was added to the CHO supernatant to a final concentration of 20 mM in order to minimize unspecific binding to the column. The column was first washed with buffer A (50 mL). Retained protein was eluted with buffer B (20 mM Tris, 500 mM NaCl, 250 mM imidazole, pH 7.5, 10 mL). Fractions were analyzed by SDS-PAGE on polyacrylamide gels (12%), and the fractions that contained purified target protein were combined and the buffer was exchanged against 20 mM Tris (pH 7.5) by dialysis performed overnight at 4° C. The purified protein was stored at −80° C. prior to further use. Note: for the identification of the monomeric and dimeric CeGalNAcT-His$_6$ species an additional SEC purification was performed (as described above).

Transfer of 11a-c to 12 to Prepare 13a-c

Example 14. Preparation of Trastuzumab(GalNProSH)$_2$ 13a

Deglycosylated trastuzumab (10 mg/mL) was incubated with UDP-galactose derivative 11a (1.3 mM) and β(1,4)-Gal-T1(Y289L,C342T) (2 mg/mL) in 10 mM MnCl$_2$ and 50 mM Tris-HCl pH 6.0 for 16 hours at 30° C.

Next, the functionalized trastuzumab was incubated with protein A agarose (40 μL per mg IgG) for 1 hours at rt. The protein A agarose was washed three times with TBS (pH 6.0) and the IgG was eluted with 100 mM glycine-HCl pH 2.5. The eluted IgG was neutralized with 1 M Tris-HCl pH 7.0 and concentrated and washed with 50 mM Tris-HCl pH 6.0 using an Amicon Ultra-0.5, Ultracel-10 Membrane (Millipore) to a concentration of 15-20 mg/mL. Spectral analysis after digestion with Fabricator and subsequent wash with MiliQ using an Amicon Ultra-0.5, Ultracel-10 Membrane (Millipore) showed the formation of two products, the major product (24387 Da) with the introduced GalNProSH and the minor (25037 Da) with the introduced GalNProSH+UDP-GalNProSH as disulfide. The ratio between the products is about 60:40.

Glycosyltransfer of a UDP-Galactose Derivative with Gal-TI(Y289L,C342T), General Protocol Enzymatic introduction of a UDP-galactose derivative onto deglycosylated trastuzumab was effected with a the double mutant of bovine β(1,4)-galactosyltransferase [β(1,4)-Gal-T1(Y289L,C342T)]. The deglycosylated trastuzumab (10 mg/mL) was incubated with the appropriate UDP-galactose derivative (0.4 mM) and Gal-T double mutant (1 mg/mL) in 10 mM $MnCl_2$ and 25 mM Tris-HCl pH 8.0 for 16 hours at 30° C.

Next, the functionalized trastuzumab was incubated with protein A agarose (40 µL per mg IgG) for 2 hours at 4° C. The protein A agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 15-20 mg/mL.

Glycosyltransfer of UDP-GalNAc Derivatives with CeGalNAcT (General Protocol)

Enzymatic introduction of GalNAc derivatives onto IgG was effected with a CeGalNAc-transferase. The deglycosylated IgG (prepared as described above, 10 mg/mL) was incubated with a modified UDP-GalNAc derivative (e.g. an azido-modified sugar-UDP derivative) (0.4 mM) and CeGalNAc-T (1 mg/mL) in 10 mM $MnCl_2$ and 25 mM Tris-HCl pH 8.0 for 16 hours at 30° C. The functionalized IgG (e.g. azido-functionalized IgG) was incubated with protein A agarose (40 µL per mg IgG) for 2 hours at 4° C. The protein An agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 15-20 mg/mL.

Example 15. Preparation of Trastuzumab(GalNAz)$_2$ 13b with GalT Double Mutant

Trastuzumab was subjected to the glycosyltransfer protocol with UDP-N-azidoacetylgalactosamine (UDP-GalNAz) and Gal-T double mutant. After protein A affinity purification, mass analysis indicated the formation of a major product (49713 Da, 90% of total heavy chain), resulting from GalNAz transfer to core GlcNAc(Fuc) substituted trastuzumab, and a minor product (49566 Da, +10% of total heavy chain), resulting from GalNAz transfer to core GlcNAc substituted trastuzumab.

This is an example of an azido-modified glycoprotein according to formula (13b).

Example 16-1. Preparation of Trastuzumab(GalNAz)$_2$13b with CeGalNAc-T

Trimmed trastuzumab was subjected to the glycosyltransfer protocol with UDP-N-azidoacetylgalactosamine (UDP-GalNAz) and CeGalNAc-T. After protein A affinity purification, a small sample was reduced with DTT and subsequently subjected to MS analysis indicating the formation of a one major product of (49713 Da, 90% of total heavy chain), resulting from GalNAz transfer to core GlcNAc(Fuc) substituted trastuzumab, and a minor product (49566 Da, +10% of total heavy chain), resulting from GalNAz transfer to core GlcNAc substituted trastuzumab.

Example 16-2. Preparation of trastuzumab (F$_2$-GalNAz)$_2$13c with CeGalNAc-T

Trimmed trastuzumab was subjected to the glycosyltransfer protocol with UDP-N-azidodifluoroacetylgalactosamine (UDP-F$_2$-GalNAz, 13c) and CeGalNAcT or CeGalNAcT-His$_6$. After protein A affinity purification a small sample was reduced with DTT and subsequently subjected to MS analysis indicating the formation of one major heavy chain product (49865 Da, approximately 90% of total heavy chain), resulting from F$_2$-GalNAz transfer to core GlcNAc (Fuc)-substituted trastuzumab which has reacted with DTT during sample preparation.

This is an example of an azido-modified glycoprotein according to formula (13c).
Synthesis of 17-68

Example 17. Synthesis of 1-Pyrenecarboxylic Acid OSu Ester (45)

To a solution of 1-pyrenecarboxylic acid (65 mg, 0.24 mmol) in DCM/DMF (2 mL each) was added N-hydroxysuccinimide (34 mg, 0.29 mmol) and EDC.HCl (70 mg, 0.36 mmol). The reaction was stirred for 2 h and subsequent diluted with DCM (10 mL), washed with aqueous citric acid (10%, 5 mL) and saturated NaHCO$_3$ (3×5 mL), dried over Na$_2$SO$_4$, filtrated and concentrated in vacuo to give crude 45.

Example 18. Synthesis of (46)

Compound 45 (480 mg, 1.38 mmol) was dissolved in DCM (15 mL) and tert-butyl (2-(2-(2-aminoethoxy)ethoxy)ethyl)carbamate (348 mg, 1.4 mmol and Et$_3$N (286 µL, 2.1 mmol) were added. The reaction mixture was stirred overnight and quenched with water (15 mL), the organic layer was washed with water (1×15 mL) and saturated aqueous NaHCO$_3$ (2×15 mL), dried over Na$_2$SO$_4$, filtrated and concentrated in vacuo. Purification via gradient flash column chromatography (DCM→DCM:MeOH 95:5) yielded the product 46 (460 mg, 0.97 mmol, 70%).

Example 19. Synthesis of (17)

Boc-protected pyrene amine 46 (460 mg, 0.97 mmol) was dissolved in methanol (10 mL) and acetylchloride (140 µL, 1.9 mmol) was added and after 1 and 3 h additional acetyl chloride (2×140 µL, 1.9 mmol) was added. After stirring for 4 h the mixture was concentrated under reduced pressure. Next, the crude product (100 mg, 0.24 mmol) was dissolved in DCM (3 mL) and 2,5-dioxopyrrolidin-1-yl 4-(2,5-dioxo-2,5-dihydro-1H-pyrrol-1-yl)butanoate (50 mg, 0.17 mmol) and Et$_3$N (73 µL, 0.52 mmol) were added. After stirring overnight the solution was quenched with water (3 mL), washed with water (2×3 mL), dried over Na$_2$SO$_4$, filtrated and concentrated. Purification via gradient flash column chromatography (DCM→DCM:MeOH 95:5) yielded the product 17 (69 mg, 0.13 mmol, 75%). $^1$H NMR (400 MHz, CDCl$_3$) δ (ppm) 8.48 (d, 1H, J=9.2 Hz), 8.12 (d, 2H, J=7.6 Hz), 8.04-7.93 (m, 6H), 6.59 (bs, 1H), 6.38 (s, 2H), 5.99 (bs, 1H), 3.76-3.71 (m, 4H), 3.62-3.60 (m, 2H), 3.54-3.52 (m, 2H), 3.37 (t, J=5.2 Hz, 2H), 3.23-3.17 (m, 4H), 1.82 (t, J=6.8 Hz, 2H), 1.63 (q, J=7.2 Hz, 2H).

Example 20-1. Synthesis of Maleimide Alcohol Derivative (47)

To a cooled (0° C.) solution of 5-aminopentan-1-ol (100 mg, 0.97 µmol) in saturated aqueous NaHCO$_3$ (16 mL) was added N-methoxycarbonylmaleimide (150 mg, 0.64 mol). The mixture was stirred for 1.5 h and extracted with DCM (2×20 mL). The combined organic layers were dried (Na$_2$SO$_4$) and concentrated. The product 47 was obtained as a colorless oil (137 mg, 0.75 mmol, 75%). $^1$H NMR (400 MHz, CDCl$_3$) δ (ppm) 6.69 (s, 2H), 3.70-3.67 (m, 1H), 3.67-3.60 (m, 2H), 3.53 (t, J=7.1 Hz, 2H), 1.68-1.54 (m, 4H), 1.42-1.31 (m, 2H).

Example 20-2. Synthesis of Maleimide-Pyrene Derivative (18)

To a solution of alcohol 47 (7.7 mg, 42 µmol) in DCM (1 mL) was added chlorosulfonyl isocyanate (CSI, 3.9 µL, 5.9 mg, 42 µmol). After the solution was stirred for 15 min, Et$_3$N (18 µL, 13 mg, 126 µmol) and a solution of 1-pyrenemethylamine.HCl (49, 11 mg, 42 µmol) and Et$_3$N (18 µL, 13 mg, 126 µmol) were added. After 80 min, saturated aqueous NH$_4$Cl (20 mL) and DCM (20 mL) were added. After separation, the organic phase was dried (Na$_2$SO$_4$) and concentrated. After gradient flash column chromatography (DCM→2% MeOH in DCM), product 18 was obtained as a slightly yellow solid (7.4 mg, 14.2 µmol, 34%). $^1$H NMR (400 MHz, CDCl$_3$/CD$_3$OD) δ (ppm) 8.32-8.26 (m, 1H), 8.20-7.90 (m, 8H), 6.61 (s, 2H), 4.90 (s, 2H), 3.65 (t, J=6.5 Hz, 2H), 3.30 (t, J=7.2 Hz, 2H). 1.40-1.20 (m, 4H), 1.08-0.97 (m, 2H).

Example 21. Synthesis of BCN-Heptanoic Acid (52)

To a solution of BCN-OSu derivative 51 in MeCN (5 mL) were added 7-aminoheptanoic acid 50 (145 mg, 1.0 mmol) in 0.1 M aqueous NaHCO$_3$ (30 mL) and MeCN (25 mL). The mixture was stirred for 4 h and partially concentrated. Aqueous saturated NH$_4$Cl (30 mL) was added and after extraction with DCM (2×30 mL), the combined organics were dried (Na$_2$SO$_4$) and concentrated. Product 52 was used in the step without further purification. $^1$H NMR (400 MHz, CDCl$_3$) δ (ppm) 4.68 (bs, 1H), 4.14 (d, J=7.9 Hz, 2H), 3.17 (dd, J=12.8, 6.3 Hz, 2H), 2.35 (t, J=7.5 Hz, 2H), 2.32-2.09 (m, 6H), 1.70-1.25 (m, 11H), 0.94 (t, J=9.7 Hz, 2H).

Example 22. Synthesis of BCN-Heptanoic Acid Benzylamide (19)

To a mixture of 51 (291 mg, 1.00 mmol) in DCM (25 mL) were added 7-aminoheptanoic acid 50 and Et$_3$N (417 µl, 303 mg, 3.00 mmol) and DMF (10 mL) was added. After evaporation (40° C.) of DCM, the resulting mixture was stirred for 10 min and an aqueous solution (0.1 M) of NaHCO$_3$ was added. After the reaction mixture was stirred for an additional 3 h, it was poured out in saturated aqueous NH$_4$Cl (50 mL) and extracted with DCM (2×50 mL). The combined organic layers were dried (Na$_2$SO$_4$) and concentrated. The residue was taken up in DCM (25 mL), N-(3-dimethylaminopropyl)-N'-ethylcarbodiimide hydrochloride (EDCI.HCl, 249 mg, 1.30 mmol) and N-hydroxysuccinimide (150, 1.30 mmol) were added and the resulting mixture was stirred for 18 h. After addition of water (50 mL), the layers were separated and the aqueous phase was extracted with DCM (2×25 mL). The combined organic layers were washed with brine (50 mL), dried (Na$_2$SO$_4$) and concentrated. Column chromatography yielded the intermediate NHS ester derivative of 52 as a colorless thick oil (233 mg, 0.56 mmol, 56%). $^1$H NMR (400 MHz, CDCl$_3$) δ (ppm) 4.69 (s, 1H), 4.14 (d, J=8.0 Hz, 2H), 3.17 (dd, J=13.6, 6.9 Hz, 2H), 2.91-2.77 (m, 4H), 2.61 (t, J=7.4 Hz, 2H), 2.37-2.12 (m, 2H), 1.83-1.69 (m, 4H), 1.66-1.17 (m, 9H), 1.01-0.90 (m, 2H). Next, to a solution of the intermediate BCN-aminoheptanoic acid NHS ester (49 mg, 0.12 mmol) in DCM (12 mL) were added benzylamine (19 µL, 19 mg, 0.18 mmol) and Et$_3$N (50 µL, 36 mg, 0.36 mmol). The mixture was stirred for 19 h and DCM (10 mL) and saturated aqueous NH$_4$Cl (20 mL) were added. The organic layer was dried (Na$_2$SO$_4$) and concentrated. After gradient column chromatography (25%→50% EtOAc in heptane) compound 19 was obtained as a white solid (31 mg, 0.076 mmol, 63%). $^1$H NMR (400 MHz, CDCl$_3$) δ (ppm) 7.38-7.27 (m, 5H), 5.72 (bs, 1H), 4.64 (bs, 1H), 4.45 (d, J=5.6 Hz, 2H), 4.13 (d, J=8.1 Hz, 2H), 3.16 (dd, J=12.8, 6.3 Hz, 2H), 2.38-2.13 (m, 8H), 1.75-1.11 (m, 11H), 1.00-0.88 (m, 2H).

Example 23. Synthesis of Tert-Butyl N-Benzylsulfamoylcarbamate (53)

Under an atmosphere of N$_2$, to a cooled solution (−78° C.) of tert-butanol in Et$_2$O (20 mL) was added chlorosulfonyl isocyanate (CSI) and the mixture was allowed to reach rt. After 45 min, the mixture was concentrated and the resulting tert-butyl chlorosulfonylcarbamate was used in the next step without further purification (considered 68% pure). Thus, to a solution of the crude tert-butyl chlorosulfonylcarbamate (199 mg crude=135 mg, 0.63 mmol) in DCM (10 mL) was added Et$_3$N (263 µL, 191 mg, 1.89 mmol) and benzylamine (82 µL, 81 mg, 0.85 mmol). The mixture was stirred for 2 h and quenched with saturated aqueous NH$_4$Cl.

DCM (10 mL) was added and the layers were separated. The organic layer was dried (Na$_2$SO$_4$) and concentrated. After gradient column chromatography (25%→50% EtOAc in heptane) compound 53 was obtained as a white solid (169 mg, 0.59 mmol).
$^1$H NMR (400 MHz, CDCl$_3$) δ (ppm) 7.41-7.29 (m, 5H), 5.41-5.30 (m, 1H), 4.30-4.20 (m, 2H), 1.46 (s, 9H).

Example 24. Synthesis of N-Benzylsulfamide (54)

To a solution of tert-butyl N-benzylsulfamoylcarbamate 53 (108 mg, 0.38) in DCM (10 mL) was added trifluoroacetic acid (2 mL). The reaction mixture was stirred for 1.5 h and poured into saturated aqueous NaHCO$_3$ (50 mL). After addition of another 50 mL of saturated aqueous NaHCO$_3$, the aqueous mixture was extracted with DCM (50 mL). The organic layer was dried (Na$_2$SO$_4$) and concentrated. The product 54 was obtained as a white solid (36 mg, 0.19 mmol, 50%). $^1$H NMR (400 MHz, CDCl$_3$) δ (ppm) 7.41-7.30 (m, 5H), 4.32 (d, J=6.1 Hz, 2H).

Example 25. Synthesis of (20)

To a solution of 52 (44 mg, 0.136 mmol) in DCM (5 mL) were added EDCI.HCl (39 mg, 0.204 mmol), DMAP (2.9 mg, 0.024 mmol) and N-benzylsulfamide 54 (13 mg, 0.068 mmol). After the reaction mixture was allowed to stir for 22 h at rt, EtOAc (20 mL) and aqueous saturated NH$_4$Cl (20 mL) were added. After separation, the aqueous phase was extracted with EtOAc (20 mL). The combined organic phases were dried (Na$_2$SO$_4$) and concentrated. After gradient column chromatography (25%→50% EtOAc in heptane), the product 20 was obtained as an inseparable mixture of the title compound and N-benzylsulfamide 54 (3.2/1 mass ratio) (14.4 mg). $^1$H NMR (400 MHz, CDCl$_3$) δ (ppm) 7.38-7.27 (m, 5H), 5.99 (bs, 1H), 5.01 (t, J=6.2 Hz, 1H), 4.20 (s, 2H), 4.85-4.70 (m, 2H), 4.13 (d, J=8.12 Hz, 2H), 3.15 (q, J=6.50, 2H), 2.35-2.15 (m, 6H), 2.09 (t, J=7.4 Hz, 2H), 1.65-0.75 (m, 13H).

Example 26. Synthesis of (56)

To a solution of 51 (430 mg, 1.48 mmol) in DCM (20 mL) was added a solution of 5-aminopentan-1-ol 55 (152 mg, 1.47 mmol) in DCM (4 mL) and Et$_3$N (619 µL, 449 mg, 4.44 mmol). The mixture was stirred for 1.5 h at rt after which a saturated aqueous solution of NaHCO$_3$ was added (40 mL). After separation, the organic layer was dried (Na$_2$SO$_4$) and concentrated. The residue was purified by gradient column chromatography (EtOAc/heptane 1/1→3/1). The product 56 was obtained as a colorless sticky liquid (356 mg, 1.27 mmol, 81%). $^1$H NMR (400 MHz, CDCl$_3$) δ (ppm) 4.68 (s, 1H), 4.14 (d, J=8.0 Hz, 2H), 3.65 (dd, J=11.7, 6.3 Hz, 2H), 3.19 (dd, J=13.2, 6.7 Hz, 2H), 2.35-2.15 (m, 6H), 1.66-1.30 (m, 7H), 1.02-0.88 (m, 2H).

Example 27. Synthesis of (21)

To a solution of 56 (51 mg, 0.18 mmol) in DCM (10 mL) was added chlorosulfonyl isocyanate (16 µl, 25 mg, 0.18 mmol). After the mixture was stirred for 40 min, Et$_3$N (75 µl, 55 mg, 0.54 mmol) and benzylamine (19 µl, 19 mg, 0.18 mmol) were added.

The mixture was stirred for an additional 1.5 h and quenched through addition of an aqueous solution of NH$_4$Cl (sat). After separation, the aqueous layer was extracted with DCM (20 mL). The combined organic layers were dried (Na$_2$SO$_4$) and concentrated.

The residue was purified by gradient column chromatography (20%→50% EtOAc in pentane) and product 21 was obtained as colorless thick oil (57 mg, 0.12 mmol, 67%). $^1$H NMR (400 MHz, CDCl$_3$) δ (ppm) 7.41-7.28 (m, 5H), 5.55 (s, 1H), 4.75 (s, 1H), 4.29-4.24 (m, 2H), 4.20-4.08 (m, 2H), 3.19 (dd, J=13.4, 6.6 Hz, 2H), 2.37-2.16 (m, 6H), 1.74-1.31 (m, 9H), 0.94 (t, J=9.7 Hz, 2H).

Example 28. Synthesis of (22)

Under an inert atmosphere, 21 (93 mg, 0.19 mmol) was dissolved in anhydrous THF (10 mL). PPh$_3$ (49 mg, 0.19 mmol) and MeOH (50 µL, 1.23 mmol) were added and the mixture was cooled to 0° C. A solution of DIAD (37 µL, 0.19 mmol) in anhydrous THF (5 mL) was slowly added and the mixture was allowed to reach rt, after which the reaction was stirred for 18 h and subsequently concentrated. Gradient column chromatography (20→50% EtOAc in heptane) yielded product 22 as colorless thick oil. $^1$H NMR (400 MHz, CDCl$_3$) δ (ppm) 7.39-7.26 (m, 5H), 5.94-5.84 (m, 1H), 4.80-4.64 (m, 1H), 4.19 (d, J=6.4 Hz, 2H,), 4.13 (d, J=7.4 Hz, 2H), 4.08 (t, J=6.5 Hz, 2H), 3.17 (q, 2H, J=6.5 Hz), 3.12 (s, 3H), 2.35-2.14 (m, 6H), 1.80-1.65 (m, 13H).

Example 29. Synthesis of (58)

To a solution of 57 (1.5 g, 10 mmol) in DCM (150 mL), under a N$_2$ atmosphere, was added CSI (0.87 mL, 1.4 g, 10 mmol), Et$_3$N (2.8 mL, 2.0 g, 20 mmol) and 2-(2-aminoethoxy)ethanol (1.2 mL, 1.26 g, 12 mmol). The mixture was stirred for 10 min and quenched through addition of aqueous NH$_4$Cl (sat., 150 mL). After separation, the aqueous layers was extracted with DCM (150 mL). The combined organic layers were dried (Na$_2$SO$_4$) and concentrated. The residue was purified with column chromatography. Product 58 was obtained as slightly yellow thick oil (2.06 g, 5.72 mmol, 57%). $^1$H NMR (400 MHz, CDCl$_3$) δ (ppm) 6.0 (bs, 1H), 4.28 (d, J=8.2 Hz, 2H), 3.78-3.73 (m, 2H), 3.66-3.61 (m, 2H), 3.61-3.55 (m, 2H), 3.34 (t, J=4.9 Hz, 2H), 2.37-2.15 (m, 6H), 1.64-1.48 (m, 2H), 1.40 (quintet, J=8.7 Hz, 1H), 1.05-0.92 (m, 2H).

Example 30. Synthesis of (59)

To a solution of 58 (130 mg, 0.36 mmol) were subsequently added CSI (31 µL, 51 mg, 0.36 mmol), Et$_3$N (151 µL) and 2-(2-aminoethoxy)ethanol (36 µL, 38 mg, 0.36 mmol). After 15 min, water (20 mL) was added and after separation, the aqueous layer was acidified with 1 M aq. HCl to pH 3 and extracted with DCM (20 mL). The DCM layer was dried and concentrated. After column chromatography, the product 59 was obtained as colorless oil (87 mg, 0.15 mmol, 42%). $^1$H NMR (400 MHz, CDCl$_3$) δ (ppm) 6.15-5.95 (m, 2H), 4.40-4.32 (m, 2H), 4.31 (d, J=8.3 Hz, 2H), 3.85-3.55 (m, 10H), 3.45-3.25 (m, 4H), 2.40-2.15 (m, 6H), 1.65-1.47 (m, 2H), 1.40 (quintet, J=8.7 Hz, 1H), 1.06-1.92 (m, 2H).

Example 31. Synthesis of (23)

To a solution of 59 (63 mg, 0.11 mmol) in DCM (10 mL) were subsequently added p-nitrophenyl chloroformate (22 mg, 0.11 mmol) and Et$_3$N (46 µL, 33 mg, 0.33 mmol). After 20 h, benzylamine (22 µL, 21.6 mg, 0.20 mmol) was added to the reaction mixture. The mixture was stirred for an additional 24 h where after the mixture was concentrated and the residue was purified by gradient column chromatography (1st col. 0→20% MeOH in DCM, 2nd col. 0→8% MeOH in DCM). Product 23 was obtained as a colorless film (18 mg, 0.026 mmol, 23%). $^1$H NMR (400 MHz, CD$_3$OD) δ (ppm) 7.38-7.18 (m, 5H), 4.31-4.22 (m, 6H), 4.22-4.16 (m, 2H), 3.70-3.63 (m, 4H), 3.63-3.54 (m, 4H), 3.34 (s, 1H), 3.24-3.15 (m, 4H), 2.30-2.10 (m, 6H), 1.68-1.52 (m, 2H), 1.42 (quintet, J=8.7 Hz, 1H), 1.02-0.90 (m, 2H).

Example 32. Synthesis of BCN-dPEG$_4$-C(O)OSu (60a)

To a solution of amino-dPEG$_4$-acid (1.23 g, 4.23 mmol) in anhydrous DMF (30 mL) were subsequently added 51 (1.02 g, 3.85 mmol) and triethylamine (1.60 mL, 11.53 mmol). The reaction mixture was stirred for 3 h at rt, after which EDCI.HCl (0.884 g, 4.61 mmol) and NHS (88 mg, 0.77 mmol) were added. The resulting solution was stirred overnight at rt and poured into 100 mL NaHCO$_3$ (sat.) and 150 mL EtOAc. The layers were separated and the organic phase was washed with sat. NaHCO$_3$ (90 mL) and H$_2$O (75 mL). The organic phase was dried (Na$_2$SO$_4$), filtered and concentrated in vacuo. Gradient flash chromatography (MeCN→MeCN:H$_2$O 30:1) afforded product 60a as colorless oil (800 mg, 1.48 mmol, 40%).

Example 33. Synthesis of BCN-dPEG$_4$-pyrene (24)

To a solution of 60a (50 mg, 0.095 mmol) in DCM (10 mL) was added 49 (30 mg, 0.11 mmol) and Et$_3$N (17 µL, 0.12 mmol). After stirring overnight at rt, the reaction mixture was concentrated under reduced pressure. Subsequent purification via flash column chromatography (DCM→DCM:MeOH 9:1) yielded product 24 (38 mg, 61%). $^1$H NMR (400 MHz, CDCl$_3$) δ (ppm) 8.29-8.26 (m, 2H), 8.19-8.11 (m, 4H), 8.06-7.97 (m, 4H), 7.04 (br. s, 1H), 5.24 (br. s, 1H), 5.16 (d, 2H, J=4 Hz), 4.06 (d, 2H, J=4 Hz), 3.76 (t, 2H, J=5.6 Hz), 3.50 (m, 2H), 3.39-3.22 (m, 14H), 2.56-2.53 (m, 2H), 2.27-2.13 (m, 7H), 1.29-1.25 (m, 2H), 0.87-0.83 (m, 2H).

Example 34. Synthesis of BCN-PEG$_8$-C(O)OSu (60b)

To a solution of amino-dPEG$_8$-acid (217 mg, 0.492 mmol) in anhydrous DMF (3 mL) were subsequently added 51 (143 mg, 0.492 mmol) and Et$_3$N (204 µL, 1.47 mmol).

The reaction mixture stirred for 3 h at rt, after which EDCI.HCl (0.88 g, 4.61 mmol) and NHS (88 mg, 0.77 mmol) were added. The resulting solution was stirred overnight at rt and poured into 50 mL NaHCO$_3$ (sat.) and 50 mL EtOAc. The layers were separated and the organic phase was washed with sat. NaHCO$_3$ (50 mL) and H$_2$O (30 mL). The organic phase was dried (Na$_2$SO$_4$), filtered and concentrated in vacuo. Gradient flash chromatography (MeCN→MeCN:H$_2$O 30:1) afforded product 60b as colorless oil (212 mg, 0.30 mmol, 60%).

$^1$H NMR (300 MHz, CDCl$_3$): δ (ppm) 4.13 (d, J=8.1 Hz, 2H), 3.84 (t, J=6.3 Hz, 2H), 3.68-3.59 (m, 28H), 3.54 (t, J=5.1 Hz, 2H), 3.36 (q, J=5.4 Hz, 2H), 2.89 (t, J=6.3 Hz, 2H), 2.82 (s, 4H), 2.35-2.15 (m, 6H), 1.68-1.48 (m, 2H), 1.44-1.23 (m, 1H), 1.00-0.86 (m, 2H). LRMS (ESI+) m/z calcd for C$_{34}$H$_{54}$N$_2$O$_{14}$ (M+Na$^+$)=737.8; found 737.3.

Example 35. Synthesis of BCN-PEG$_8$-Pyrene (25)

To a solution of 60b (100 mg, 0.14 mmol) in DCM (15 mL) was added 1-aminomethylpyrene.HCl 49 (50 mg, 0.19 mmol) and Et$_3$N (47 µL, 0.25 mmol). After stirring for 3 h, the reaction mixture was concentrated under reduced pressure. Subsequent purification via flash column chromatography (DCM→DCM:MeOH 95:5) yielded the product 25 (35 mg, 30%). $^1$H NMR (400 MHz, CDCl$_3$) δ (ppm) 8.30-8.28 (m, 1H), 8.21-8.13 (m, 4H), 8.05-7.99 (m, 4H), 7.22 (bs, 1H), 5.16 (d, 2H, J=5.2 Hz), 4.12 (d, 2H, J=8.0 Hz), 3.76 (t, 2H, J=6.0 Hz), 3.65-3.49 (m, 21H), 3.45-3.42 (m, 2H), 3.36-3.32 (m, 4H), 2.59-2.54 (m, 4H), 2.28-2.20 (m, 4H), 1.59-1.54 (m, 2H), 1.38-1.25 (m, 2H), 0.93-0.91 (m, 2H).

Example 36. Synthesis of (61)

To a solution of 57 (0.15 g, 1.0 mmol) in DCM (15 mL) was added CSI (87 µL, 0.14 g, 1.0 mmol), Et$_3$N (279 µL, 202 mg, 2.0 mmol) and a solution of H$_2$N-PEG$_3$-OH (251 mg, 1.3 mmol) in DCM (1 mL). After stirring for 2.5 h, the reaction mixture was quenched through addition of a solution of NH$_4$Cl (sat., 20 mL). After separation, the aqueous layer was extracted with DCM (20 mL). The combined organic layers were dried (Na$_2$SO$_4$) and concentrated. The residue was purified by gradient column chromatography (0→10% MeOH in DCM). Product 61 was obtained as colorless thick oil (254 mg, 0.57 mmol, 57%). $^1$H NMR (400 MHz, CDCl$_3$) δ (ppm) 6.81 (br. s, 1H), 4.26 (d, J=8.2 Hz, 2H), 3.80-3.70 (m, 4H), 3.70-3.58 (m, 10H), 3.36 (t, J=4.7 Hz, 2H), 2.36-2.16 (m, 6H), 1.64-1.49 (m, 2H), 1.40 (quintet, J=8.7 Hz, 1H), 1.04-0.92 (m, 2H).

Example 37. Synthesis of (62)

To a solution of 61 (242 mg, 0.54 mmol) in DCM (30 mL) were added p-nitrophenyl chloroformate (218 mg; 1.08 mmol) and Et$_3$N (226 µL, 164 mg, 1.62 mmol). The mixture was stirred for 17 h. and quenched with water (20 mL). After separation, the organic layer was dried (Na$_2$SO$_4$) and concentrated. The residue was purified by gradient column chromatography (EtOAc/pentane 1/1→EtOAc) to afford product 62 (259 mg, 0.38 mmol). LRMS (ESI) m/z calcd for C$_{33}$H$_{42}$N$_5$O$_{16}$S (M+NH$_4^+$)=796.23; found 796.52.

Example 38. Synthesis of BCN-Sulfamide-Pyrene (26)

Compound 62 (40 mg, 0.11 mmol) was dissolved in DCM (10 mL) and 49 (34 mg, 0.13 mmol) and Et$_3$N (30 µL, 0.21 mmol) were added. The reaction mixture was stirred for 4 h, concentrated under reduced pressure and purified on gradient flash column chromatography (DCM→DCM:MeOH 96:4). The fractions containing the product were washed with sat. NaHCO$_3$ (3×100 mL), dried over Na$_2$SO$_4$, filtrated and concentrated in vacuo to yield 26 (25 mg, 36%). $^1$H NMR (400 MHz, CDCl$_3$) δ (ppm) 8.29-8.26 (m, 2H), 8.19-8.11 (m, 4H), 8.06-7.97 (m, 4H), 6.87 (d, 1H, J=12 Hz), 5.78 (br. s, 2H), 5.12 (d, 2H, J=5.6 Hz), 4.31-4.26 (m, 2H), 3.97 (d, 2H, J=8.4 Hz), 3.69-3.62 (m, 4H), 3.28 (m, 2H), 2.18-1.96 (m, 7H), 1.28 (m, 1H), 0.79-0.74 (m, 2H).

Example 39. Synthesis of DIBAC-PEG$_4$-Pyrene (27)

Compound 45 (75 mg, 0.22 mmol) was dissolved in DCM (3 mL) followed by the addition of amino-PEG$_4$-carboxylic acid (53 mg, 0.20 mmol) and Et$_3$N (83 µL, 0.6 mmol). After stirring overnight additional 45 (25 mg, 0.07 mmol) was added and the reaction mixture was stirred for an additional 1 h. After complete conversion (based on TLC-analysis), N-hydroxysuccinimide (5 mg, 0.04 mmol) and EDC.HCl (70 mg, 0.36 mmol) were added and the reaction was stirred overnight at rt. To the reaction mixture was added 64 (60 mg, 0.2 mmol) and Et$_3$N (50 µL, 0.36 mmol) were added and after 1 h the reaction mixture was concentrated under reduced pressure. Purification via gradient flash column chromatography (DCM→DCM:MeOH 9:1) yielded product 27 (12 mg, 8%). $^1$H NMR (400 MHz, CDCl$_3$) δ (ppm) 8.61 (d, 1H, J=9.2 Hz), 8.23-8.21 (m, 2H), 8.17-8.10 (m, 4H), 8.07-8.02 (m, 3H), 7.59 (d, 1H, J=7.2 Hz), 7.38-7.18 (m, 7H), 7.06 (bs, 1H), 6.45 (m, 1H), 5.00 (d, 1H, J=13.6), 3.86-3.79 (m, 3H), 3.70-3.19 (m, 14H), 2.42-2.38 (m, 1H), 2.19-2.15 (m, 2H), 1.89-1.85 (m, 1H).

Example 40. Synthesis of DIBAC-PEG-Pyrene (28)

Compound 45 (24 mg, 0.07 mmol) was dissolved in DCM (1 mL) followed by the addition of amino-PEGs-carboxylic acid (27 mg, 0.06 mmol) and Et$_3$N (14 µL, 0.10 mmol). After stirring for 2 h, additional 45 (10 mg, 0.03 mmol) was added and the reaction mixture was stirred for on. Subsequently, NHS (10 mg, 0.08 mmol) and EDC.HCl (17 mg, 0.09 mmol) were added and the reaction was stirred for 2 h. Next 64 (21 mg, 0.08 mmol) and Et$_3$N (14 µL, 0.10 mmol) were added and after 4 h the reaction was quenched by the addition of water (3 mL). The organic layer was washed with water (2×3 mL), dried over Na$_2$SO$_4$, filtrated and concentrated under reduced pressure. Purification via flash column chromatography (DCM→DCM:MeOH 93:7) yielded the product (8 mg, 14%). $^1$H NMR (400 MHz, CDCl$_3$) δ (ppm) 8.55 (d, 1H, J=9.2 Hz), 8.19-7.86 (m, 7H), 7.59 (d, 1H, J=6.8 Hz), 7.33-7.18 (m, 8H), 6.99 (m, 1H), 6.45 (m, 1H), 5.03 (d, 1H, J=14.0), 3.78-3.74 (m, 3H), 3.65-3.29 (m, 29H), 2.43-2.37 (m, 1H) 2.25-2.21 (m, 2H), 1.91-1.84 (m, 1H).

Example 41. Synthesis of (65)

Compound 45 (50 mg, 0.14 mmol) was dissolved in DCM (3 mL) followed by the addition of 2-aminoethanol (10 µL, 0.16 mmol) and Et$_3$N (30 µL, 0.22 mmol). After 2 h, additional 2-aminoethanol (10 µL, 0.16 mmol) was added and the reaction mixture was stirred overnight at rt. Subsequently, water (5 mL) was added and the organic layer was washed with water (3×5 mL), dried over Na$_2$SO$_4$, filtrated and concentrated in vacuo. Purification via gradient flash column chromatography (DCM→DCM:MeOH 97:3)

yielded product 65 (32 mg, 79%). LRMS (ESI$^+$) m/z calcd for $C_{19}H_{16}NO_2$ (M+H$^+$)=290.12; found 290.30.

Example 42. Synthesis of DIBAC-Sulfamide-Pyrene (29)

Compound 65 (26 mg, 0.09 mmol) was dissolved in DCM (2 mL) followed by the addition of CSI (8 µL, 0.09 mmol). After 5 min. Et$_3$N (37 µL, 0.27 mmol) and 64 (26 mg, 0.09 mmol) were added and the reaction was stirred for 2 h at rt, after which the reaction was quenched through the addition of aqueous NH$_4$Cl (sat., 5 mL). The organic layer was washed with water (3×5 mL), dried over Na$_2$SO$_4$, filtrated and concentrated in vacuo. Purification via gradient flash column chromatography (DCM→DCM:MeOH 95:5) yielded product 29 (10 mg, 17%). $^1$H NMR (400 MHz, CDCl$_3$) δ (ppm) 8.49 (d, 1H, J=9.2 Hz), 8.25-8.18 (m, 3H), 8.11-7.95 (m, 5H), 7.38-7.00 (m, 8H), 6.05 (m, 1H), 5.96 (m, 1H), 4.62-4.58 (m, 1H). 4.52-4.47 (m, 1H), 4.11-4.08 (m, 1H), 3.81-3.78 (m, 1H), 3.64-3.60 (m, 1H), 3.06 (d, 1H, J=14 Hz), 2.90-2.87 (m, 2H), 2.17-2.09 (m, 1H), 1.62-1.56 (m, 2H).

Example 43-1. Synthesis of (30)

A solution of BCN-PEG$_4$-C(O)OSu (60a, 7.1 mg, 0.013 mmol) and Et$_3$N (9.1 µL, 6.6 mg, 65.5 µmol) in 1 mL DMF was added to H-Ahx-maytansin.TFA (10 mg, 0.011 mmol). The reaction was stirred for 20 h at rt and subsequently concentrated under reduced pressure. The residue was purified via reversed phase (C18) HPLC chromatography (30→90% MeCN (1% AcOH) in H$_2$O (1% AcOH). Product 30 was obtained as colorless liquid (8.9 mg, 7.5 µmol, 68%). LRMS (ESI$^+$) m/z calcd for $C_{60}H_{87}ClN_5O_{16}$ (M$^+$-H$_2$O) =1168.58; found 1168.87.

Example 43-2. Synthesis of BCN-PEG$_{12}$-C(O)OSu

To a solution of amino-dPEG$_{12}$-acid (43 mg, 0.069 mmol) in anhydrous DMF (1 mL) were added 51 (22 mg, 0.076 mmol) and triethylamine 24 µL, 0.174 mmol). The reaction mixture stirred for 5 h at rt, after which EDCI.HCl (27 mg, 0.139 mmol) and NHS (8 mg, 0.076 mmol) were added. The resulting solution was stirred overnight at rt and poured into 10 mL sat. NaHCO$_3$ and 10 mL DCM. The layers were separated and the organic phase was washed with H$_2$O (2×10 mL). The combined water layers were extracted with DCM (10 mL). The combined organic layers were dried (Na$_2$SO$_4$), filtered and concentrated in vacuo. Gradient flash column chromatography (MeCN→MeCN:H$_2$O 20:1, 10:1) afforded BCN-PEG$_{12}$-C(O)OSu.
$^1$H NMR (400 MHz, CDCl$_3$): δ (ppm) 4.14 (d, J=8.0 Hz, 2H), 3.85 (t, J=6.4 Hz, 2H), 3.69-3.60 (m, 44H), 3.56 (t, J=5.2 Hz, 2H), 3.36 (q, J=5.2 Hz, 2H), 2.91 (t, J=6.4 Hz, 2H), 2.84 (s, 4H), 2.36-2.17 (m, 6H), 1.65-1.51 (m, 2H), 1.44-1.23 (J=8.4 Hz, 1H), 1.00-0.88 (m, 2H). LRMS (ESI+) m/z calcd for $C_{42}H_{70}N_2O_{18}$ (M+H$^+$)=892.0; found 891.6.

Example 44. Synthesis of (31)

A solution of BCN-PEG$_{12}$-C(O)OSu (14 mg, 15.7 µmol) and Et$_3$N (9.1 µL, 6.6 mg, 65.5 µmol) in 1.1 mL DMF was added to H-Ahx-maytansin.TFA (10 mg, 0.011 mmol). After 18 h, 2,2'-(ethylenedioxy)bis(ethylamine) (2.3 µL, 2.3 mg, 16 µmol) was added and the mixture was concentrated. The residue was purified via reversed phase (C18) HPLC chromatography (30→90% MeCN (1% AcOH) in H$_2$O (1% AcOH). Product 31 was obtained as a colorless film (6.6 mg, 4.3 µmol, 39%). LRMS (ESI$^+$) m/z calcd for $C_{75}H_{118}ClN_5O_{25}$ (M$^+$-H$_2$O)=1520.79; found 1520.96.

Example 45. Synthesis of BCN-PEG$_{24}$-C(O)OSu

To a solution of amino-dPEG$_{24}$-acid (48 mg, 0.042 mmol) in anhydrous DMF (1 mL) were added 51 (14 mg, 0.048 mmol) and triethylamine (17 µL, 0.125 mmol). The reaction mixture was stirred at rt overnight, after which DCM (10 mL) and citric acid (10% aq. sol., 5 mL) were added. The water phase was extracted with DCM (15 mL) and the combined organic layers were dried (Na$_2$SO$_4$). After filtration the solvent was removed in vacuo. The crude product was redissolved in anhydrous DMF (1 mL) and EDCI.HCl (17 mg, 0.088 mmol) and NHS (8 mg, 0.070 mmol) were added. The resulting solution was stirred overnight at rt, after which an addition equivalent of EDCI.HCL (16 mg) and NHS (7 mg) were added. After 6 h the reaction mixture was poured into 10 mL sat. NaHCO$_3$ and 15 mL EtOAc. The layers were separated and the organic phase was washed with sat. NaHCO$_3$ (10 mL) and H$_2$O (10 mL). The organic phase was dried (Na$_2$SO$_4$), filtered and concentrated in vacuo. Gradient flash column chromatography (MeCN→MeCN:H$_2$O 20:1, 10:1, 5:1) afforded BCN-PEG$_{24}$-C(O)OSu as a colorless oil (32 mg, 0.022 mmol, 54%).
$^1$H NMR (400 MHz, CDCl$_3$): δ (ppm) 4.08 (d, J=8.0 Hz, 2H), 3.78 (t, J=6.4 Hz, 2H), 3.63-3.54 (m, 92H), 3.49 (t, J=5.2 Hz, 2H), 3.30 (q, J=5.2 Hz, 2H), 2.84 (t, J=6.4 Hz, 2H), 2.78 (s, 4H), 2.29-2.08 (m, 6H), 1.59-1.43 (m, 2H), 1.35-1.23 (m, 1H), 0.93-0.80 (m, 2H). LRMS (ESI+) m/z calcd for $C_{66}H_{118}N_2O_{30}$ (M+H$^+$)=1420.66; found 1420.0.

Example 46. Synthesis of (32)

A solution of BCN-PEG$_{24}$-C(O)OSu (25 mg, 17.6 µmol) and Et$_3$N (9.1 µL, 6.6 mg, 65.5 µmol) in 0.78 mL DMF was added to H-Ahx-maytansin.TFA (10 mg, 0.011 mmol). After 18 h, 2,2'-(ethylenedioxy)bis(ethylamine) (2.3 µL, 2.3 mg, 16 µmol) was added and the mixture was concentrated. The residue was purified via reversed phase (C18) HPLC chromatography (30→90% MeCN (1% AcOH) in H$_2$O (1% AcOH). The product was obtained as a colorless film (11.4 mg, 5.5 µmol, 50%). LRMS (ESI$^+$) m/z calcd for $C_{100}H_{171}ClN_5O_{37}^{3+}$ (M+3H$^+$)/3=690.05; found 690.05.

Example 47. Synthesis of (33)

A solution of H-Ahx-maytansin.TFA (20 mg, 0.023 mmol) in DMF (2 mL) was added to a solution of 62 (14 mg, 0.023 mmol) and Et$_3$N (9.5 µL, 6.9 mg, 0.068 mmol) in DMF (2 mL) and the resulting reaction mixture was stirred for 24 h. Title compound 33 was obtained in quantitative yield after silica gel column chromatography (29 mg, +99%). Proof of identity was performed at ADC stage.

Example 48. Synthesis of (34)

A solution of 60a (6.6 mg, 0.012 mmol) and Et$_3$N (6.8 µL, 4.9 mg, 48.5 µmol) in 1 mL DMF was added to H-Val-Cit-PABA-duocarmycin (10 mg, 0.0097 mmol). After 18 h, 2,2'-(ethylenedioxy)bis(ethylamine) (1.8 µL, 1.8 mg, 12 µmol) was added and the mixture was concentrated under reduced pressure. The residue was purified via reversed phase (C18) HPLC chromatography (30→90% MeCN (1% AcOH) in H$_2$O (1% AcOH). Product 34 was obtained as a colorless film (7.5 mg, 5.1 µmol, 53%). LRMS (ESI⁺) m/z calcd for $C_{71}H_{94}ClN_{10}O_{21}$ (M+H⁺)=1457.63; found 1456.89.

Example 49. Synthesis of (35)

A solution of 62 (6.0 mg, 9.8 µmol) and Et₃N (6.8 µL, 4.9 mg, 48.5 µmol) in DMF (1 mL) was added to H-Val-Cit-PABA-duocarmycin (10 mg, 0.0097 mmol). After 22 h, 2,2'-(ethylenedioxy)bis(ethylamine) (2.8 µL, 2.8 mg, 19 µmol) was added. After 1 h, the reaction mixture was concentrated under reduced pressure and the residue was purified via reversed phase (C18) HPLC chromatography (30→90% MeCN (1% AcOH) in H₂O (1% AcOH). Product 35 was obtained as a white solid (6.4 mg, 4.2 µmol. 44%). LRMS (ESI⁺) m/z calcd for $C_{69}H_{92}ClN_{12}O_{22}S$ (M+H⁺)=1507.59; found 1508.00.

Example 50. Synthesis of (36)

To a solution of 58 (229 mg, 0.64 mmol) in DCM (20 mL) were added p-nitrophenyl chloroformate (128 mg, 0.64 mmol) and Et₃N (268 µL, 194 mg, 1.92 mmol). The mixture was stirred overnight at rt and subsequently concentrated under reduced pressure. The residue was purified via gradient column chromatography (20→70% EtOAc in heptane (1% AcOH) to afford the PNP carbonate derivative of 58 as a white solid (206 mg, 0.39 mmol, 61%). ¹H NMR (400 MHz, CDCl₃) δ (ppm) 8.31-8.26 (m, 2H), 7.45-7.40 (m, 2H), 5.56 (t, J=6.0 Hz, 1H), 4.48-4.40 (m, 2H), 4.27 (d, J=8.2 Hz, 2H), 3.81-3.75 (m, 2H), 3.68 (t, J=5.0 Hz, 2H), 3.38-3.30 (m, 2H), 2.36-2.14 (m, 6H), 1.61-1.45 (m, 2H), 1.38 (quintet, J=8.7 Hz, 1H), 1.04-0.94 (m, 2H).

Next, to a solution of the PNP-derivative of 58 (4.1 mg, 7.8 µmol) and Et₃N (3.3 µL, 2.4 mg, 23.4 µmol) in DMF (1 mL) was added a solution of H-Val-Cit-PABA-Ahx-maytansin (10 mg, 8.6 µmol) in DMF (100 µL). After 20 h, 2,2'-(ethylenedioxy)bis(ethylamine) (5.7 µL, 5.6 mg, 38 µmol) was added and the mixture was concentrated under reduced pressure. The residue was purified via reversed phase (C18) HPLC chromatography (30→90% MeCN (1% AcOH) in H₂O (1% AcOH) to give 36 (2.2 mg, 1.4 µmol, 18%). LRMS (ESI⁺) m/z calcd for $C_{73}H_{103}ClN_{11}O_{21}S$ (M−18+H⁺)=1536.67; found 1537.08.

Example 51. Synthesis of (66)

To a stirring solution of 57 (500 mg, 3.33 mmol) in DCM (100 mL) was added CSI (290 µL, 471 mg, 3.33 mmol). After 20 min, Et₃N (1.4 mL, 1.0 g, 10 mmol) and a solution of diethanolamine.HCl (571 mg, 4.0 mmol) in DMF (5 mL) were added subsequently. After an additional 45 min., the reaction mixture was concentrated under reduced pressure and the residue was purified by gradient column chromatography (0→15% MeOH in DCM). Product 66 was obtained as colorless thick oil (767 mg, 2.13 mmol, 64%). ¹H NMR (400 MHz, CDCl₃) δ (ppm) 4.26 (d, J=8.2 Hz, 2H), 3.87 (t, J=4.9 Hz, 4H), 3.55 (t, J=4.9 Hz, 4H), 2.37-2.16 (m, 6H), 1.65-1.45 (m, 2H), 1.39 (quintet, J=8.6 Hz, 1H), 1.05-0.92 (m, 2H) Example 52. Synthesis of (67) To a suspension of 66 (206 mg, 0.57 mmol) in DCM (20 mL) was added Et₃N (318 µL, 231 mg, 2.28 mmol) and p-nitrophenyl chloroformate (230 mg, 1.14 mmoL, 2 eq.). The reaction mixture was stirred for 28 h at rt and subsequently concentrated. The residue was purified via gradient column chromatography (20→75% EtOAc in heptane), yielding 67 as slightly yellow thick oil (83 mg, 0.12 mmol, 21%). ¹H NMR (400 MHz, CDCl₃) δ (ppm) 8.31-8.24 (m, 4H), 7.43-7.34 (m, 4H), 4.53 (t, J=5.4 Hz, 2H), 4.22 (d, J=4.2 Hz, 2H), 3.87 (t, J=5.4 Hz, 4H), 2.35-2.15 (m, 6H), 1.55-1.40 (m, 2H), 1.35 (quintet, J=8.8 Hz, 1H), 1.03-0.92 (m, 2H).

Example 53. Synthesis of (37)

A solution of 67 (2.7 mg, 3.9 µmol) and Et₃N (2.7 µL, 2.0 mg, 19.5 µmol) in DMF (1 mL) was added to a solution of H-Val-Cit-PABA-Ahx-maytansin (10 mg, 0.0086 mmol) in DMF (100 µL). The mixture was allowed to react overnight at rt, and subsequently concentrated. A solution of 2,2'-(ethylenedioxy)bis(ethylamine) (2.8 µL, 2.8 mg, 19 µmol) in DMF (1 mL) was added. The reaction mixture was concentrated and the residue was purified via reversed phase (C18) HPLC chromatography (30→90% MeCN (1% AcOH) in H₂O (1% AcOH) to give compound 37 (4.8 mg, 1.7 µmol, 45%). LRMS (ESI⁺) m/z calcd for $C_{131}H_{186}Cl_2N_{20}O_{38}S$ (M+2H⁺)/2=1375.12; found 1375.51.

Example 54. Synthesis of (68)

To a stirring solution of 58 (47 mg, 0.13 mmol) in DCM (10 mL) was added CSI (11 µL, 18 mg, 0.13 mmol). After 30 min, Et₃N (91 µL, 66 mg, 0.65 mmol) and a solution of diethanolamine (16 mg, 0.16 mmol) in DMF (0.5 mL) were added. After 30 minutes p-nitrophenyl chloroformate (52 mg, 0.26 mmol) and Et₃N (54 µL, 39 mg, 0.39 mmol) were added. After an additional 4.5 h, the reaction mixture was concentrated and the residue was purified by gradient column chromatography (33→66% EtOAc/heptane (1% AcOH)) to afford 68 as colorless oil (88 mg, 0.098 mmol, 75%). ¹H NMR (400 MHz, CDCl₃) δ (ppm) 8.28-8.23 (m, 4H), 7.42-7.35 (m, 4H), 4.52 (t, J=5.4 Hz, 4H), 4.30 (d, J=8.3 Hz, 2H), 4.27-4.22 (m, 2H), 3.86 (t, J=5.3 Hz, 4H), 3.69-3.65 (m, 2H), 3.64-3.59 (m, 2H), 3.30-3.22 (m, 2H), 2.34-2.14 (m, 6H), 1.62-1.46 (m, 2H), 1.38 (quintet, J=8.7 Hz, 1H), 1.04-0.92 (m, 2H).

Example 55. Synthesis of (38)

A solution of 68 (3.9 mg, 4.3 µmol) and Et₃N (3.0 µL, 2.2 mg, 21.5 µmol) in DMF (1 mL) was added to a solution of H-Val-Cit-PABA-Ahx-maytansin (10 mg, 8.6 µmol) in DMF (100 µL). The mixture was allowed to react o.n. and concentrated. The residue was purified via reversed phase (C18) HPLC chromatography (30→90% MeCN (1% AcOH) in H₂O (1% AcOH) to give product 38 (3.9 mg, 1.32 µmol, 31%). LRMS (ESI⁺) m/z calcd for $C_{136}H_{196}Cl_2N_{22}O_{43}S_2$ (M+2H⁺)/2=1480.13; found 1480.35. LRMS (ESI⁺) m/z calcd for $C_{85}H_{119}ClN_{14}O_{31}S_2$(M+2H⁺)/2=965.36; found 965.54.

As a side-product, the mono-substituted Ahx-maytansin derivative of 68 was isolated (not depicted). LRMS (ESI⁺) calculated for $C_{85}H_{119}ClN_{14}O_{31}S_2^{2+}$ m/z 965.36 found 965.54.

Example 56. Synthesis of (39)

To the mono-substituted Ahx-maytansin derivative of 68, isolated as the side-product in example 55, was added a solution of Et₃N (0.7 µL, 0.5 mg, 5 µmol) in DMF (1 mL) and a solution of 1.2 mg (1.1 µmol) H-Val-Cit-PABA-MMAF. The mixture was allowed to react overnight and 2,2'-(ethylenedioxy)bis(ethylamine) (1 µL, 1.0 mg, 6.7 µmol) was added. After 15 min, the reaction mixture was concentrated. Reversed phase (C18) HPLC chromatography (30→90% MeCN (1% AcOH) in H₂O (1% AcOH) afforded 1.0 mg of the desired product. LRMS (ESI⁺) m/z calcd for $C_{137}H_{206}ClN_{23}O_{41}S_2(M+2H^+)/2=1464.69$; found 1465.66.

Example 57. Determination of HPLC Retention Time

Samples of compounds 19-38 were injected on an HPLC system equipped with an Phenomenex Luna C18(2) 5μ, 150×4.6 mm, 100 Å column and eluted with either a gradient of 10% MeCN (0.1% TFA)/90% water (0.1% TFA) to 90% MeCN (0.1% TFA)/10% water (0.1% TFA) or a gradient of 10% MeCN/90% 10 mM potassium phosphate buffer pH 7.4 to 90% MeCN/10% 10 mM potassium phosphate buffer pH 7.4. The retention times obtained for these compounds are depicted in Table 3.

Time Program:
0-12 min: 10% MeCN to 90% MeCN
12-14 min: 90% MeCN
14-15 min: 90% MeCN to 10% MeCN
15-17 min: 10% MeCN

TABLE 3

Retention times of compounds 19-23 and 30-38 on RP-HPLC.

| compound | retention time (min) 0.1% TFA | pH 7.4 |
|---|---|---|
| 19 (comp.) | 11.4 | 11.4 |
| 20 | 11.6 | 9.6 |
| 21 | 11.6 | 9.2 |
| 22 (comp.) | 12.7 | 12.6 |
| 23 | 10.6 | 6.9 |
| 30 (comp.) | 10.5 | 10.6 |
| 31 (comp.) | 10.1 | 10.1 |
| 32 (comp.) | 9.7 | 9.7 |
| 33 | 10.4 | 9.3 |
| 34 (comp.) | 11.5 | 11.5 |
| 35 | 11.6 | 10.0 |
| 36 | 10.4 | 9.3 |
| 37 | 11.2 | 10.5 |
| 38 | 11.1 | 9.5 |

Example 58. Competition Conjugation of 17 vs 18 to Trastuzumab(N300C)

Trastuzumab(N300C) (100 μM) was incubated for 2 hours at room temperature in PBS with 30 mM EDTA and 1 mM TCEP (10 eq.). Buffer was exchanged to PBS after which the partially reduced trastuzumab(N300C) (66.7 μM) was incubated with 1.33 mM dehydroascorbic acid (20 eq.). The reoxidized trastuzumab(N300C) (66.7 μM) was incubated with 0.4 mM maleimide 17 (6 eq.) and 0.4 mM maleimide 18 (6 eq.). After 1 hour incubation at room temperature the reaction was quenched by adding a 5-fold molar excess of N-acetylcysteine. Reaction products were digested with Fabricator™ (purchased from Genovis) and analyzed by MS-analysis (AccuTOF). Approximately 45% of the Fc-fragment was conjugated to maleimide 18 (24297 Da, expected mass=24299) and approximately 35% of the Fc-fragment was conjugated to maleimide 17 (24319 Da, expected mass=24323). The remaining 20% of Fc-fragments consists of various nonconjugated forms (ranging from 23776 to 23874 Da).

Example 59. Conjugation of 19-39 to 13b or 13c

To a solution of the appropriate trastuzumab(azide)₂ (8.8 μL, 0.2 mg, 22.7 mg/ml in Tris buffer pH 7.5 10 mM) was added Tris buffer pH 7.5 10 mM (4 μL) and the substrate (2 μL, 2 mM solution in MiliQ+5% DMA). The reaction was incubated at rt and samples (2 μL) were taken at pre-set time points. These samples were incubated with DTT (2 μL 0.2 M), diluted with MiliQ (30 μL) and subjected to MS analysis (AccuTof) to determine the conjugation efficiency (see Table 1 and 2).

Example 60. Aggregation

Figure 23:
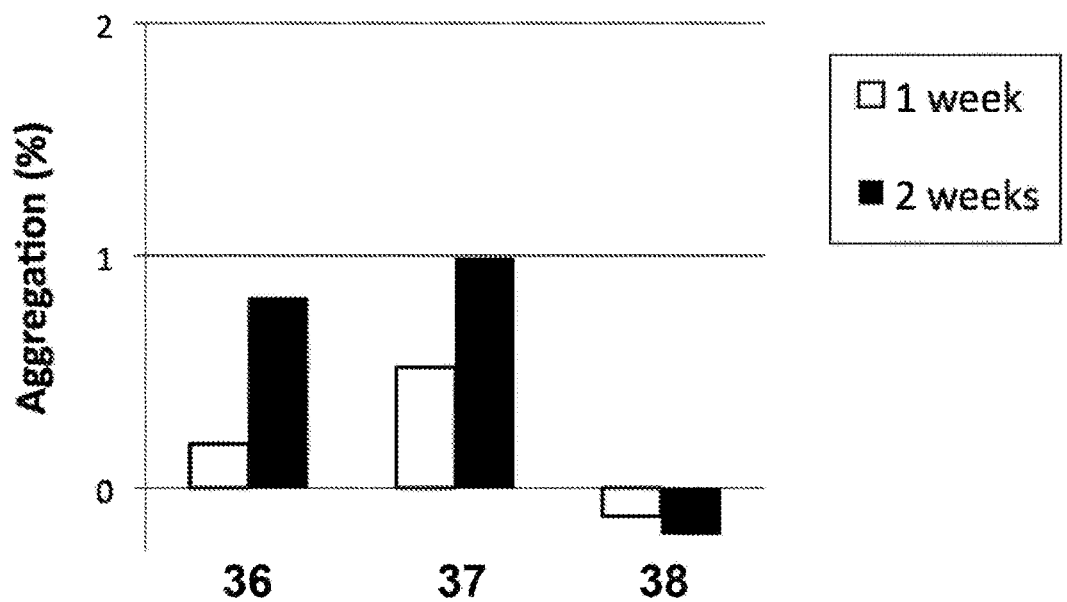
FIG. 23 shows the extent of aggregation for bioconjugates 36-38 according to the invention.

The tendency to aggregate was investigated for conjugates of 36, 37 and 38 with trastuzumab(F₂-GalNAz)₂ (13c), prepared according to example 59. The ADCs were incubated in PBS pH 7.4 at a concentration of 1 mg/mL at 37° C. The level of aggregation was analysed using a Superdex200 PC 3.2/30 column (GE Healthcare) after 0, 1 and 2 weeks. The results are depicted in FIG. 23. Aggregation remained below 1% upon going from the drug to antibody ratio of 2 (DAR2) of conjugate 36 to the drug to antibody ratio of 4 (DAR4) of conjugate 37, indicating the potential of sulfamide spacer to compensate the increase of lipophilicity imparted by doubling the number of payloads. For the bis-sulfamide linker of 38, no aggregation at all was observed. These results are a marked improvement over conventional bioconjugates prepared by alkyne-azide cycloaddition ligation.

Example 61. Aggregation

Figure 24:
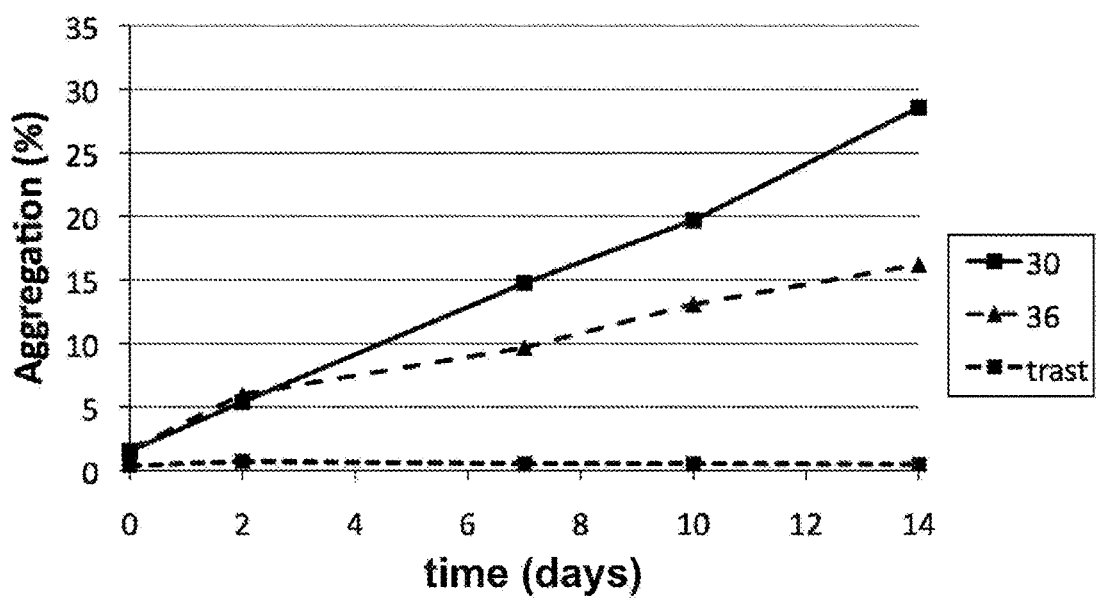
FIG. 24 shows the progress of aggregation over a period of 2 weeks for a bioconjugate according to the invention with a sulfamide linker (36 conjugated to 13a) vs. a comparative bioconjugate with a PEG linker (30 conjugated to 13a), as well as trastuzumab.

The tendency to aggregate for conjugates of 30 and 36 with trastuzumab(F₂-GalNAz)₂ (13c), prepared according to example 59, and for trastuzumab itself, was monitored over a period of 14 days. The conjugates were stored for 2 weeks at 40° C. at pH 5, and at day 0, 2, 7, 10 and 14 the extent of aggregation was determined. The level of aggregation was analysed using a Superdex200 PC 3.2/30 column (GE Healthcare). The results are depicted in FIG. 24. The conditions with increased stress (increased T, lower pH) compared to example 61 lead to increased aggregation. Nevertheless, aggregation was significantly reduced for the conjugate according to the invention (conjugate of 36 with trastuzumab(F₂-GalNAz)₂ (13c)), compared to the comparative bioconjugate of 30 with trastuzumab(F₂-GalNAz)₂ (13c), employing a PEG₄ spacer. Notably, trastuzumab itself did not show any tendency to aggregate, in view of the absence of hydrophobic groups such as a 1,2,3-triazole moiety fused to a cyclooctane and the maytansinoid moiety.

The invention claimed is:

1. A bioconjugate, comprising a biomolecule B and a target molecule D, wherein the bioconjugate further comprises a group according to formula (1):

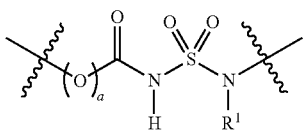

(1)

covalently linked to an alpha-end at one side of the formula (1) and an omega-end at the other side of the formula (1), the alpha-end comprising the biomolecule B and the omega-end comprising the target molecule D, wherein:
the wavy lines indicate covalent linkages to the alpha-end and the omega-end,
the biomolecule B is a glycoprotein;
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety, or a salt thereof.

2. The bioconjugate according to claim 1, wherein the bioconjugate is according to formula (5a) or (5b):

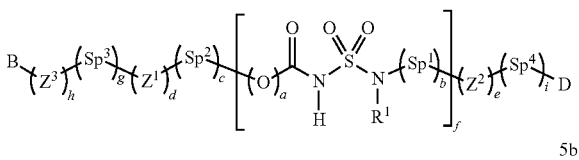

(5a)

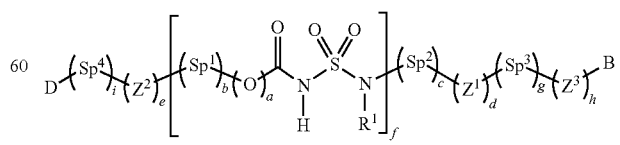

(5b)

wherein:
a is independently 0 or 1;
b is independently 0 or 1;

c is 0 or 1;
d is 0 or 1;
e is 0 or 1;
f is an integer in the range of 1 to 150;
g is 0 or 1;
h is 0 or 1;
i is 0 or 1;
B is a biomolecule, wherein the biomolecule is a glycoprotein;
D is a target molecule;
$Sp^1$ is a spacer moiety;
$Sp^2$ is a spacer moiety;
$Sp^3$ is a spacer moiety;
$Sp^4$ is a spacer moiety;
$Z^1$ is a connecting group that connects $Q^1$ or $Sp^3$ to $Sp^2$, O or C(O) or $N(R^1)$;
$Z^2$ is a connecting group that connects D or $Sp^4$ to $Sp^4$, $N(R^1)$, O or C(O);
$Z^3$ is a connecting group that connects B to $Sp^3$, $Z^1$, $Sp^2$, O or C(O); and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, -[($Sp^1$)b-($Z^2$)$_e$-($Sp^4$)$_i$-D] or -[($Sp^2$)$_c$-($Z^1$)$_d$-($Sp^3$)$_g$-$Q^1$], wherein $Sp^1$, $Sp^2$, $Sp^3$, $Sp^4$, $Z^1$, $Z^2$, D, $Q^1$, b, c, d, e, g and i are as defined above,
or a salt thereof.

3. The bioconjugate according to claim 1, further comprising a moiety that is obtainable by a cycloaddition reaction, which is situated between the alpha-end and the group according to formula (1).

4. The bioconjugate according to claim 2, wherein h is 1 and $Z^3$ is moiety that is obtainable by a conjugation reaction between functional group $F^1$, connected to the biomolecule, and reactive group $Q^1$, connected to the target molecule.

5. The bioconjugate according to claim 4, wherein $Q^1$ and $F^1$ are selected from the group consisting of alkenyl groups, alkynyl groups, (hetero)cycloalkynyl groups, bicyclo[6.1.0]non-4-yn-9-yl] groups, cycloalkenyl groups, tetrazinyl groups, azido groups, nitrile oxide groups, nitrone groups, nitrile imine groups, diazo groups, conjugated (hetero)diene group, 1,2-quinone groups and triazine groups, wherein $Q^1$ is an alkenyl group, alkynyl group, (hetero)cycloalkynyl group, bicyclo[6.1.0]non-4-yn-9-yl] group or cycloalkenyl group when $F^1$ is an azido group, nitrile oxide group, nitrone group, nitrile imine group, diazo group, conjugated (hetero)diene group, 1,2-quinone group and triazine group, and vice versa.

6. The bioconjugate according to claim 4, wherein:
$F^1$ is a thiol group and $Q^1$ is a N-maleimidyl group, an alkenyl group or an allenamide group;
$F^1$ is an amino group and $Q^1$ is a ketone groups, an activated ester group or an azido group;
$F^1$ is a ketone group and $Q^1$ is an (O-alkyl)hydroxylamino group or a hydrazine group;
$F^1$ is an alkynyl group and $Q^1$ is an azido group;
$F^1$ is an azido group and $Q^1$ is an alkynyl group; or
$F^1$ is a cyclopropenyl group, a trans-cyclooctene group or a cyclooctyne group, and $Q^1$ is a tetrazinyl group.

7. The bioconjugate according to claim 4, wherein in $Q^1$ is an alkene group or an alkyne group.

8. The bioconjugate according to claim 7, wherein $Q^1$ is according to formula (9a), (9q), (9n), (9o) or (9t):

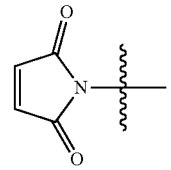

9a

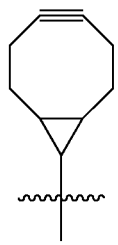

9q

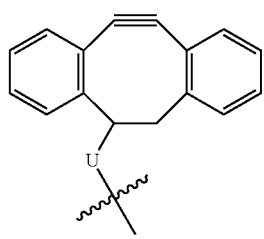

9n

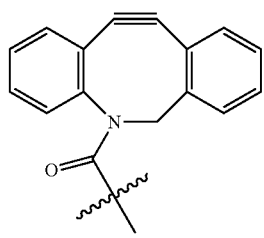

9o

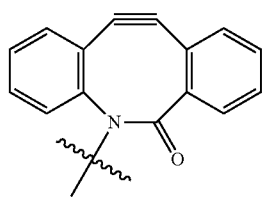

9p wherein U is O or $NR^9$, and $R^9$ is hydrogen, a linear or branched $C_1$-$C_{12}$ alkyl group or a $C_4$-$C_{12}$ (hetero)aryl group.

9. The bioconjugate according to claim 7, wherein $Q^1$ is an optionally substituted (hetero)cycloalkynyl group.

10. The bioconjugate according to claim 9, wherein $Q^1$ is bicyclo[6.1.0]non-4-yn-9-yl group.

11. The bioconjugate according to claim 4, wherein the conjugation reaction is a cycloaddition reaction.

12. The bioconjugate according to claim 11, wherein the cycloaddition is a Diels-Alder reaction or a 1,3-dipolar cycloaddition.

13. The bioconjugate according to claim 2, wherein $Sp^1$, $Sp^2$, $Sp^3$ and $Sp^4$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^3$, wherein $R^3$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

14. The bioconjugate according to claim 13, wherein $Sp^1$, $Sp^2$, $Sp^3$ and $Sp^4$ are independently selected from the group consisting of linear or branched $C_1$-$C_{20}$ alkylene groups, the alkylene groups being optionally substituted and optionally interrupted by one or more heteroatoms selected from the group consisting of O, S and $NR^3$, preferably O, wherein $R^3$ is independently selected from the group consisting of hydrogen and $C_1$-$C_4$ alkyl groups.

15. The bioconjugate according to claim 2, wherein Z1 and Z2 are independently selected from the group consisting of —O—, —S—, —$NR^2$—, —N═N—, C(O)—, —C(O)$NR^2$—,
—O—C(O)—, —O—C(O)—O—, —O—C(O)—$NR^2$, —$NR^2$—C(O)—, $NR^2$C(O)—O—, —$NR^2$—C(O)—$NR^2$—, —S—C(O)—, —S—C(O)—O—, —S—C(O)—$NR^2$—, —S(O)—, S(O)$_2$, —O—S(O)$_2$—, —O—S(O)$_2$—O—, —O—S(O)$_2$—$NR^2$—, —O—S(O)—, —O—S(O)—O—, O S(O)—$NR^2$—, —O—$NR^2$—C(O)—, —O—$NR^2$—C(O)—O—, —O—$NR^2$—C(O)—$NR^2$-, $NR^2$OC(O)—, —$NR^2$—O—C(O)—O—, —$NR^2$—O—C(O)—$NR^2$—, —O—$NR^2$—C(S)—, $ONR^2$C(S)—O—, —O—$NR^2$—C(S)—$NR^2$—, —$NR^2$—O—C(S)—, —$NR^2$—O—C(S)—O—, $NR^2$OC(S)—$NR^2$—, —O—C(S)—, —O—C(S)—O—, —O—C(S)—$NR^2$—, —$NR^2$—C(S)—, $NR^2$C(S)—O—, —$NR^2$—C(S)—$NR^2$—, —S—S(O)$_2$—, —S—S(O)$_2$—O—, —S—S(O)$_2$—$NR^2$—, $NR^2$OS(O)—, —$NR^2$—O—S(O)—O—, —$NR^2$—O—S(O)—$NR^2$—, —$NR^2$—O—S(O)$_2$—, —$NR^2$OS(O)$_2$—O—, —$NR^2$—O—S(O)$_2$—$NR^2$—, —O—$NR^2$—S(O)—, —O—$NR^2$—S(O)—O—, O $NR^2$—S(O)—$NR^2$—, —O—$NR^2$—S(O)$_2$—O—, —O—$NR^2$—S(O)$_2$—$NR^2$—, —O—$NR^2$—S(O)$_2$—,
O P(O)($R^2$)$_2$—, —S—P(O)($R^2$)$_2$—, —$NR^2$—P(O)($R^2$)$_2$— and combinations of two or more thereof, wherein $R^2$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

16. The bioconjugate according to claim 1, wherein the target molecule is selected from the group consisting of an active substance, a reporter molecule, a polymer, a solid surface, a hydrogel, a nanoparticle, a microparticle and a biomolecule.

17. The bioconjugate according to claim 1, wherein the glycoprotein is an antibody.

18. The bioconjugate according to claim 17, wherein the antibody specifically binds a cancer related antigen.

19. A process for the preparation of a bioconjugate according to claim 1, comprising the step of reacting a reactive group $Q^1$ of a linker-conjugate with a functional group $F^1$ of a biomolecule B under conditions such that the reactive group $Q^1$ is reacted with the functional group $F^1$ of the biomolecule to covalently link the glycoprotein to the linker-conjugate,
wherein the linker-conjugate is a compound comprising a group according to formula (1)

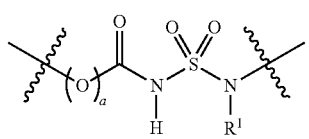

1 covalently linked to an alpha-end at one side of the formula (1) and an omega-end at the other side of the formula (1), the alpha-end comprising the reactive group $Q^1$ capable of reacting with a functional group $F^1$ present on the biomolecule B and the omega-end comprising a target molecule D,
wherein
the wavy lines indicate covalent linkages to the alpha-end and the omega-end,
the biomolecule B is a glycoprotein;
a is 0 or 1; and
$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups, or $R^1$ is a target molecule D, wherein the target molecule is optionally connected to N via a spacer moiety,
or a salt thereof.

20. The process according to claim 19, wherein, in the group according to formula (1), a is 0.

21. The process according to claim 19, wherein, in the group according to formula (1), a is 1.

22. The process according to claim 19, wherein the linker-conjugate is according to formula (4a) or (4b):

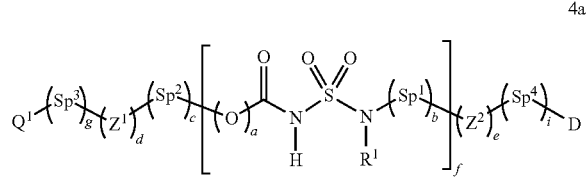

4a

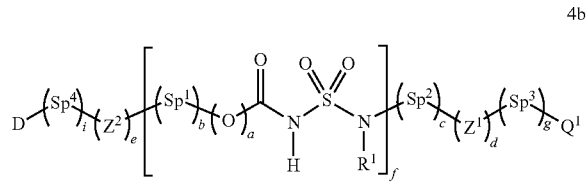

4b wherein:
- a is independently 0 or 1;
- b is independently 0 or 1;
- c is 0 or 1;
- d is 0 or 1;
- e is 0 or 1;
- f is an integer in the range of 1 to 150;
- g is 0 or 1;
- i is 0 or 1;
- D is a target molecule;
- Q1 is a reactive group capable of reacting with a functional group $F^1$;
- $Sp^1$ is a spacer moiety;
- $Sp^2$ is a spacer moiety;
- $Sp^3$ is a spacer moiety;
- $Sp^4$ is a spacer moiety;
- $Z^1$ is a connecting group that connects $Q^1$ or $Sp^3$ to $Sp^2$, O or C(O) or $N(R^1)$;
- $Z^2$ is a connecting group that connects D or $Sp^4$ to $Sp^1$, $N(R^1)$, O or C(O); and
- $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; or $R^1$ is D, -[$(Sp^1)_b$-$(Z^2)_e$-$(Sp^4)_i$-D] or —[$(Sp^2)_c$-$(Z^1)_d$—$(Sp^3)_g$-$Q^1$], wherein $Sp^1$, $Sp^2$, $Sp^3$, $Sp^4$, $Z^1$, $Z^2$, D, $Q^1$, b, c, d, e, g and i are as defined above, or a salt thereof.

23. The process according to claim 19, wherein $Q^1$ is an alkenyl group, alkynyl group, (hetero)cycloalkynyl group, bicyclo[6.1.0] non-4-yn-9-yl] group or cycloalkenyl group.

24. The process according to claim 19, wherein $Q^1$ is an optionally substituted (hetero)cycloalkynyl group.

25. The process according to claim 24, wherein $Q^1$ is a bicyclo[6.1.0]non-4-yn-9-yl] group.

* * * * *